(12) United States Patent
Theill et al.

(10) Patent No.: US 6,774,106 B2
(45) Date of Patent: Aug. 10, 2004

(54) METHODS AND COMPOSITIONS OF MATTER CONCERNING APRIL/G70, BCMA, BLYS/AGP-3 AND TACI

(75) Inventors: Lars Eyde Theill, Thousand Oaks, CA (US); Gang Yu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/854,864

(22) Filed: May 14, 2001

(65) Prior Publication Data

US 2002/0081296 A1 Jun. 27, 2002

Related U.S. Application Data

(60) Provisional application No. 60/204,039, filed on May 12, 2000, and provisional application No. 60/214,591, filed on Jun. 27, 2000.

(51) Int. Cl.⁷ .......................... A61K 38/16; A61K 39/00

(52) U.S. Cl. ..................... 514/12; 424/185.1; 424/192.1

(58) Field of Search .......................... 424/144.1, 152.1, 424/185.1, 192.1; 514/12

(56) References Cited

U.S. PATENT DOCUMENTS

| | | | |
|---|---|---|---|
| 4,289,872 A | 9/1981 | Denkewalter et al. | |
| 4,699,880 A | 10/1987 | Goldstein | |
| 4,816,567 A | 3/1989 | Cabilly et al. | |
| 5,229,490 A | 7/1993 | Tam | |

FOREIGN PATENT DOCUMENTS

| | | |
|---|---|---|
| EP | 0 869 180 | 10/1998 |
| EP | 0 911 633 | 4/1999 |
| EP | 0 919 620 | 8/1999 |
| WO | WO 93/21259 | 10/1993 |
| WO | WO 96/32478 | 10/1996 |
| WO | WO 97/34631 | 9/1997 |
| WO | WO 98/18921 | 5/1998 |
| WO | WO 98/27114 | 6/1998 |
| WO | WO 98/39361 | 9/1998 |
| WO | WO 98/55620 | 12/1998 |
| WO | WO 98/55621 | 12/1998 |
| WO | WO 99/00518 | 1/1999 |
| WO | WO 99/11791 | 3/1999 |
| WO | WO 99/12964 | 3/1999 |
| WO | WO 99/12965 | 3/1999 |
| WO | WO 99/28462 | 6/1999 |
| WO | WO 99/33980 | 7/1999 |
| WO | WO 99/35170 | 7/1999 |
| WO | WO 00/24782 | 5/2000 |
| WO | WO 00/40716 | 7/2000 |
| WO | WO 01/12812 | 2/2001 |
| WO | WO 01/24811 | 4/2001 |
| WO | WO 01/60397 | 8/2001 |

OTHER PUBLICATIONS

Adams et al. (1985), "The c–myc oncogene driven by immunoglobulin enhancers induces lymphoid malignancy in transgenic mice," *Nature*, 318:533–538.

Alexander et al. (1987), "Expression of the c–myc Oncogene under Control of an Immunoglobulin Enhancer in Eµ–myc Transgenic Mice," *Mol. Cell. Biol.*, 7(4):1436–1444.

Banner et al. (1993), "Crystal Structure of the Soluble Human 55 kd TNF Receptor–Human TNFβ Complex: Implications for TNF Receptor Activation," *Cell* 73:431–445.

Benoist and Chambon (1981), "In vivo sequence requirements of the SV40 early promoter region," *Nature*, 290:304–310.

Boulianne et al. (1984), "Production of functional chimaeric mouse/human antibody," *Nature*, 312:643–646.

Bowie et al. (1991), "A Method to Identify Protein Sequences That Fold into a Known Three–Dimensional Structure," *Science*, 253:164–170.

Brenner et al. (1997), "Population statistics of protein structures: lessons from structural classifications," *Curr. Op. Struct. Biol.*, 7:369–376.

Brinster et al. (1982), "Regulation of metallothionein–thymidine kinase fusion plasmids injected into mouse eggs," *Nature*, 296:39–42.

(List continued on next page.)

Primary Examiner—Christina Chan
Assistant Examiner—Maher Haddad
(74) Attorney, Agent, or Firm—Randolph N. Mohr

(57) ABSTRACT

This invention concerns interactions among APRIL/G70, AGP-3/BLYS, BCMA, and TACI and related methods of use and compositions of matter. It has been found that (1) sAPRIL/G70 binds to the cell-surface receptors BCMA and TACI on T and B lymphoma cells, resulting in stimulation of proliferation of primary human and mouse B and T cells both in vitro and in vivo; (2) APRIL competes with AGP3's binding to TACI and BCMA; (3) sBCMA inhibits APRIL and AGP3 binding to its receptors; (4) sBCMA ameliorates T cell dependent and T cell independent humoral immune responses in vivo; (5) sTACI inhibits APRIL and AGP3 binding to its receptors and ameliorates T cell dependent and T cell independent humoral immune responses in vivo; and (6) BCMA exhibits similarity with TACI within a single cysteine rich domain located N-terminal to a potential transmembrane domain. These discoveries provides a strategy for development of therapeutics for treatment of autoimmune diseases, and cancer, for prevention of transplant rejection. Disease states and disease parameters associated with APRIL and AGP-3 may be affected by modulation of BCMA or TACI; disease states and parameters associated with TACI can be affected by modulation of APRIL; disease states and parameters can be affected by modulation of any of TACI, BCMA, APRIL and AGP-3 by a single therapeutic agent or two or more therapeutic agents together.

2 Claims, 49 Drawing Sheets

OTHER PUBLICATIONS

Bruggermann et al. (1993), "Designer Mice: The Production of Human Antibody Repertoires in Transgenic Animals," *Year in Immunol.*, 7:33–40.

Cabilly, et al. (1984), "Generation of antibody activity from immunoglobulin polypeptide chains produced in *Excherichia coli*," *Proc. Natl. Acad. Sci. USA*, 81:3273–3277.

Castro et al. (1996), "Fas Modulation of Apoptosis during Negative Selection of Thymocytes," *Immunity*, 5:617–627.

Chichepotiche et al. (1997), "TWEAK, a New Secreted Ligand in the Tumor Necrosis Factor Family that Weakly Induces Apoptosis," *J. Biol. Chem.* 272(51):32401–32410.

Chou et al. (1978), "Prediction of the Secondary Structure of Proteins from Their Amino Acid Sequence," *Adv. Enzymol. Relat. Areas Mol. Biol.*, 47:45–148 (1978).

Chou et al. (1978), "Empirical Predictions of Protein Conformation," *Ann. Rev. Biochem.*, 47:251–276.

Chou et al. (1974), "Prediction of Protein Conformation," *Biochemistry*, 13(2):222–245.

Chou et al. (1974), "Conformational Parameters for Amino Acids in Helical, β–Sheet, and Random Coil Regions Calculated from Proteins," *Biochemistry*, 13(2):211–222.

Chou et al. (1979), "Prediction of β–turns," *Biophys. J.*, 26:367–384.

De Boer et al., (1983), "The tac promoter: A functional hybrid derived from the trp and Iac promotors," Proc. Natl. Acad. Sci. USA, 80:21–25.

Ellison et al. (1982), "The nucleotide sequence of a human immunoglobulin $C_{\gamma 1}$ gene," *Nucleic Acids Res.* 10(13):4071–4079.

Gras et al. (1995), "BCMAp: an integral membrane protein in the Golgi apparatus of human mature B lymphocytes," *Intl. Immunol.* 7(7):1093–1106.

Gribskov et al. (1990), "Profile Analysis," *Meth. Enzym.*, 183:146–159.

Gribskov et al. (1987), "Profile analysis: Detection of distantly related proteins," *Proc. Natl. Acad. Sci.*, 84:4355–4358.

Gross et al. (2000), "TACI and BCMA are receptors for a TNF homologue implicated in B–cell autoimmune disease," *Nature* 404:995–999.

Grosschedl et al. (1984), "Introduction of a μ Immunoglobulin Gene into the Mouse Germ Line: Specific Expression in Lymphoid Cells and Synthesis of Functional Antibody," *Cell*, 38:647–658.

Hahne et al. (1998), "APRIL, a New Ligand of the Tumor Necrosis Factor Family, Stimulates Tumor Cell Growth," *J. Exp. Med.* 188(6):1185–1190.

Hammer et al. (1987), "Diversity of Alpha–Fetoprotein Gene Expression in Mice is Generated by a Combination of Separate Enhancer Elements," *Science*, 235:53–58.

Holm et al. (1999), "Protein folds and families: sequence and structure alignments," *Nucl. Acid. Res.*, 27(1):244–247.

Hoogenboom et al. (1992), "Human Antibodies from Synthetic Repertoires of Germline $V_H$ Gene Segments Rearranged in Vitro," *J. Mol. Biol.*, 227:381–388.

Houghten (1985), "General method for the rapid solid–phase synthesis of large numbers of peptides: Specificity of antigen–antibody interaction at the level of individual amino acids," *Proc. Natl. Acad. Sci. USA*, 82:5131–5135.

Hsu et al. (1999), "Tumor necrosis factor receptor family member RANK mediates osteoclast differentiation and activation induced by osteoprotegerin ligand," *Proc. Natl. Acad; Sci. USA* 96:3540–3545.

Jakobovits et al. (1993), "Germ–line transmission and expression of a human–derived yeast artificial chromosome," *Nature*, 362:255–259.

Jakobovits et al. (1993), "Analysis of homozygous mutant chimeric mice: Deletion of the immunoglobulin heavy-–chain joining region blocks B–cell development and antibody production," *Proc. Natl. Acad. Sci.*, 90:2551–2555.

Jones et al. (1986), "Replacing the complementarity–determining regions in a human antibody with those from a mouse," *Nature*, 321:522–525.

Jones, D. (1997), "Progress in protein structure prediction," *Curr. Opin. Struct. Biol.*, 7(3):377–387.

Kelly et al. (2000), "APRIL/TRDL–1, a Tumor Necrosis Factor–like Ligand, Stimulates Cell Death," *Cancer Res.* 60:1021–1027.

Kelsey et al. (1987), "Species– and tissue–specific expression of human $o_1$–antitrypsin in transgenic mice," *Genes and Devel.*, 1:161–171.

Kitts et al (1993), "A Method for Producing Recombinant Baculovirus Expression Vectors at High Frequency," *Biotechniques*, 14(5):810–817.

Kohler et al. (1975), "Continuous cultures of fused cells secreting antibody of predefined specificity," *Nature*, 256:495–497.

Kollias et al. (1986), "Regulated Expression of Human $^A\gamma$–, β–, and Hybrid γβ–Globin Genes in Transgenic Mice: Manipulation of the Developmental Expression Patterns," *Cell*, 46:89–94.

Kozbor et al. (1984), "A Human Hybrid Myeloma for Production of Human Monoclonal Antibodies," *J. Immunol.*, 133(6):3001–3005.

Kranz et al. (1981), "Restricted reassociation of heavy and light chains from hapten–specific monoclonal antibodies," *Proc. Natl. Acad. Sci. USA*, 78(9):5807–5811.

Krumlauf et al. (1985), "Developmental Regulation of α–Fetoprotein Genes in Transgenic Mice," *Mol. Cell. Biol.*, 5(7):1639–1648.

Kyte et al. (1982), "A Simple Method for Displaying the Hydropathic Character of a Protein," *J. Mol. Biol.*, 157:105–132.

Laabi et al. (1992), "A new gene, BCM, on chromosome 16 is fused to the interleukin 2 gene by a t(4;16)(q26;p13) translocation in a malignant T cell lymphoma," *EMBO J.* 11(11):3897–3904.

Lacey et al. (1998), "Osteoprotegerin Ligand is a Cytokine that Regulates Osteoclast Differentiation and Activation," *Cell* 93:165–176.

Leder et al (1986), "Consequences of Widespread Deregulation of the c–myc Gene in Transgenic Mice: Multiple Neoplasms and Normal Development," *Cell*, 45:485–495.

Lewis et al. (1995), "Use of a Novel Mutagenesis Strategy, Optimized Residue Substitution, to Decrease the Off–Rate of an Anti–gp 120 Antibody," *Mol. Immunol.* 32(14/15):1065–1072.

Liu et al. (1987), "Chimeric mouse–human IgG1 antibody that can mediate lysis of cancer cells," *Proc. Natl. Acad. Sci. USA*, 84:3439–3443.

Lucklow (1993), "Baculovirus systems for the expression of human gene products," *Curr. Opin. Biotechnol.*, 4:564–572.

Lucklow et al. (1993), "Efficient Generation of Infectious Recombinant Baculoviruses by Site–Specific Transposon–Mediated Insertion of Foreign Genes into a Baculovirus Genome Propagated in *Excherichia coli*," *J. Virol.*, 67(8):4566–4579.

MacDonald (1987), "Expression of the Pancreatic Elastase I Gene in Transgenic Mice," *Hepatology* 7,(1):42S–51S.

MacLennan et al., (1998), "Structure–Function Relationships in the $Ca^{2+}$—Binding and Translocation Domain of SERCA1: physiological correlates in Brody disease," *Acta Physiol. Scand. Suppl.*, 643:55–67.

Madry et al. (1998), "The characterization of murine BCMA gene defines it as a new member of the tumor necrosis factor receptor superfamily," *Intl. Immunol.* 10(11):1693–1702.

Magram et al. (1985), "Developmental regulation of a cloned adult β–globin gene in transgenic mice," *Nature*, 315:338–340.

Marks et al. (1992), "By–passing Immunization: Building High Affinity Human Antibodies by Chain Shuffling," *Biotechnology*, 10:779–783.

Marston et al. (1990), "Solubilization of Protein Aggregates," *Meth. Enz.*, 182:264–276.

Mason et al. (1986), "The Hypogonadal Mouse: Reproductive Functions Restored by Gene Therapy," *Science*, 234:1372–1378.

Mauri et al. (1998), "LIGHT, a New Member of the TNF Superfamily, and Lymphotoxin ο are Ligands for Herpesvirus Entry Mediator," *Immunity*, 8:21–30.

Merrifield et al. (1963), "Solid Phase Peptide Synthesis," *J.Am. Chem. Soc.*, 85:2149–2154.

Morrison et al.(1984), "Chimeric human antibody molecules: Mouse antigen–binding domains with human constant region domains," *Proc. Natl. Acad. Sci. USA*, 81:6851–6855.

Moult (1996), "The current state of the art in protein structure prediction," *Curr. Op. in Biotech.*, 7:422–427.

Muller (1983), "Determination of Affinity and Specificity of Anti–Hapten Antibodies by Competitive Radioimmunoassay," *Meth. Enzymol.*, 92:589–601.

Nagata, S. & Suda, T. (1995), "Fas and Fas ligand: Ipr and gld mutations," *Immunology Today*, 16(1):39–43.

Neuberger et al. (1985), "A hapten–specific chimaeric IgE antibody with human physiological effector function," *Nature*, 314(21):268–270.

Noelle (1996), "CD40 and its Ligand in Host Defense," *Immunity* 4:415–419.

Ornitz et al. (1986), "Elastase I Promoter Directs Expression of Human Growth Hormone and SV40 T Antigen Genes to Pancreatic Acinar Cells in Transgenic Mice," Cold Spring Harbor Symp. Quant. Biol., 50:399–409.

Pinkert et al. (1987), "An albumin enhancer located 10 kb upstream functions along with its promoter to direct efficient, liver–specific expression in transgenic mice," *Genes and Devel.*, 1:268–276.

Readhead et al. (1987), "Expression of a Myelin Basic Protein Gene in Transgenic Shiverer Mice: Correction of the Dysmyelinating Phenotype," *Cell*, 48:703–712.

Riechmann et al. (1988), "Reshaping human antibodies for therapy," *Nature*, 332:323–327.

Sasaki et al., (1998), "Structure–Mutation Analysis of the ATPase Site of Dictyostelium Discoideum Myosin II," *Adv. Biophys.*, 35:1–24.

Shu et al. (1999), "TALL–1 is a novel member of the TNF family that is down–regulated by mitogens," *J. Leukocyte Biology* 65:680–683.

Sippl et al.(1996), "Threading thrills and threats," *Structure*, 4:15–19.

Smith et al. (1994), "The TNF Receptor Superfamily of Cellular and Viral Proteins: Activation, Costimulation, and Death," *Cell* 76:959–962.

Swift et al. (1984), "Tissue–Specific Expression of the Rat Pancreatic Elastase I Gene in Transgenic Mice," *Cell*, 38:639–646.

Tracey & Cerami (1994), "Tumor Necrosis Factor: A Pleiotropic Cytokine and Therapeutic Target," *Annu. Rev. Med.* 45:491–503.

Urlaub et al. (1980), "Isolation of Chinese hamster cell mutants deficient in dihydrofolate reductase activity," *Proc. Natl. Acad. Sci. USA*, 77(7):4216–4220.

Verhoeyen et al. (1988), "Reshaping Human Antibodies: Grafting an Antilysozyme Activity," *Science*, 239:1534–1536.

Villa–Kamaroff et al. (1978), "A bacterial clone synthesizing proinsulin," *Proc. Natl. Acad. Sci. USA*. 75(8):3727–3731.

von Bulow & Bram (1997), "NF–AT Activation Induced by a CAML–Interacting Member of the Tumor Necrosis Factor Receptor Superfamily," *Science*, 278:138–141.

Wagner et al. (1981), "Nucleotide sequence of the thymidine kinase gene of herpes simplex virus type 1," *Proc. Natl. Acad. Sci. USA*, 78(3):1444–1445.

Wahl et al., J. Nucl. Med., 24:316–325 (1983).

Wallach et al. (1999), "Tumor Necrosis Factor Receptor and Fas Signaling Mechanisms," *Annual Review of Immunology* 17:331–367.

Yamamoto et al. (1980), "Identification of a Functional Promoter in the Long Terminal Repeat of Rous Sarcoma Virus," *Cell*, 22:787–797.

Cubillos et al. (1997), "Effect of blocking TNF on IL–6 levels and metastasis in a B16–BL6 melanoma/mouse model," *Anticancer Research* 17(3C): 2207–2211.

Li et al. (2001), "A peptide antagonist mimicking the $3^{rd}$ TNF–like cysteine–rich domain of mouse OPG inhibits RANKL/M–CSF induced osteoclastogenesis," *J. Bone and Mineral Research* 16(1): S209.

Thompson et al. (2000), "BAFF binds to the tumor necrosis factor receptor–like molecules B cell maturation antigen and is important for maintaining the peripheral B cell population," *J. Exp. Med.* 192(1): 129–135.

Xia et al. (2000) "TACI is a TRAF–interacting receptor for TALL–1, a tumor necrosis factor family member involved in B cell regulation," *J. Exp. Med.* 192(1): 137–143.

Yu et al. (2000), "APRIL and TALL–I and Receptors BCMA and TACI: System for Regulating Humoral Immunity, " *Nature Immunology* 1(3): 1529–2908.

FIG. 1

Sequence of human APRIL (SEQ ID NOS: 1 and 2)

Human G70 cDNA (SEQ ID NO 1)
Length: 1465 bp

```
    1   GCCAACCTTC CCTCCCCCAA CCCTGGGGCC GCCCCAGGGT TCCTGCGCAC
   51   TGCCTGTTCC TCCTGGGTGT CACTGGCAGC CCTGTCCTTC CTAGAGGGAC
  101   TGGAACCTAA TTCTCCTGAG GCTGAGGGAG GGTGGAGGGT CTCAAGGCAA
  151   CGCTGGCCCC ACGACGGAGT GCCAGGAGCA CTAACAGTAC CCTTAGCTTG
  201   CTTTCCTCCT CCCTCCTTTT TATTTTCAAG TTCCTTTTTA TTTCTCCTTG
  251   CGTAACAACC TTCTTCCCTT CTGCACCACT GCCCGTACCC TTACCCGCCC
  301   CGCCACCTCC TTGCTACCCC ACTCTTGAAA CCACAGCTGT TGGCAGGGTC
  351   CCCAGCTCAT GCCAGCCTCA TCTCCTTTCT TGCTAGCCCC CAAAGGGCCT
  401   CCAGGCAACA TGGGGGGCCC AGTCAGAGAG CCGGCACTCT CAGTTGCCCT
  451   CTGGTTGAGT TGGGGGGCAG CTCTGGGGGC CGTGGCTTGT GCCATGGCTC
  501   TGCTGACCCA ACAAACAGAG CTGCAGAGCC TCAGGAGAGA GGTGAGCCGG
  551   CTGCAGGGGA CAGGAGGCCC CTCCCAGAAT GGGGAAGGGT ATCCCTGGCA
  601   GAGTCTCCCG GAGCAGAGTT CCGATGCCCT GGAAGCCTGG AGAGTGGGG
  651   AGAGATCCCG GAAAAGGAGA GCAGTGCTCA CCCAAAAACA GAAGAAGCAG
  701   CACTCTGTCC TGCACCTGGT TCCCATTAAC GCCACCTCCA AGGATGACTC
  751   CGATGTGACA GAGGTGATGT GGCAACCAGC TCTTAGGCGT GGGAGAGGCC
  801   TACAGGCCCA AGGATATGGT GTCCGAATCC AGGATGCTGG AGTTTATCTG
  851   CTGTATAGCC AGGTCCTGTT TCAAGACGTG ACTTTCACCA TGGGTCAGGT
  901   GGTGTCTCGA GAAGGCCAAG GAAGGCAGGA GACTCTATTC CGATGTATAA
  951   GAAGTATGCC CTCCCACCCG GACCGGGCCT ACAACAGCTG CTATAGCGCA
 1001   GGTGTCTTCC ATTTACACCA AGGGGATATT CTGAGTGTCA TAATTCCCCG
 1051   GGCAAGGGCG AAACTTAACC TCTCTCCACA TGGAACCTTC CTGGGGTTTG
 1101   TGAAACTGTG ATTGTGTTAT AAAAAGTGGC TCCCAGCTTG AAGACCAGG
 1151   GTGGGTACAT ACTGGAGACA GCCAAGAGCT GAGTATATAA AGGAGAGGGA
 1201   ATGTGCAGGA ACAGAGGCGT CTTCCTGGGT TTGGCTCCCC GTTCCTCACT
 1251   TTTCCCTTTT CATTCCCACC CCTAGACTT TGATTTTACG GATATCTTGC
 1301   TTCTGTTCCC CATGGAGCTC CGAATTCTTG CGTGTGTGTA GATGAGGGC
 1351   GGGGGACGGG CGCCAGGCAT TGTTCAGACC TGGTCGGGGC CCACTGGAAG
 1401   CATCCAGAAC AGCACCACCA TCTAACGGCC GCTCGAGGGA AGCACCCGGC
 1451   GGTTTGGGCG AAGTC
```

The proposed transmembrane domains are boxed human G70 protein sequence (SEQ ID NO 2)

```
    1   MPASSPFLLA PKGPPGNMGG PVREPALSVA LWLSWGAALG AVACAMALLT
   51   QQTELQSLRR EVSRLQGTGG PSQNGEGYPW QSLPEQSSDA LEAWESGERS
  101   RKRRAVLTQK QKKQHSVLHL VPINATSKDD SDVTEVMWQP ALRRGRGLQA
  151   QGYGVRIQDA GVYLLYSQVL FQDVTFTMGQ VVSREGQGRQ ETLFRCIRSM
  201   PSHPDRAYNS CYSAGVFHLH QGDILSVIIP RARAKLNLSP HGTFLGFV
```

FIG. 2A

Sequence of mouse G70 (SEQ ID NOS: 3 and 4)

Mouse G70 (SEQ ID NO 3)

```
   1  CATGCCGAGT GCTTTGTGTG TGTTACCTGC TCTAAGAAGC TGGCTGGGCA
  51  GCGTTTCACC GCTGTGGAGG ACCAGTATTA CTGCGTGGAT TGCTACAAGA
 101  ACTTTGTGGC CAAGAAGTGT GCTGGATGCA AGAACCCCAT CACTGGGTTT
 151  GGTAAAGGCT CCAGTGTGGT GGCCTATGAA GGACAATCCT GGCACGACTA
 201  CTGCTTCCAC TGCAAAAAAT GCTCCGTGAA TCTGGCCAAC AAGCGCTTTG
 251  TATTTCATAA TGAGCAGGTG TATTGCCCTG ACTGTGCCAA AAAGCTGTAA
 301  CTTGACGGCT GCCCTGTCCT TCCTAGATAA TGGCACCAAA TTCTCCTGAG
 351  GCTAGGGGGG AAGGAGTGTC AGAGTGTCAC TAGCTCGACC CTGGGGACAA
 401  GGGGGACTAA TAGTACCCTA GCTTGATTTC TTCCTATTCT CAAGTTCCTT
 451  TTTATTTCTC CCTTGCGTAA CCCGCTCTTC CCTTCTGTGC CTTTGCCTGT
 501  ATTCCCACCC TCCCTGCTAC CTCTTGGCCA CCTCACTTCT GAGACCACAG
 551  CTGTTGGCAG GGTCCCTAGC TCATGCCAGC CTCATCTCCA GGCCACATGG
 601  GGGGCTCAGT CAGAGAGCCA GCCCTTTCGG TTGCTCTTTG GTTGAGTTGG
 651  GGGGCAGTTC TGGGGGCTGT GACTTGTGCT GTCGCACTAC TGATCCAACA
 701  GACAGAGCTG CAAAGCCTAA GGCGGGAGGT GAGCCGGCTG CAGCGGAGTG
 751  GAGGGCCTTC CCAGAAGCAG GGAGAGCGCC CATGGCAGAG CCTCTGGGAG
 801  CAGAGTCCTG ATGTCCTGGA AGCCTGGAAG GATGGGGCGA AATCTCGGAG
 851  AAGGAGAGCA GTACTCACCC AGAAGCACAA GAAGAAGCAC TCAGTCCTGC
 901  ATCTTGTTCC AGTTAACATT ACCTCCAAGG ACTCTGACGT GACAGAGGTG
 951  ATGTGGCAAC CAGTACTTAG GCGTGGGAGA GGCCTGGAGG CCCAGGGAGA
1001  CATTGTACGA GTCTGGGACA CTGGAATTTA TCTGCTCTAT AGTCAGGTCC
1051  TGTTTCATGA TGTGACTTTC ACAATGGGTC AGGTGGTATC TCGGGAAGGA
1101  CAAGGGAGAA GAGAAACTCT ATTCCGATGT ATCAGAAGTA TGCCTTCTGA
1151  TCCTGACCGT GCCTACAATA GCTGCTACAG TGCAGGTGTC TTTCATTTAC
1201  ATCAAGGGGA TATTATCACT GTCAAAATTC CACGGGCAAA CGCAAAACTT
1251  AGCCTTTCTC CGCATGGAAC ATTCCTGGGG TTTGTGAAAC TATGATTGTT
1301  ATAAAGGGGG TGGGGATTTC CCATTCCAAA AACTGGCTAG ACAAAGGACA
1351  AGGAACGGTC AAGAACAGCT CTCCATGGCT TTGCCTTGAC TGTTGTTCCT
1401  CCCTTTGCCT TTCCCGCTCC CACTATCTGG GCTTTGACTC CATGGATATT
1451  AAAAAGTAG AATATTTTGT GTTTATCTCC CAAAAA
```

FIG. 2B

Mouse G70  Length: 241 (SEQ ID NO 4)

```
  1  MPASSPGHMG GSVREPALSV ALWLSWGAVL GAVTCAVALL IQQTELQSLR
 51  REVSRLQRSG GPSQKQGERP WQSLWEQSPD VLEAWKDGAK SRRRRAVLTQ
101  KHKKKHSVLH LVPVNITSKD SDVTEVMWQP VLRRGRGLEA QGDIVRVWDT
151  GIYLLYSQVL FHDVTFTMGQ VVSREGQGRR ETLFRCIRSM PSDPDRAYNS
201  CYSAGVFHLH QGDIITVKIP RANAKLSLSP HGTFLGFVKL *
```

G-70 FLAG des92 (smuG70) Strain #4081 (SEQ ID NO 19):

```
MDYKDDDDKKHKKKHSVLHLVPVNITSKDSDVTEVMWQPVLRRGRGLEAQGDIVRVWDTGIY
LLYSQVLFHDVTFTMGQVVSREGQGRRETLFRCIRSMPSDPDRAYNSCYSAGVFHLHQGDII
TVKIPRANAKLSLSPHGTFLGFVKL*
```

FIG. 3

Alignm. of human and mouse G70

```
mouse:   1  MPASS---------PGHMGGSVREPALSVALWLSWGAVLGAVTCAVALLTQQTELQSLRR  51
            MPASS         PG+MGG VREPALSVALWLSWGA LGAV CA+ALL QQTELQSLRR
human:   1  MPASSPFLLAPKGPPGNMGGPVREPALSVALWLSWGAALGAVACAMALLTQQTELQSLRR  60 mouse:  52  EVSRLQRSGGPSQKQGERPWQSLWEQSPDVLEAWKDGAKSRRRRAVLTQKHKKKHSVLHL  111
            EVSRLQ +GGPSQ        PWQSL EQS D LEAW+ G  +SR+RRAVLTQK KK+HSVLHL
human:  61  EVSRLQGTGGPSQNGEGYPWQSLPEQSSDALEAWESGERSRKRRAVLTQKQKKQHSVLHL  120 mouse: 112  VPVNITSKD-SDVTEVMWQPVLRRGRGLEAQGDIVRVWDTGIYLLYSQVLFHDVTFTMGQ  170
            VP+N TSKD SDVTEVMWQP LRRGRGL+AQG  VR+ D G+YLLYSQVLF DVTFTMGQ
human: 121  VPINATSKDDSDVTEVMWQPALRRGRGLQAQGYGVRIQDAGVYLLYSQVLFQDVTFTMGQ  180 mouse: 171  VVSREGQGRRETLFRCIRSMPSDPDRAYNSCYSAGVFHLHQGDIITVKIPRANAKLSLSP  230
            VVSREGQGR+ETLFRCIRSMPS PDRAYNSCYSAGVFHLHQGDI++V IPRA AKL+LSP
human: 181  VVSREGQGRQETLFRCIRSMPSHPDRAYNSCYSAGVFHLHQGDILSVIIPRARAKLNLSP  240 mouse: 231  HGTFLGFVKL  240
            HGTFLGFVKL
human: 241  HGTFLGFVKL  250
```

FIG. 4A
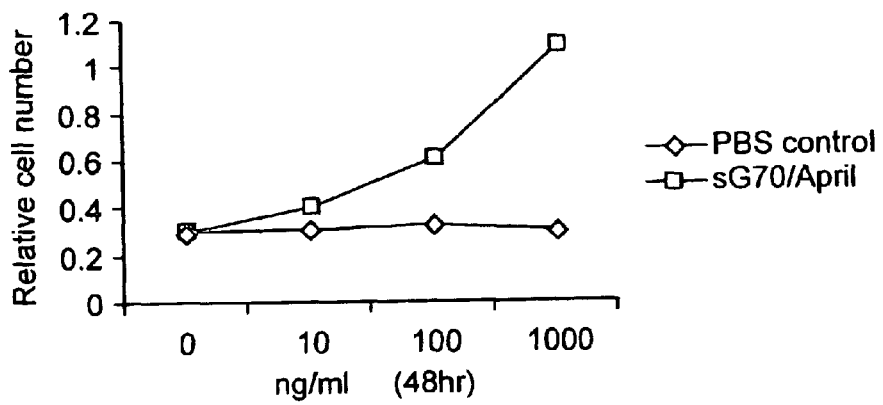
Effect of sG70/April on Raji cell proliferation
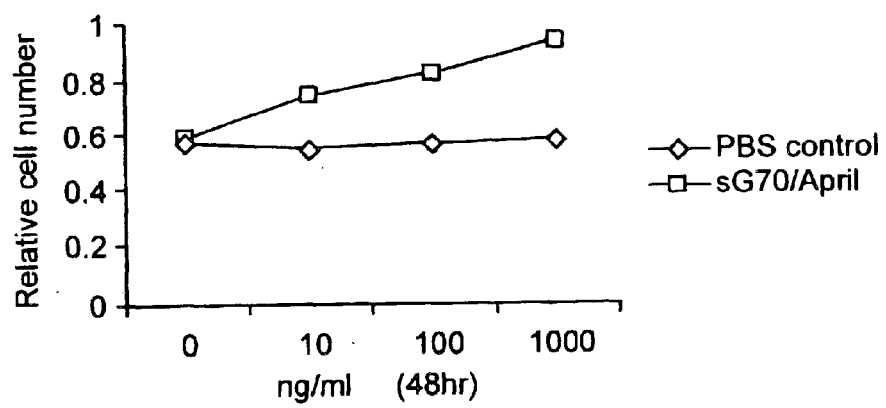
Effect of sG70/April on Jurkat cell proliferation
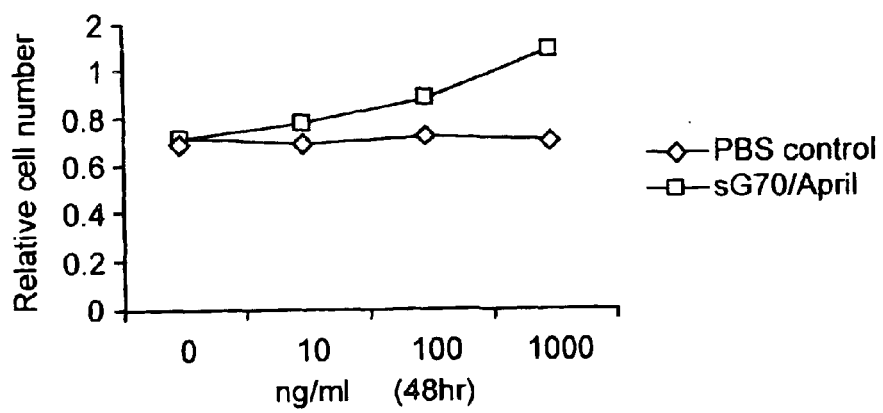
Effect of sG70/April on K562 cell proliferation

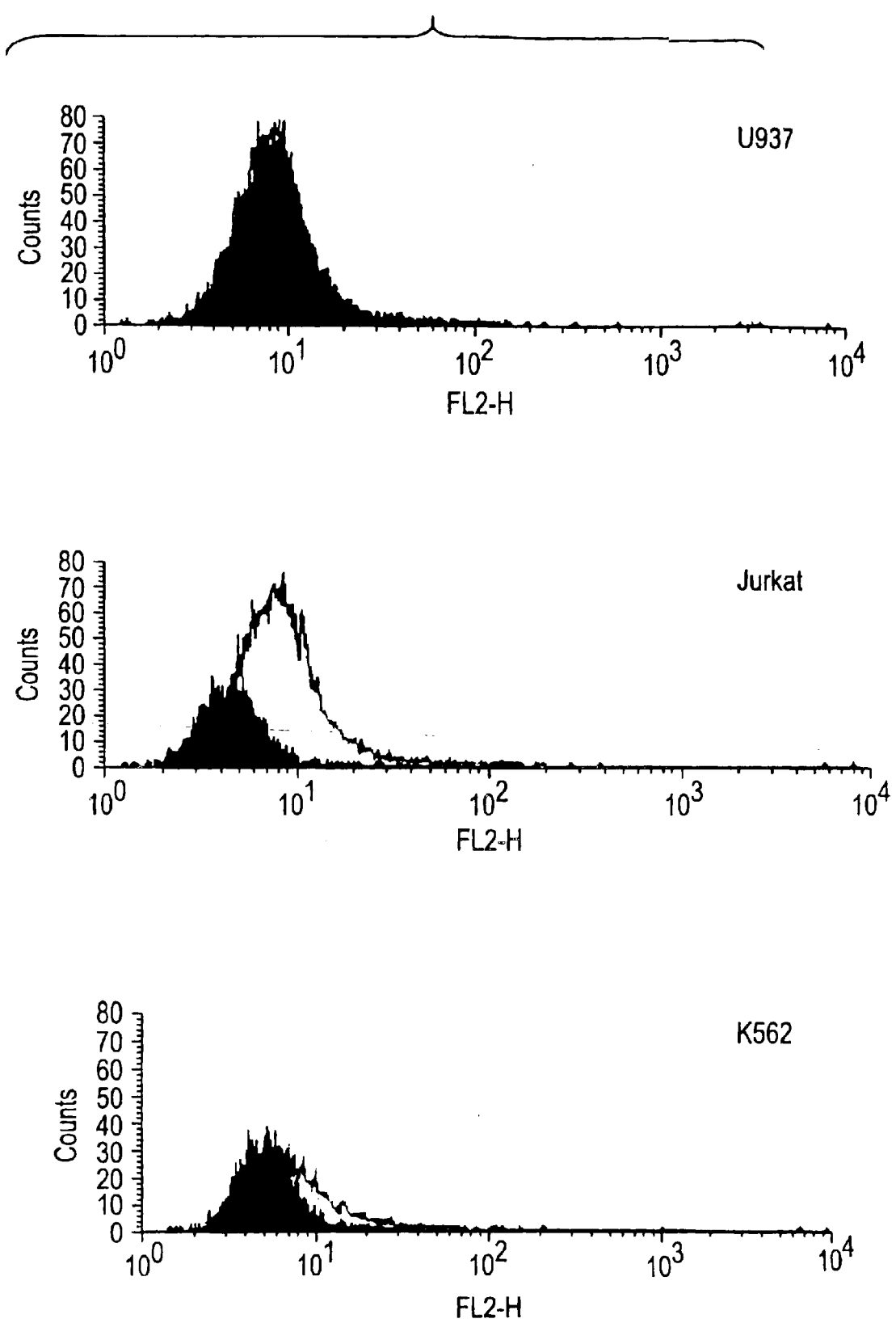

FIG. 6
The effect of r-G70/April on human peripheral blood B cell, T cell and Granucolyte
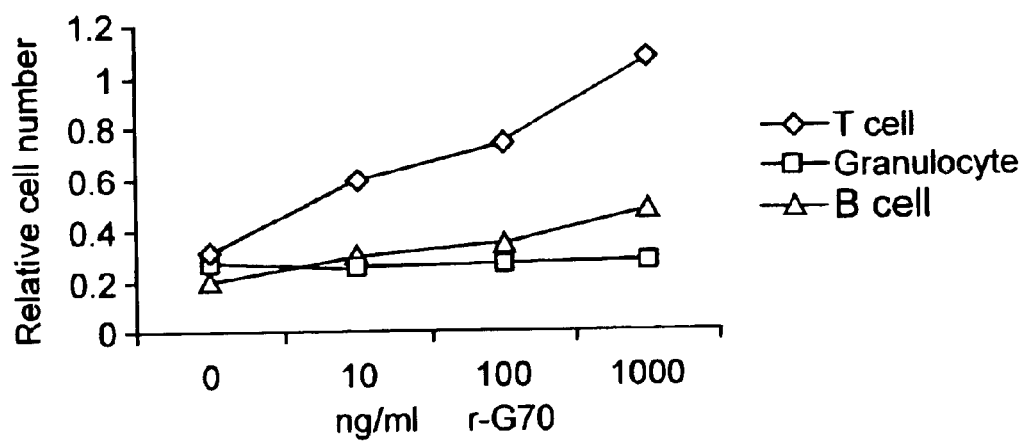
The effect of IL-2 and G70/April on human peripheral T cell proliferation
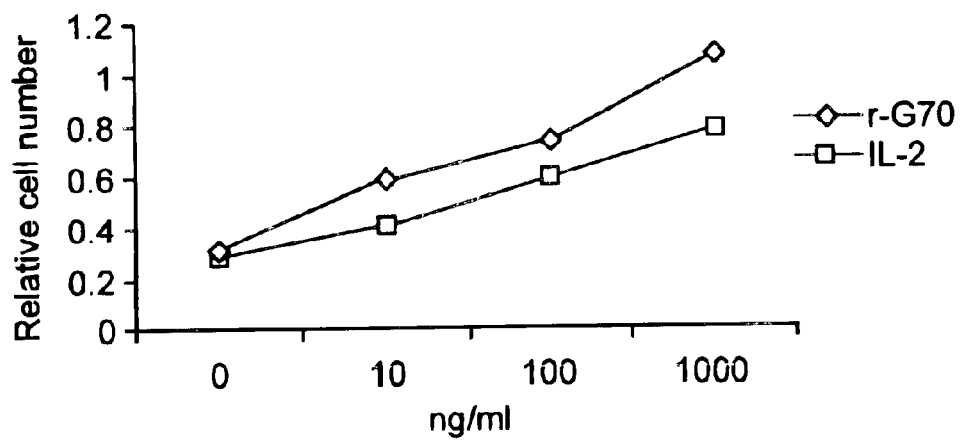

FIG. 7
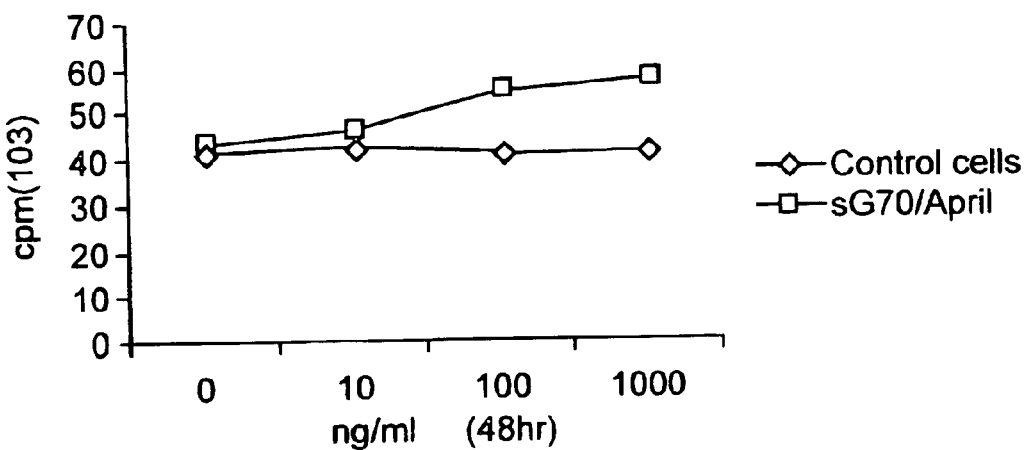
Effect of sG70/April on murine B cell proliferation
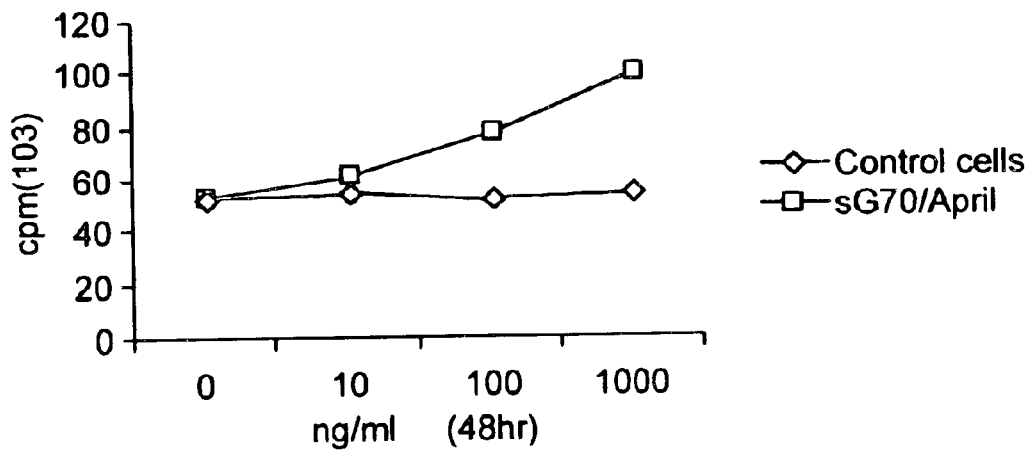
Effect of sG70/April on murine T cell proliferation Effect of G70/April on murine T cell proliferation costimulated through CD28 antibody Co-stimulatory activity of G70/April on mouse T cells

FIG. 10A

Human BCMA

Human (SEQ ID NO: 5):

1 MAGQCSQNEY FDSLLHACIP CQLRCSSNTP PLTCQRYCNA SVTNSVKGTN

51 AILWTCLGLS LIISLAVFVL MFLLRKISSE PLKDEFKNTG SGLLGMANID

101 LEKSRTGDEI ILPRGLEYTV EECTCEDCIK SKPKVDSDHC FPLPAMEEGA

151 TILVTTKTND YCKSLPAALS ATEIEKSISA R

Human (SEQ ID NO: 5):

MAGQCSQ NEYFDSLLHA CIPCQLRCSS NTPPLTCQRY CNASVTNSVK

GTNA <u>ILWTCL GLSLIISLAV FVLMF</u>LLRKI SSEPLKDEFK NTGSGLLGMA

NIDLEKSRTG DEIILPRGLE YTVEECTCED CIKSKPKVDS DHCFPLPAME

EGATILVTTK TNDYCKSLPA ALSATEIEKS ISAR hBCMA's extracellular domain (SEQ ID NO: 6):

MAGQCSQ NEYFDSLLHA CIPCQLRCSS NTPPLTCQRY CNASVTNSVK

GTNA hBCMA's cysteine-rich consensus region (SEQ ID NO: 7):

CSQ NEYFDSLLHA CIPCQLRCSS NTPPLTCQRY C hBCMA's transmembrane region (SEQ ID NO: 8):

ILWTCL GLSLIISLAV FVLMF

FIG. 10B huBCMA-Fc (SEQ ID NO: 9):

MAGQCSQNEYFDSLLHACIPCQLRCSSNTPPLTCQRYCNASVTNSVKGTNAGGG
GGDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKS
LSLSPGK* muBCMA-Fc (SEQ ID NO: 10):

MAQQCFHSEYFDSLLHACKPCHLRCSNPPATCQPYCDPSVTSSVKGSYTGGGGG
DKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLS
LSPGK*

FIG. 11

Alignment of human BCMA amino acid sequence and murine BCMA amino acid sequence murine BCMA amino acid sequence Length: 185 (SEQ ID NO: 11):

```
  1 MAQQCFHSEY FDSLLHACKP CHLRCSNPPA TCQPYCDPSV TSSVKGTYTV
 51 LWIFLGLTLV LSLALFTISF LLRKMNPEAL KDEPQSPGQL DGSAQLDKAD
101 TELTRIRAGD DRIFPRSLEY TVEECTCEDC VKSKPKGDSD HFFPLPAMEE
151 GATILVTTKT GDYGKSSVPT ALQSVMGMEK PTHTR
``` alignment of human BCMA amino acid sequence and murine BCMA amino acid sequence.

```
Query:   4 MAGQCSQNEYFDSLLHACIPCQLRCSSNTPPLTCQRYCNASVTNSVKGTNAILWTCLGLS  63
           MA QC  +EYFDSLLHAC PC LRCS+   PP TCQ YC+ SVT+SVKGT  +LW  LGL+
Sbjct:   1 MAQQCFHSEYFDSLLHACKPCHLRCSN--PPATCQPYCDPSVTSSVKGTYTVLWIFLGLT  58

Query:  64 LIISLAVFVLMFLLRKISSEPLKDEFKNTG----SGLLGMANIDLEKSRTGDEIILPRGL 119
           L++SLA+F + FLLRK++ E LKDE ++ G    S  L A+ +L + R GD+ I PR L
Sbjct:  59 LVLSLALFTISFLLRKMNPEALKDEPQSPGQLDGSAQLDKADTELTRIRAGDDRIFPRSL 118

Query: 120 EYTVEECTCEDCIKSKPKVDSDHCFPLPAMEEGATILVTTKTNDYCKS-LPAAL-SATEI 177
           EYTVEECTCEDC+KSKPK DSDH FPLPAMEEGATILVTTKT DY KS +P AL S   +
Sbjct: 119 EYTVEECTCEDCVKSKPKGDSDHFFPLPAMEEGATILVTTKTGDYGKSSVPTALQSVMGM 178

Query: 178 EKSISAR 184
           EK    R
Sbjct: 179 EKPTHTR 185
```

FIG. 12A

Human TACI huTACI (SEQ ID NO: 14).

```
  1 MSGLGRSRRG GRSRVDQEER FPQGLWTGVA MRSCPEEQYW DPLLGTCMSC
 51 KTICNHQSQR TCAAFCRSLS CRKEQGKFYD HLLRDCISCA SICGQHPKQC
101 AYFCENKLRS PVNLPPELRR QRSGEVENNS DNSGRYQGLE HRGSEASPAL
151 PGLKLSADQV ALVYSTLGLC LCAVLCCFLV AVACFLKKRG DPCSCQPRSR
201 PRQSPAKSSQ DHAMEAGSPV STSPEPVETC SFCFPECRAP TQESAVTPGT
251 PDPTCAGRWG CHTRTTVLQP CPHIPDSGLG IVCVPAQEGG PGA
```

MSGLGRSRRGGRSRVDQEERFPQGLWTGVAMRSCPEEQYWDPLLGTCMSC
KTICNHQSQRTCAAFCRSLSCRKEQGKFYDHLLRDCISCASICGQHPKQC
AYFCENKLRSPVNLPPELRRQRSGEVENNSDNSGRYQGLEHRGSEASPAL
PGLKLSADQVALVYST<u>LGLCLCAVLCCFLVAVACFL</u>KKRGDPCSCQPRSR
PRQSPAKSSQDHAMEAGSPVSTSPEPVETCSFCFPECRAPTQESAVTPGT
PDPTCAGRWGCHTRTTVLQPCPHIPDSGLGIVCVPAQEGGPGA huTACI's extracellular domain (SEQ ID NO: 15):

```
  1 MSGLGRSRRG GRSRVDQEER FPQGLWTGVA MRSCPEEQYW DPLLGTCMSC
 51 KTICNHQSQR TCAAFCRSLS CRKEQGKFYD HLLRDCISCA SICGQHPKQC
101 AYFCENKLRS PVNLPPELRR QRSGEVENNS DNSGRYQGLE HRGSEASPAL
151 PGLKLSADQV ALVYST
```

FIG. 12B huTACI's cysteine-rich consensus region (SEQ ID NO: 16):
CPEEQYWDPLLGTCMSCKTICNHQSQRTCAAFC and
CRKEQGKFYDHLLRDCISCASICGQHPKQCAYFC transmembrane region (SEQ ID NO: 17):
LGLCLCAVLCCFLVAVACFL hTACI-Fc (SEQ ID NO: 18):

```
  1  MSGLGRSRRG GRSRVDQEER FPQGLWTGVA MRSCPEEQYW DPLLGTCMSC

51  KTICNHQSQR TCAAFCRSLS CRKEQGKFYD HLLRDCISCA SICGQHPKQC

101  AYFCENKLRS PVNLPPELRR QRSGEVENNS DNSGRYQGLE HRGSEASPAL

151  PGLKLSADQV ALVYSGGGGG DKTHTCPPCP APELLGGPSV FLFPPKPKDT

201  LMISRTPEVT CVVVDVSHED PEVKFNWYVD GVEVHNAKTK PREEQYNSTY

251  RVVSVLTVLH QDWLNGKEYK CKVSNKALPA PIEKTISKAK GQPREPQVYT

301  LPPSRDELTK NQVSLTCLVK GFYPSDIAVE WESNGQPENN YKTTPPVLDS

351  DGSFFLYSKL TVDKSRWQQG NVFSCSVMHE ALHNHYTQKS LSLSPGK*
```

FIG. 13

Alignment of cysteine rich extracellular regions of human TACI and human BCMA.

```
34 CPEEQYWDPLLGTCMSCKTICNHQS.QRTCAAFCRSLSCRKEQGKFYDHL 82
   | : :|.| ||  |. |.  |.  .  || :| .    .|  . :
 8 CSQNEYFDSLLHACIPCQLRCSSNTPPLTCQRYCNASVTNSVKGT..NAI 55

83 LRDCISCASI 92
           |  |:  . |
        56 LWTCLGLSLI 65
```

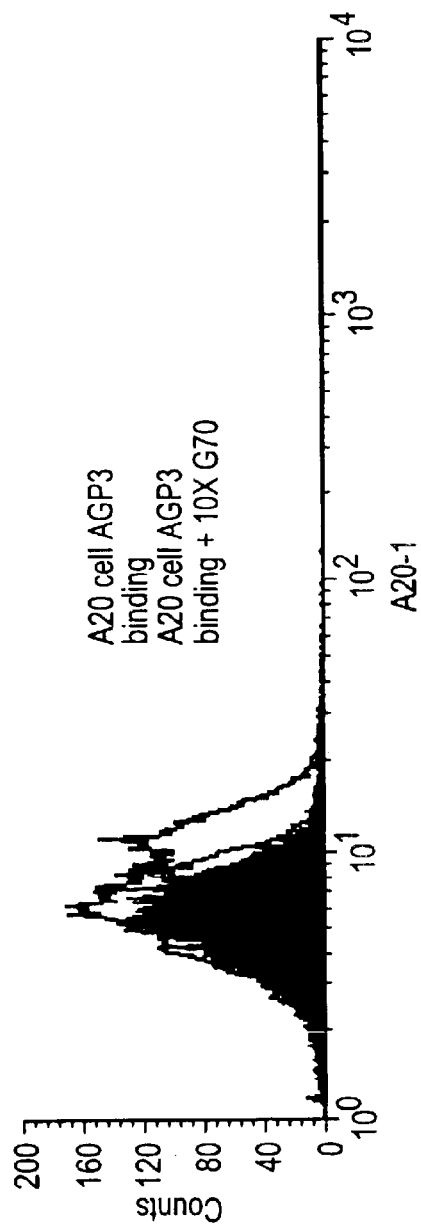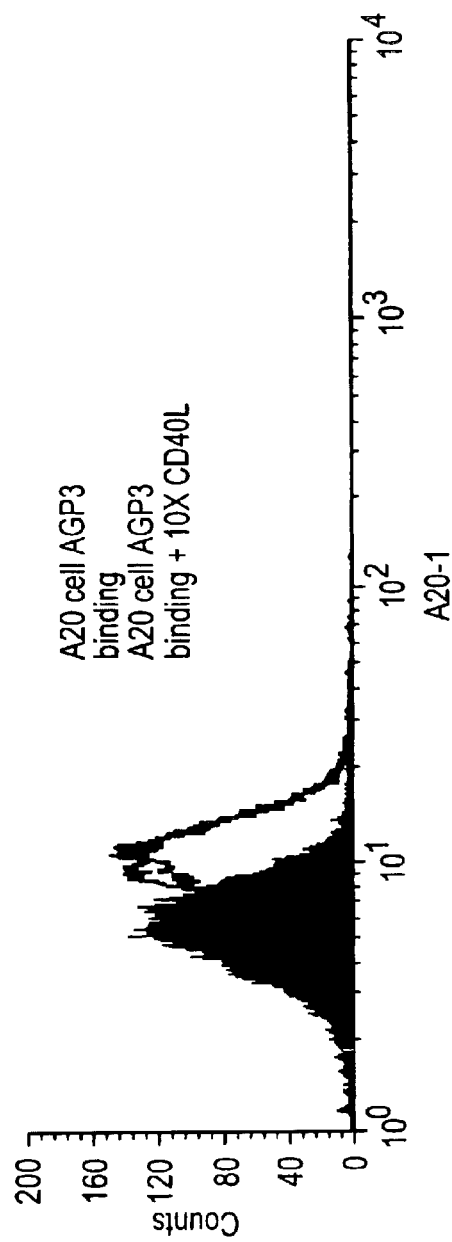

FIG. 21

Fc-humanAPRIL

Fc-humanAPRIL protein sequence including the signal sequence, Fc domain, linker (XhoI site) and APRIL:

```
  1  MEWSWVFLFF LSVTTGVHSD KTHTCPPCPA PELLGGPSVF
     LFPPKPKDTL
 51  MISRTPEVTC VVVDVSHEDP EVKFNWYVDG VEVHNAKTKP
     REEQYNSTYR
101  VVSVLTVLHQ DWLNGKEYKC KVSNKALPAP IEKTISKAKG
     QPREPQVYTL
151  PPSRDELTKN QVSLTCLVKG FYPSDIAVEW ESNGQPENNY
     KTTPPVLDSD
201  GSFFLYSKLT VDKSRWQQGN VFSCSVMHEA LHNHYTQKSL
     SLSPGK SRAV
251  LTQKQKKQHS VLHLVPINAT SKDDSDVTEV MWQPALRRGR
     GLQAQGYGVR
301  IQDAGVYLLY SQVLFQDVTF TMGQVVSREG QGRQETLFRC
     IRSMPSHPDR
351  AYNSCYSAGV FHLHQGDILS VIIPRARAKL NLSPHGTFLG
     FVKL*
```

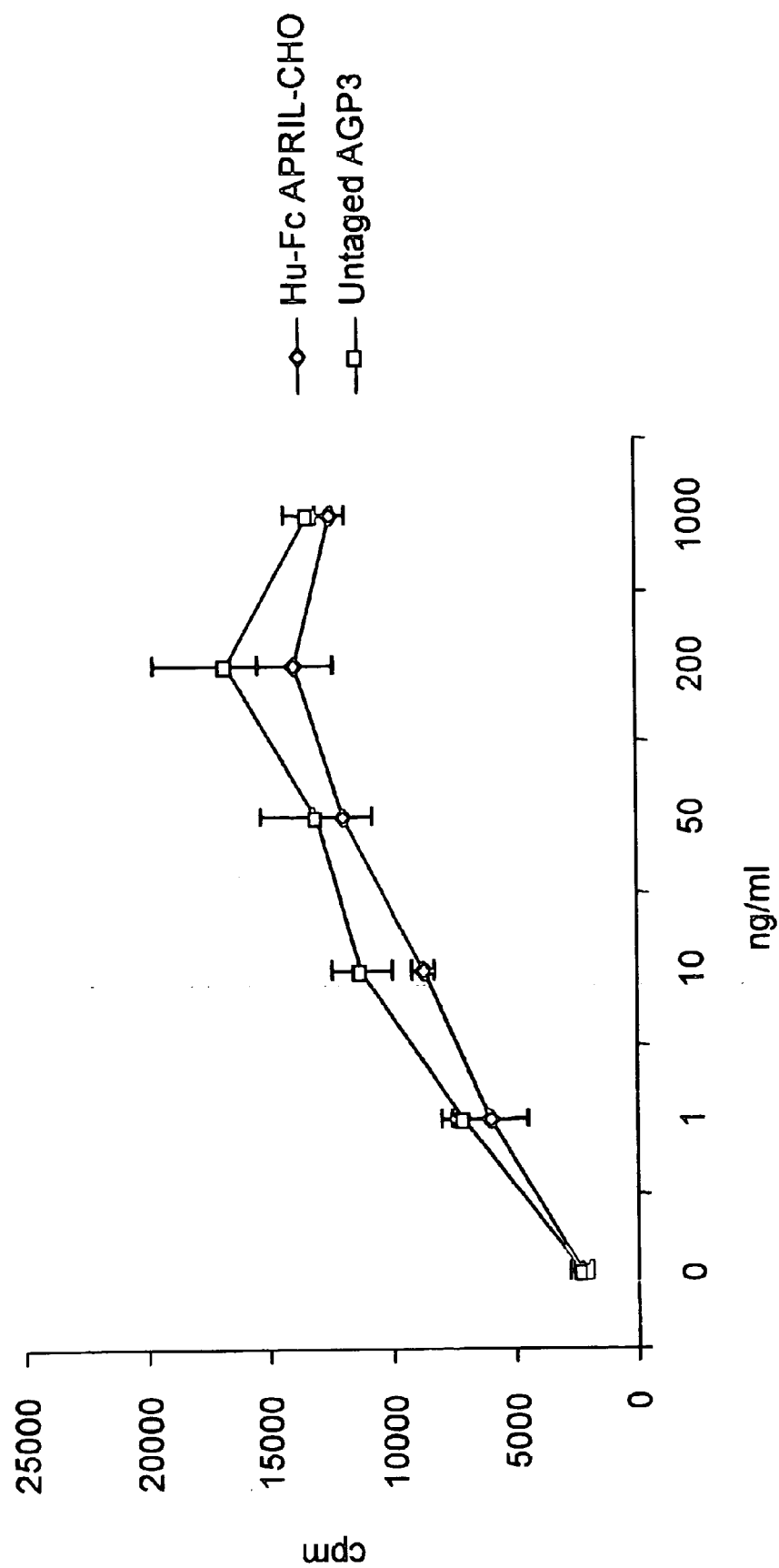

hBCMA-Fc and wt hTACI-Fc inhibits Flag-mAPRIL mediated mouse B cell proliferation

FIG. 24 hBCMA-Fc reduces PB B cell level in vivo
*15 mg/kg ip on day 0, 3, and 6*

| BLOOD | | WBC 10e6/ml | #Lym 10e6/ml | CD3+ # | CD3-B220+ # |
|---|---|---|---|---|---|
| BCMA-Fc | SD t test | 5.30 0.39 0.03318 | 3.81 0.43 0.01570 | 2.3 0.32 0.24737 | 1.3 0.27 0.00506 |
| Fc | SD | 8.02 1.27 | 6.43 1.52 | 2.7 0.6 | 3.2 0.6 |
| Saline | SD | 6.90 2.04 | 5.55 1.79 | 2.1 0.5 | 2.9 1.2 |

FIG. 25

**hBCMA-Fc reduces spleen B cell levels *in vivo***
*15 mg/kg ip on day 0, 3, and 6*

| Spleen | | WBC 10e6/ml | Lym (%) | spleen lym# 10ml(x10e6) | CD3-B220+ (%) | CD3-B220+ # |
|---|---|---|---|---|---|---|
| BCMA-Fc | | 9.12 | 97.9 | 89.3 | 45.5 | 41.8 |
| | SD | 0.92 | 0.51 | 9.32 | 1.29 | 4.92 |
| | t test | 0.02778 | 0.89118 | 0.02668 | 0.00234 | 0.02088 |
| Fc | | 11.49 | 97.9 | 112.5 | 50.6 | 57.1 |
| | SD | 1.62 | 0.38 | 15.65 | 1.95 | 9.67 |
| Saline | | 11.48 | 98.5 | 113.1 | 53.7 | 48.5 |
| | SD | 1.71 | 0.1 | 16.9 | 6.7 | 29.15 |

FIG. 26
Flag-mAPRIL and hAGP3 mediated IgA production
inhibited by hBCMA-Fc and hTACI-Fc *in vitro*
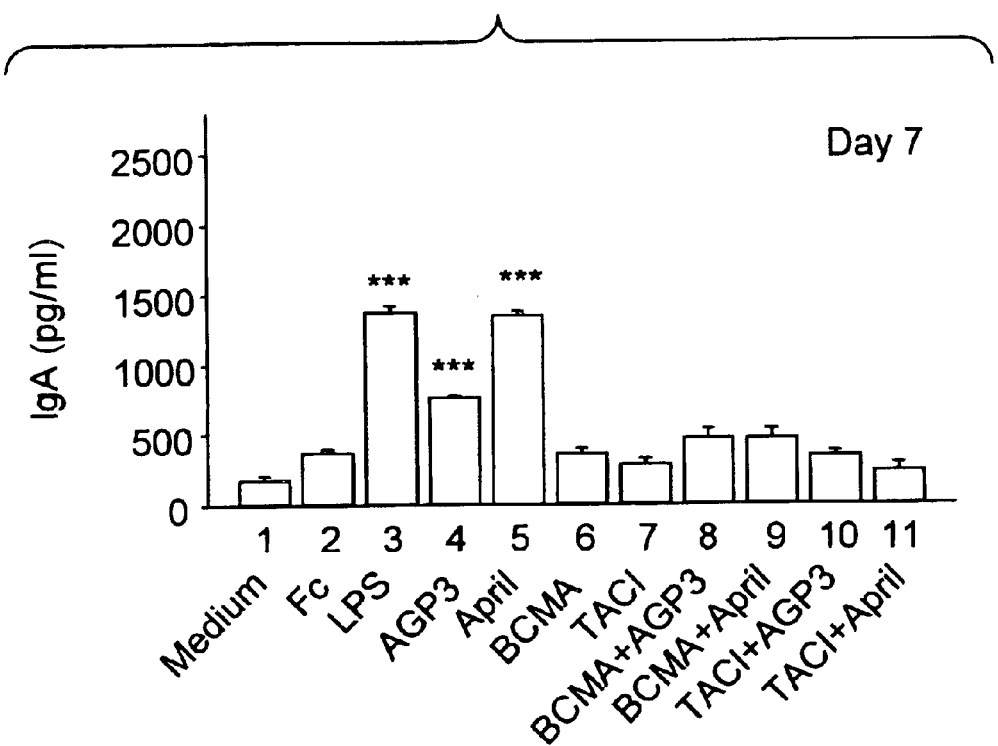
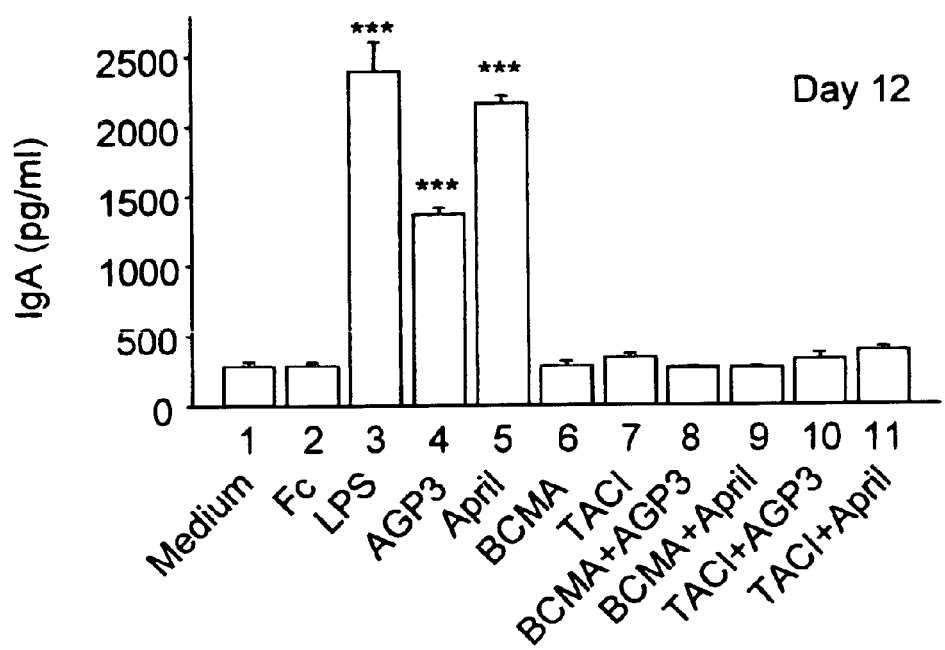

FIG. 27
Flag-mAPRIL and hAGP3 Mediated IgG Production Inhibited by BCMA-Fc and TACI-Fc *in Vitro*
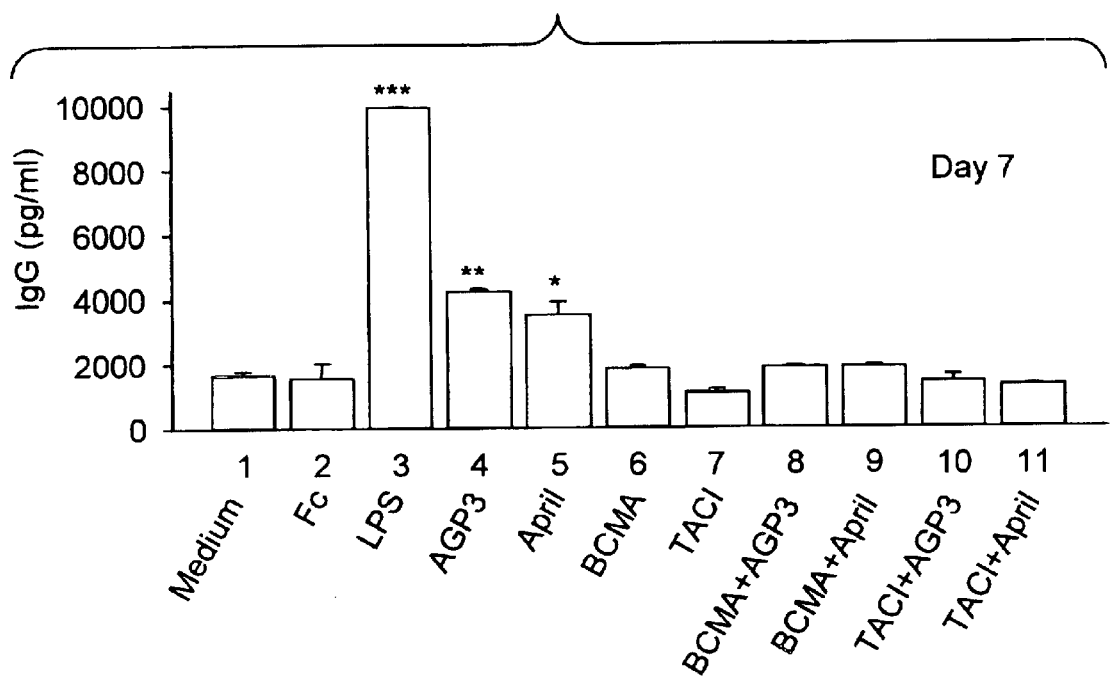
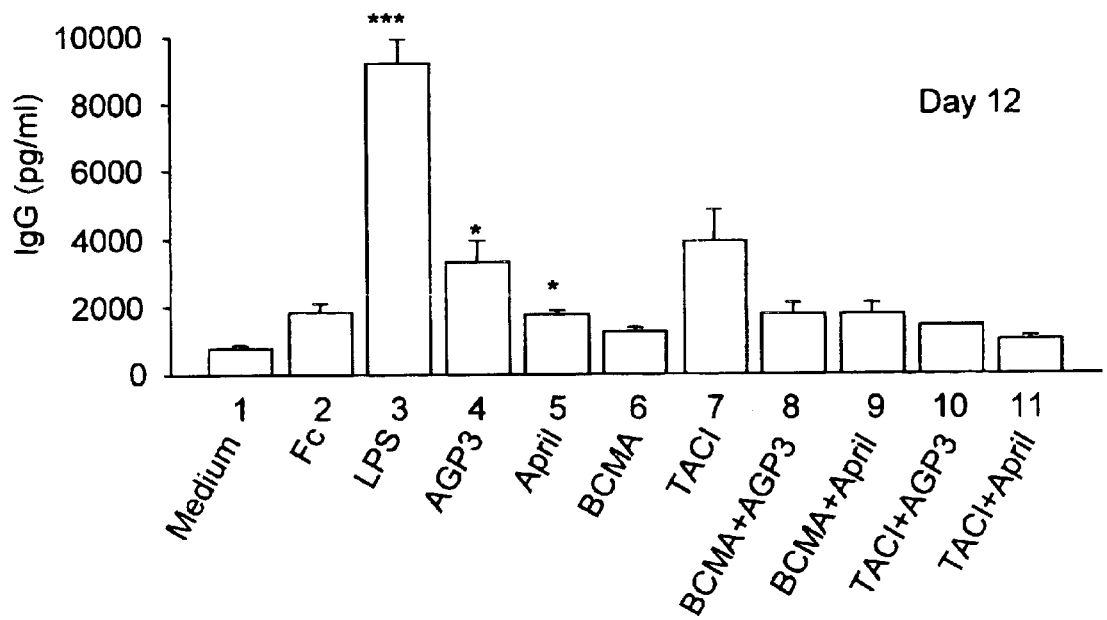

Significantly reduces total IgE and IgA in normal mice treated with mBCMA-Fc and trun hTACI-Fc 5 mg/kg ip day 0, 3, and 6

BCMA-Fc and truncated TACI-Fc at daily doses of 0.5 mg/kg inhibits humoral immunity *in vivo*

FIG. 34

Analysis of antibodies to dsDNA from the peripheral blood from various treatment groups of BWF1 at day 0, 30, 60, and 90.

MEAN anti-dsDNA isotypes in U/ml

| Group # | Day 0 IgG | Day 0 IgM | Day 30 IgG | Day 30 IgM | Day 60 IgG | Day 60 IgM | Day 90 IgG | Day 90 IgM |
|---|---|---|---|---|---|---|---|---|
| hBCMA-300 | 179 | 560 | 163 | 371 | 150 | 706 | 171 | 841 |
| hBCMA-100 | 150 | 430 | 259 | 718 | 171 | 822 | 339 | 1031 |
| hBCMA-30 | 377 | 592 | 297 | 458 | 401 | 664 | 424 | 601 |
| FC. | 149 | 371 | 234 | 283 | 384 | 331 | 432 | 351 |
| PBS | 308 | 292 | 439 | 311 | 247 | 576 | 720 | 467 |

Standard Deviation of the above means

| Group # | Day 0 IgG | Day 0 IgM | Day 30 IgG | Day 30 IgM | Day 60 IgG | Day 60 IgM | Day 90 IgG | Day 90 IgM |
|---|---|---|---|---|---|---|---|---|
| hBCMA-300 | 104 | 303 | 116 | 211 | 62 | 518 | 62 | 734 |
| hBCMA-100 | 109 | 262 | 306 | 461 | 212 | 758 | 371 | 1225 |
| hBCMA-30 | 363 | 455 | 281 | 430 | 305 | 606 | 421 | 400 |
| FC. | 68 | 160 | 150 | 93 | 391 | 151 | 233 | 237 |
| PBS | 311 | 73 | 474 | 152 | 247 | 370 | 870 | 327 |

FIG. 35

Evaluation of B cell numbers at treatment day 60 from the 12mg/kg (30 ug), 4mg/kg (100ug), and 1.3mg/kg (300 ug) dose of hBCMA-Fc groups along with the Fc and PBS control groups.

| hBCMA-fc-300 | | | | hBCMA-100 | | | | hBCMA-FC-30 | | | |
|---|---|---|---|---|---|---|---|---|---|---|---|
| Mouse# | %CD4 | %CD8 | %B220 | | %CD4 | %CD8 | %B220 | | %CD4 | %CD8 | %B220 |
| 1.0 | 16.3 | 11.0 | 16.4 | 5.0 | 26.1 | 14.9 | 10.1 | 9.0 | 2.5 | 6.9 | 10.3 |
| 2.0 | 24.1 | 11.1 | 11.6 | 6.0 | 21.1 | 11.3 | 10.6 | 10.0 | 13.2 | 5.2 | 23.4 |
| 3.0 | 18.2 | 7.4 | 9.9 | 7.0 | 24.6 | 13.3 | 8.3 | 11.0 | 15.9 | 6.4 | 29.2 |
| 4.0 | 25.4 | 13.3 | 13.1 | 8.0 | 20.0 | 11.3 | 13.4 | 12.0 | 14.8 | 7.6 | 31.5 |
| x | 21.0 | 10.7 | 12.8 | x | 23.0 | 12.7 | 10.6 | x | 11.6 | 6.5 | 23.6 |
| sd | 4.4 | 2.4 | 2.8 | sd | 2.9 | 1.7 | 2.1 | sd | 6.2 | 1.0 | 9.5 |

| Fc | | | | PBS | | | |
|---|---|---|---|---|---|---|---|
| 33.0 | 7.0 | 8.1 | 25.4 | 37.0 | 16.9 | 8.3 | 15.5 |
| 34.0 | 10.7 | 4.9 | 15.3 | 38.0 | 19.1 | 12.1 | 19.5 |
| 35.0 | 18.9 | 9.3 | 21.0 | 39.0 | 7.1 | 3.4 | 17.5 |
| 36.0 | 20.1 | 11.1 | 21.0 | 40.0 | 19.9 | 11.4 | 26.5 |
| x | 14.2 | 8.4 | 20.7 | x | 15.8 | 8.8 | 19.8 |
| sd | 6.4 | 2.6 | 4.1 | sd | 5.9 | 4.0 | 4.8 |

FIG. 36

Specific APRIL binding to Human Cell lines determined by FACS analysis

| | APRIL binding |
|---|---|
| HT 29 Colon adenocarcinoma | +++ |
| NCI 460 Lung carcinoma | +++ |
| PC3 Prostate adenocarcinoma | ++ |
| C6 Glial carcinoma | ++ |
| Raji Burkitt lymphoma | +++ |
| A20 Mouse B cell lymphoma | +++ |
| U266BI Myeloma | +++ |
| A435 Epidermoid carcinoma | -- |
| A469 Kidney carcinoma | -- |
| MDA-231 breast adenocarcinoma | -- |

Effects of BCMA & hTACI on the Growth of A20 in Balb/c Mice

EFFECT OF MURINE BCMA-Fc AGAINST HT-29 SC TUMOR GROWTH
Rx: IP, Q2D, day 0

Linear growth ANOVA with Dunnett's correction for multiple testing (n=10/group)

SEQUENCE LISTING

<160> NUMBER OF SEQ ID NOS: 31

<210> SEQ ID NO 1
<211> LENGTH: 1465
<212> TYPE: DNA
<213> ORGANISM: Homo sapiens

<400> SEQUENCE: 1

```
gccaaccttc cctcccccaa ccctggggcc gccccagggt tcctgcgcac tgcctgttcc      60
tcctgggtgt cactggcagc cctgtccttc ctagagggac tggaacctaa ttctcctgag     120
gctgagggag ggtggaggt ctcaaggcaa cgctggcccc acgacggagt gccaggagca     180
ctaacagtac ccttagcttg ctttcctcct ccctcctttt tattttcaag ttccttttta     240
tttctccttg cgtaacaacc ttcttcctt ctgcaccact gcccgtaccc ttacccgccc     300
cgccacctcc ttgctacccc actcttgaaa ccacagctgt tggcagggtc cccagctcat     360
gccagcctca tctcctttct tgctagcccc caaagggcct ccaggcaaca tggggggccc     420
agtcagagag ccggcactct cagttgccct ctggttgagt tgggggggcag ctctggggc     480 cgtggcttgt gccatggctc tgctgaccca acaaacagag ctgcagagcc tcaggagaga     540
ggtgagccgg ctgcagggga caggaggccc ctcccagaat ggggaagggt atccctggca     600
gagtctcccg gagcagagtt ccgatgccct ggaagcctgg gagagtgggg agagatcccg     660
gaaaaggaga gcagtgctca cccaaaaaca gaagaagcag cactctgtcc tgcacctggt     720
tcccattaac gccacctcca aggatgactc cgatgtgaca gaggtgatgt ggcaaccagc     780
tcttaggcgt gggagaggcc tacaggccca aggatatggt gtccgaatcc aggatgctgg     840
agtttatctg ctgtatagcc aggtcctgtt tcaagacgtg actttcacca tgggtcaggt     900
ggtgtctcga gaaggccaag gaaggcagga gactctattc cgatgtataa gaagtatgcc     960
ctcccacccg gaccgggcct acaacagctg ctatagcgca ggtgtcttcc atttacacca    1020
agggdatatt ctgagtgtca taattcccg ggcaagggcg aaacttaacc tctctccaca    1080
tggaaccttc ctggggtttg tgaaactgtg attgtgttat aaaaagtggc tcccagcttg    1140
gaagaccagg gtgggtacat actggagaca gccaagagct gagtatataa aggagaggga    1200
atgtgcagga acagaggcgt cttcctgggt ttggctcccc gttcctcact tttcccttt    1260 cattcccacc ccctagactt tgattttacg gatatcttgc ttctgttccc catggagctc    1320
```

```
cgaattcttg cgtgtgtgta gatgaggggc gggggacggg cgccaggcat tgttcagacc   1380
tggtcggggc ccactggaag catccagaac agcaccacca tctaacggcc gctcgaggga   1440
agcacccggc ggtttgggcg aagtc                                        1465

<210> SEQ ID NO 2
<211> LENGTH: 233
<212> TYPE: PRT
<213> ORGANISM: Homo sapiens

<400> SEQUENCE: 2

Met Gly Gly Pro Val Arg Glu Pro Ala Leu Ser Val Ala Leu Trp Leu
1               5                   10                  15

Ser Trp Gly Ala Ala Leu Gly Ala Val Ala Cys Ala Met Ala Leu Leu
            20                  25                  30

Thr Gln Gln Thr Glu Leu Gln Ser Leu Arg Arg Glu Val Ser Arg Leu
        35                  40                  45

Gln Gly Thr Gly Gly Pro Ser Gln Asn Gly Glu Gly Tyr Pro Trp Gln
    50                  55                  60

Ser Leu Pro Glu Gln Ser Ser Asp Ala Leu Glu Ala Trp Glu Ser Gly
65                  70                  75                  80

Glu Arg Ser Arg Lys Arg Arg Ala Val Leu Thr Gln Lys Gln Lys Lys
                85                  90                  95

Gln His Ser Val Leu His Leu Val Pro Ile Asn Ala Thr Ser Lys Asp
            100                 105                 110

Asp Ser Asp Val Thr Glu Val Met Trp Gln Pro Ala Leu Arg Arg Gly
        115                 120                 125

Arg Gly Leu Gln Ala Gln Gly Tyr Gly Val Arg Ile Gln Asp Ala Gly
    130                 135                 140

Val Tyr Leu Leu Tyr Ser Gln Val Leu Phe Gln Asp Val Thr Phe Thr
145                 150                 155                 160

Met Gly Gln Val Val Ser Arg Glu Gly Gln Gly Arg Gln Glu Thr Leu
                165                 170                 175

Phe Arg Cys Ile Arg Ser Met Pro Ser His Pro Asp Arg Ala Tyr Asn
            180                 185                 190

Ser Cys Tyr Ser Ala Gly Val Phe His Leu His Gln Gly Asp Ile Leu
        195                 200                 205

Ser Val Ile Ile Pro Arg Ala Arg Ala Lys Leu Asn Leu Ser Pro His
    210                 215                 220

Gly Thr Phe Leu Gly Phe Val Lys Leu
225                 230

<210> SEQ ID NO 3
<211> LENGTH: 1486
<212> TYPE: DNA
<213> ORGANISM: Mus musculus

<400> SEQUENCE: 3
catgccgagt gctttgtgtg tgttacctgc tctaagaagc tggctgggca gcgtttcacc    60
gctgtggagg accagtatta ctgcgtggat tgctacaaga actttgtggc caagaagtgt   120
gctggatgca agaaccccat cactgggttt ggtaaaggct ccagtgtggt ggcctatgaa   180
ggacaatcct ggcacgacta ctgcttccac tgcaaaaaat gctccgtgaa tctgccaac   240 aagcgctttg tatttcataa tgagcaggtg tattgccctg actgtgccaa aaagctgtaa   300
cttgacggct gccctgtcct tcctagataa tggcaccaaa ttctcctgag ctaggggg    360
```

```
aaggagtgtc agagtgtcac tagctcgacc ctggggacaa ggggggactaa tagtaccta      420 gcttgatttc ttcctattct caagttcctt tttatttctc ccttgcgtaa cccgctcttc      480
ccttctgtgc ctttgcctgt attcccaccc tccctgctac ctcttggcca cctcacttct      540
gagaccacag ctgttggcag ggtccctagc tcatgccagc ctcatctcca ggccacatgg      600
ggggctcagt cagagagcca gccctttcgg ttgctctttg gttgagttgg ggggcagttc      660
tgggggctgt gacttgtgct gtcgcactac tgatccaaca gacagagctg caaagcctaa      720
ggcgggaggt gagccggctg cagcggagtg gagggccttc ccagaagcag ggagagcgcc      780
catggcagag cctctgggag cagagtcctg atgtcctgga agcctggaag gatggggcga      840
aatctcggag aaggagagca gtactcaccc agaagcacaa gaagaagcac tcagtcctgc      900
atcttgttcc agttaacatt acctccaagg actctgacgt gacagaggtg atgtggcaac      960
cagtacttag gcgtgggaga ggcctggagg cccagggaga cattgtacga gtctgggaca     1020
ctggaattta tctgctctat agtcaggtcc tgtttcatga tgtgactttc acaatgggtc     1080
aggtggtatc tcgggaagga caagggagaa gagaaactct attccgatgt atcagaagta     1140
tgccttctga tcctgaccgt gcctacaata gctgctacag tgcaggtgtc tttcatttac     1200
atcaagggga tattatcact gtcaaaattc cacgggcaaa cgcaaaactt agcctttctc     1260
cgcatggaac attcctgggg tttgtgaaac tatgattgtt ataaggggg tggggatttc     1320 ccattccaaa aactggctag acaaaggaca aggaacggtc aagaacagct ctccatggct     1380
ttgccttgac tgttgttcct cccttttgcct ttcccgctcc cactatctgg gctttgactc     1440
catggatatt aaaaaagtag aatattttgt gtttatctcc caaaaa                    1486
```

<210> SEQ ID NO 4
<211> LENGTH: 240
<212> TYPE: PRT
<213> ORGANISM: Mus musculus

<400> SEQUENCE: 4

```
Met Pro Ala Ser Ser Pro Gly His Met Gly Gly Ser Val Arg Glu Pro
 1               5                  10                  15

Ala Leu Ser Val Ala Leu Trp Leu Ser Trp Gly Ala Val Leu Gly Ala
            20                  25                  30

Val Thr Cys Ala Val Ala Leu Leu Ile Gln Gln Thr Glu Leu Gln Ser
        35                  40                  45

Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Glu Gln Ser Pro Asp
65                  70                  75                  80

Val Leu Glu Ala Trp Lys Asp Gly Ala Lys Ser Arg Arg Arg Ala
                85                  90                  95

Val Leu Thr Gln Lys His Lys Lys His Ser Val Leu His Leu Val
            100                 105                 110

Pro Val Asn Ile Thr Ser Lys Asp Ser Asp Val Thr Glu Val Met Trp
        115                 120                 125

Gln Pro Val Leu Arg Arg Gly Arg Gly Leu Glu Ala Gln Gly Asp Ile
    130                 135                 140

Val Arg Val Trp Asp Thr Gly Ile Tyr Leu Leu Tyr Ser Gln Val Leu
145                 150                 155                 160

Phe His Asp Val Thr Phe Thr Met Gly Gln Val Val Ser Arg Glu Gly
                165                 170                 175
```

-continued

Gln Gly Arg Arg Glu Thr Leu Phe Arg Cys Ile Arg Ser Met Pro Ser
            180                 185                 190

Asp Pro Asp Arg Ala Tyr Asn Ser Cys Tyr Ser Ala Gly Val Phe His
        195                 200                 205

Leu His Gln Gly Asp Ile Ile Thr Val Lys Ile Pro Arg Ala Asn Ala
    210                 215                 220

Lys Leu Ser Leu Ser Pro His Gly Thr Phe Leu Gly Phe Val Lys Leu
225                 230                 235                 240

<210> SEQ ID NO 5
<211> LENGTH: 181
<212> TYPE: PRT
<213> ORGANISM: Homo sapiens

<400> SEQUENCE: 5

Met Ala Gly Gln Cys Ser Gln Asn Glu Tyr Phe Asp Ser Leu Leu His
1               5                   10                  15

Ala Cys Ile Pro Cys Gln Leu Arg Cys Ser Ser Asn Thr Pro Pro Leu
            20                  25                  30

Thr Cys Gln Arg Tyr Cys Asn Ala Ser Val Thr Asn Ser Val Lys Gly
        35                  40                  45

Thr Asn Ala Ile Leu Trp Thr Cys Leu Gly Leu Ser Leu Ile Ile Ser
    50                  55                  60

Leu Ala Val Phe Val Leu Met Phe Leu Leu Arg Lys Ile Ser Ser Glu
65                  70                  75                  80

Pro Leu Lys Asp Glu Phe Lys Asn Thr Gly Ser Gly Leu Leu Gly Met
                85                  90                  95

Ala Asn Ile Asp Leu Glu Lys Ser Arg Thr Gly Asp Glu Ile Ile Leu
            100                 105                 110

Pro Arg Gly Leu Glu Tyr Thr Val Glu Glu Cys Thr Cys Glu Asp Cys
        115                 120                 125

Ile Lys Ser Lys Pro Lys Val Asp Ser Asp His Cys Phe Pro Leu Pro
    130                 135                 140

Ala Met Glu Glu Gly Ala Thr Ile Leu Val Thr Thr Lys Thr Asn Asp
145                 150                 155                 160

Tyr Cys Lys Ser Leu Pro Ala Ala Leu Ser Ala Thr Glu Ile Glu Lys
                165                 170                 175

Ser Ile Ser Ala Arg
            180

<210> SEQ ID NO 6
<211> LENGTH: 51
<212> TYPE: PRT
<213> ORGANISM: Homo sapiens

<400> SEQUENCE: 6

Met Ala Gly Gln Cys Ser Gln Asn Glu Tyr Phe Asp Ser Leu Leu His
1               5                   10                  15

Ala Cys Ile Pro Cys Gln Leu Arg Cys Ser Ser Asn Thr Pro Pro Leu
            20                  25                  30

Thr Cys Gln Arg Tyr Cys Asn Ala Ser Val Thr Asn Ser Val Lys Gly
        35                  40                  45

Thr Asn Ala
    50

<210> SEQ ID NO 7

-continued

```
<211> LENGTH: 34
<212> TYPE: PRT
<213> ORGANISM: Homo sapiens

<400> SEQUENCE: 7

Cys Ser Gln Asn Glu Tyr Phe Asp Ser Leu Leu His Ala Cys Ile Pro
1               5                   10                  15

Cys Gln Leu Arg Cys Ser Ser Asn Thr Pro Pro Leu Thr Cys Gln Arg
            20                  25                  30

Tyr Cys

<210> SEQ ID NO 8
<211> LENGTH: 21
<212> TYPE: PRT
<213> ORGANISM: Homo sapiens

<400> SEQUENCE: 8

Ile Leu Trp Thr Cys Leu Gly Leu Ser Leu Ile Ile Ser Leu Ala Val
1               5                   10                  15

Phe Val Leu Met Phe
                20

<210> SEQ ID NO 9
<211> LENGTH: 283
<212> TYPE: PRT
<213> ORGANISM: Homo sapiens

<400> SEQUENCE: 9

Met Ala Gly Gln Cys Ser Gln Asn Glu Tyr Phe Asp Ser Leu Leu His
1               5                   10                  15

Ala Cys Ile Pro Cys Gln Leu Arg Cys Ser Ser Asn Thr Pro Pro Leu
            20                  25                  30

Thr Cys Gln Arg Tyr Cys Asn Ala Ser Val Thr Asn Ser Val Lys Gly
        35                  40                  45

Thr Asn Ala Gly Gly Gly Gly Asp Lys Thr His Thr Cys Pro Pro
    50                  55                  60

Cys Pro Ala Pro Glu Leu Gly Gly Pro Ser Val Phe Leu Phe Pro
65                  70                  75                  80

Pro Lys Pro Lys Asp Thr Leu Met Ile Ser Arg Thr Pro Glu Val Thr
                85                  90                  95

Cys Val Val Val Asp Val Ser His Glu Asp Pro Glu Val Lys Phe Asn
            100                 105                 110

Trp Tyr Val Asp Gly Val Glu Val His Asn Ala Lys Thr Lys Pro Arg
        115                 120                 125

Glu Glu Gln Tyr Asn Ser Thr Tyr Arg Val Val Ser Val Leu Thr Val
    130                 135                 140

Leu His Gln Asp Trp Leu Asn Gly Lys Glu Tyr Lys Cys Lys Val Ser
145                 150                 155                 160

Asn Lys Ala Leu Pro Ala Pro Ile Glu Lys Thr Ile Ser Lys Ala Lys
                165                 170                 175

Gly Gln Pro Arg Glu Pro Gln Val Tyr Thr Leu Pro Pro Ser Arg Asp
            180                 185                 190

Glu Leu Thr Lys Asn Gln Val Ser Leu Thr Cys Leu Val Lys Gly Phe
        195                 200                 205

Tyr Pro Ser Asp Ile Ala Val Glu Trp Glu Ser Asn Gly Gln Pro Glu
    210                 215                 220

Asn Asn Tyr Lys Thr Thr Pro Pro Val Leu Asp Ser Asp Gly Ser Phe
```

-continued

```
            225                 230                 235                 240
Phe Leu Tyr Ser Lys Leu Thr Val Asp Lys Ser Arg Trp Gln Gln Gly
                245                 250                 255

Asn Val Phe Ser Cys Ser Val Met His Glu Ala Leu His Asn His Tyr
            260                 265                 270

Thr Gln Lys Ser Leu Ser Leu Ser Pro Gly Lys
        275                 280

<210> SEQ ID NO 10
<211> LENGTH: 281
<212> TYPE: PRT
<213> ORGANISM: Mus musculus

<400> SEQUENCE: 10

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
            20                  25                  30

Gln Pro Tyr Cys Asp Pro Ser Val Thr Ser Ser Val Lys Gly Ser Tyr
        35                  40                  45

Thr Gly Gly Gly Gly Asp Lys Thr His Thr Cys Pro Pro Cys Pro
    50                  55                  60

Ala Pro Glu Leu Leu Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser His Glu Asp Pro Glu Val Lys Phe Asn Trp Tyr
            100                 105                 110

Val Asp Gly Val Glu Val His Asn Ala Lys Thr Lys Pro Arg Glu Glu
        115                 120                 125

Gln Tyr Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Asp Glu Leu
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
                245                 250                 255

Phe Ser Cys Ser Val Met His Glu Ala Leu His Asn His Tyr Thr Gln
            260                 265                 270

Lys Ser Leu Ser Leu Ser Pro Gly Lys
        275                 280

<210> SEQ ID NO 11
<211> LENGTH: 185
<212> TYPE: PRT
<213> ORGANISM: Murine
```

-continued

```
<400> SEQUENCE: 11

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Ala Thr Cys
            20                  25                  30

Gln Pro Tyr Cys Asp Pro Ser Val Thr Ser Ser Val Lys Gly Thr Tyr
            35                  40                  45

Thr Val Leu Trp Ile Phe Leu Gly Leu Thr Leu Val Leu Ser Leu Ala
        50                  55                  60

Leu Phe Thr Ile Ser Phe Leu Leu Arg Lys Met Asn Pro Glu Ala Leu
65                  70                  75                  80

Lys Asp Glu Pro Gln Ser Pro Gly Gln Leu Asp Gly Ser Ala Gln Leu
                85                  90                  95

Asp Lys Ala Asp Thr Glu Leu Thr Arg Ile Arg Ala Gly Asp Asp Arg
            100                 105                 110

Ile Phe Pro Arg Ser Leu Glu Tyr Thr Val Glu Glu Cys Thr Cys Glu
            115                 120                 125

Asp Cys Val Lys Ser Lys Pro Lys Gly Asp Ser Asp His Phe Phe Pro
130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                165                 170                 175

Gly Met Glu Lys Pro Thr His Thr Arg
            180                 185

<210> SEQ ID NO 12
<211> LENGTH: 117
<212> TYPE: PRT
<213> ORGANISM: human-murine Consensus

<400> SEQUENCE: 12

Met Ala Gln Cys Glu Tyr Phe Asp Ser Leu Leu His Ala Cys Pro Cys
1               5                   10                  15

Leu Arg Cys Ser Pro Pro Thr Cys Gln Tyr Cys Ser Val Thr Ser Val
            20                  25                  30

Lys Gly Thr Leu Trp Leu Gly Leu Leu Ser Leu Ala Phe Phe Leu Leu
            35                  40                  45

Arg Lys Glu Leu Lys Asp Glu Gly Ser Leu Ala Leu Arg Gly Asp Ile
        50                  55                  60

Pro Arg Leu Glu Tyr Thr Val Glu Glu Cys Thr Cys Glu Asp Cys Lys
65                  70                  75                  80

Ser Lys Pro Lys Asp Ser Asp His Phe Pro Leu Pro Ala Met Glu Glu
                85                  90                  95

Gly Ala Thr Ile Leu Val Thr Thr Lys Thr Asp Tyr Lys Ser Pro Ala
            100                 105                 110

Leu Ser Glu Lys Arg
        115

<210> SEQ ID NO 13
<211> LENGTH: 81
<212> TYPE: PRT
<213> ORGANISM: Consensus

<400> SEQUENCE: 13

Cys Ser Gln Asn Glu Tyr Phe Asp Ser Leu Leu His Ala Cys Ile Pro
```

```
                1               5                  10                 15
Cys Gln Leu Arg Cys Ser Ser Asn Thr Pro Pro Leu Thr Cys Gln Arg
                20                 25                 30

Tyr Cys Cys Glu Tyr Phe Asp Ser Leu Leu His Ala Cys Pro Cys Leu
                35                 40                 45

Arg Cys Ser Pro Pro Thr Cys Gln Tyr Cys Cys Phe His Ser Glu Tyr
                50                 55                 60

Phe Asp Ser Leu Leu His Ala Cys Pro Pro Ala Thr Cys Gln Pro Tyr
 65                 70                 75                 80

Cys

<210> SEQ ID NO 14
<211> LENGTH: 293
<212> TYPE: PRT
<213> ORGANISM: Homo sapiens

<400> SEQUENCE: 14

Met Ser Gly Leu Gly Arg Ser Arg Arg Gly Arg Ser Arg Val Asp
 1               5                  10                 15

Gln Glu Glu Arg Phe Pro Gln Gly Leu Trp Thr Gly Val Ala Met Arg
                20                 25                 30

Ser Cys Pro Glu Glu Gln Tyr Trp Asp Pro Leu Leu Gly Thr Cys Met
                35                 40                 45

Ser Cys Lys Thr Ile Cys Asn His Gln Ser Gln Arg Thr Cys Ala Ala
                50                 55                 60

Phe Cys Arg Ser Leu Ser Cys Arg Lys Glu Gln Gly Lys Phe Tyr Asp
 65                 70                 75                 80

His Leu Leu Arg Asp Cys Ile Ser Cys Ala Ser Ile Cys Gly Gln His
                85                 90                 95

Pro Lys Gln Cys Ala Tyr Phe Cys Glu Asn Lys Leu Arg Ser Pro Val
               100                105                110

Asn Leu Pro Pro Glu Leu Arg Arg Gln Arg Ser Gly Glu Val Glu Asn
               115                120                125

Asn Ser Asp Asn Ser Gly Arg Tyr Gln Gly Leu Glu His Arg Gly Ser
               130                135                140

Glu Ala Ser Pro Ala Leu Pro Gly Leu Lys Leu Ser Ala Asp Gln Val
145                150                155                160

Ala Leu Val Tyr Ser Thr Leu Gly Leu Cys Leu Cys Ala Val Leu Cys
               165                170                175

Cys Phe Leu Val Ala Val Ala Cys Phe Leu Lys Lys Arg Gly Asp Pro
               180                185                190

Cys Ser Cys Gln Pro Arg Ser Arg Pro Arg Gln Ser Pro Ala Lys Ser
               195                200                205

Ser Gln Asp His Ala Met Glu Ala Gly Ser Pro Val Ser Thr Ser Pro
210                215                220

Glu Pro Val Glu Thr Cys Ser Phe Cys Phe Pro Glu Cys Arg Ala Pro
225                230                235                240

Thr Gln Glu Ser Ala Val Thr Pro Gly Thr Pro Asp Pro Thr Cys Ala
                245                250                255

Gly Arg Trp Gly Cys His Thr Arg Thr Thr Val Leu Gln Pro Cys Pro
               260                265                270

His Ile Pro Asp Ser Gly Leu Gly Ile Val Cys Val Pro Ala Gln Glu
               275                280                285

Gly Gly Pro Gly Ala
```

<210> SEQ ID NO 15
<211> LENGTH: 166
<212> TYPE: PRT
<213> ORGANISM: Homo sapiens

<400> SEQUENCE: 15

```
Met Ser Gly Leu Gly Arg Ser Arg Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
            35                  40                  45

Ser Cys Lys Thr Ile Cys Asn His Gln Ser Gln Arg Thr Cys Ala Ala
        50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr
                165
```

<210> SEQ ID NO 16
<211> LENGTH: 67
<212> TYPE: PRT
<213> ORGANISM: Homo sapiens

<400> SEQUENCE: 16

```
Cys Pro Glu Glu Gln Tyr Trp Asp Pro Leu Leu Gly Thr Cys Met Ser
1               5                   10                  15

Cys Lys Thr Ile Cys Asn His Gln Ser Gln Arg Thr Cys Ala Ala Phe
            20                  25                  30

Cys Cys Arg Lys Glu Gln Gly Lys Phe Tyr Asp His Leu Leu Arg Asp
        35                  40                  45

Cys Ile Ser Cys Ala Ser Ile Cys Gly Gln His Pro Lys Gln Cys Ala
    50                  55                  60

Tyr Phe Cys
65
```

<210> SEQ ID NO 17
<211> LENGTH: 20
<212> TYPE: PRT
<213> ORGANISM: Homo sapiens

<400> SEQUENCE: 17

```
Leu Gly Leu Cys Leu Cys Ala Val Leu Cys Cys Phe Leu Val Ala Val
1               5                   10                  15

Ala Cys Phe Leu
            20
```

<210> SEQ ID NO 18
<211> LENGTH: 397
<212> TYPE: PRT
<213> ORGANISM: Homo sapiens

<400> SEQUENCE: 18

```
Met Ser Gly Leu Gly Arg Ser Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Gly Gly Gly Gly Asp Lys Thr His Thr Cys
                165                 170                 175

Pro Pro Cys Pro Ala Pro Glu Leu Leu Gly Gly Pro Ser Val Phe Leu
            180                 185                 190

Phe Pro Pro Lys Pro Lys Asp Thr Leu Met Ile Ser Arg Thr Pro Glu
        195                 200                 205

Val Thr Cys Val Val Asp Val Ser His Glu Asp Pro Glu Val Lys
    210                 215                 220

Phe Asn Trp Tyr Val Asp Gly Val Glu Val His Asn Ala Lys Thr Lys
225                 230                 235                 240

Pro Arg Glu Glu Gln Tyr Asn Ser Thr Tyr Arg Val Val Ser Val Leu
                245                 250                 255

Thr Val Leu His Gln Asp Trp Leu Asn Gly Lys Glu Tyr Lys Cys Lys
            260                 265                 270

Val Ser Asn Lys Ala Leu Pro Ala Pro Ile Glu Lys Thr Ile Ser Lys
        275                 280                 285

Ala Lys Gly Gln Pro Arg Glu Pro Gln Val Tyr Thr Leu Pro Pro Ser
    290                 295                 300

Arg Asp Glu Leu Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Lys Leu Thr Val Asp Lys Ser Arg Trp Gln
        355                 360                 365

Gln Gly Asn Val Phe Ser Cys Ser Val Met His Glu Ala Leu His Asn
```

```
                370                 375                 380
His Tyr Thr Gln Lys Ser Leu Ser Leu Ser Pro Gly Lys
385                 390                 395

<210> SEQ ID NO 19
<211> LENGTH: 149
<212> TYPE: PRT
<213> ORGANISM: Mus musculus

<400> SEQUENCE: 19

Met Asp Tyr Lys Asp Asp Asp Lys His Lys Lys His Ser
1               5                   10                  15

Val Leu His Leu Val Pro Val Asn Ile Thr Ser Lys Asp Ser Asp Val
            20                  25                  30

Thr Glu Val Met Trp Gln Pro Val Leu Arg Arg Gly Arg Gly Leu Glu
        35                  40                  45

Ala Gln Gly Asp Ile Val Arg Val Trp Asp Thr Gly Ile Tyr Leu Leu
    50                  55                  60

Tyr Ser Gln Val Leu Phe His Asp Val Thr Phe Thr Met Gly Gln Val
65                  70                  75                  80

Val Ser Arg Glu Gly Gln Gly Arg Arg Glu Thr Leu Phe Arg Cys Ile
                85                  90                  95

Arg Ser Met Pro Ser Asp Pro Asp Arg Ala Tyr Asn Ser Cys Tyr Ser
            100                 105                 110

Ala Gly Val Phe His Leu His Gln Gly Asp Ile Ile Thr Val Lys Ile
        115                 120                 125

Pro Arg Ala Asn Ala Lys Leu Ser Leu Ser Pro His Gly Thr Phe Leu
    130                 135                 140

Gly Phe Val Lys Leu
145

<210> SEQ ID NO 20
<211> LENGTH: 59
<212> TYPE: PRT
<213> ORGANISM: Homo sapiens

<400> SEQUENCE: 20

Cys Pro Glu Glu Gln Tyr Trp Asp Pro Leu Leu Gly Thr Cys Met Ser
1               5                   10                  15

Cys Lys Thr Ile Cys Asn His Gln Ser Gln Arg Thr Cys Ala Ala Phe
            20                  25                  30

Cys Arg Ser Leu Ser Cys Arg Lys Glu Gln Gly Lys Phe Tyr Asp His
        35                  40                  45

Leu Leu Arg Asp Cys Ile Ser Cys Ala Ser Ile
    50                  55

<210> SEQ ID NO 21
<211> LENGTH: 58
<212> TYPE: PRT
<213> ORGANISM: Homo sapiens

<400> SEQUENCE: 21

Cys Ser Gln Asn Glu Tyr Phe Asp Ser Leu Leu His Ala Cys Ile Pro
1               5                   10                  15

Cys Gln Leu Arg Cys Ser Ser Asn Thr Pro Pro Leu Thr Cys Gln Arg
            20                  25                  30

Tyr Cys Asn Ala Ser Val Thr Asn Ser Val Lys Gly Thr Asn Ala Ile
        35                  40                  45
```

```
Leu Trp Thr Cys Leu Gly Leu Ser Leu Ile
    50                  55

<210> SEQ ID NO 22
<211> LENGTH: 233
<212> TYPE: PRT
<213> ORGANISM: Homo sapiens
<220> FEATURE:
<221> NAME/KEY: misc_feature
<222> LOCATION: (79)..(79)
<223> OTHER INFORMATION: Xaa is any amino acid

<400> SEQUENCE: 22

Met Gly Gly Pro Val Arg Glu Pro Ala Leu Ser Val Ala Leu Trp Leu
1               5                   10                  15

Ser Trp Gly Ala Ala Leu Gly Ala Val Ala Cys Ala Met Ala Leu Leu
                20                  25                  30

Thr Gln Gln Thr Glu Leu Gln Ser Leu Arg Arg Glu Val Ser Arg Leu
            35                  40                  45

Gln Gly Thr Gly Gly Pro Ser Gln Asn Gly Glu Gly Tyr Pro Trp Gln
    50                  55                  60

Ser Leu Pro Glu Gln Ser Ser Asp Ala Leu Glu Ala Trp Glu Xaa Gly
65                  70                  75                  80

Glu Arg Ser Arg Lys Arg Arg Ala Val Leu Thr Gln Lys Gln Lys Lys
                85                  90                  95

Gln His Ser Val Leu His Leu Val Pro Ile Asn Ala Thr Ser Lys Asp
            100                 105                 110

Asp Ser Asp Val Thr Glu Val Met Trp Gln Pro Ala Leu Arg Arg Gly
        115                 120                 125

Arg Gly Leu Gln Ala Gln Gly Tyr Gly Val Arg Ile Gln Asp Ala Gly
    130                 135                 140

Val Tyr Leu Leu Tyr Ser Gln Val Leu Phe Gln Asp Val Thr Phe Thr
145                 150                 155                 160

Met Gly Gln Val Val Ser Arg Glu Gly Gln Gly Arg Gln Glu Thr Leu
                165                 170                 175

Phe Arg Cys Ile Arg Ser Met Pro Ser His Pro Asp Arg Ala Tyr Asn
            180                 185                 190

Ser Cys Tyr Ser Ala Gly Val Phe His Leu His Gln Gly Asp Ile Leu
        195                 200                 205

Ser Val Ile Ile Pro Arg Ala Arg Ala Lys Leu Asn Leu Ser Pro His
    210                 215                 220

Gly Thr Phe Leu Gly Phe Val Lys Leu
225                 230

<210> SEQ ID NO 23
<211> LENGTH: 232
<212> TYPE: PRT
<213> ORGANISM: Mus musculus

<400> SEQUENCE: 23

Met Gly Gly Ser Val Arg Glu Pro Ala Leu Ser Val Ala Leu Trp Leu
1               5                   10                  15

Ser Trp Gly Ala Val Leu Gly Ala Val Thr Cys Ala Val Ala Leu Leu
                20                  25                  30

Ile Gln Gln Thr Glu Leu Gln Ser Leu Arg Arg Glu Val Ser Arg Leu
            35                  40                  45

Gln Arg Ser Gly Gly Pro Ser Gln Lys Gln Gly Glu Arg Pro Trp Gln
```

```
                   50                  55                  60
Ser Leu Trp Glu Gln Ser Pro Asp Val Leu Glu Ala Trp Lys Asp Gly
 65                  70                  75                  80

Ala Lys Ser Arg Arg Arg Ala Val Leu Thr Gln Lys His Lys Lys
                 85                  90                  95

Lys His Ser Val Leu His Leu Val Pro Val Asn Ile Thr Ser Lys Asp
                100                 105                 110

Ser Asp Val Thr Glu Val Met Trp Gln Pro Val Leu Arg Arg Gly Arg
                115                 120                 125

Gly Pro Gly Gly Gln Gly Asp Ile Val Arg Val Trp Asp Thr Gly Ile
130                 135                 140

Tyr Leu Leu Tyr Ser Gln Val Leu Phe His Asp Val Thr Phe Thr Met
145                 150                 155                 160

Gly Gln Val Val Ser Arg Glu Gly Gln Gly Arg Arg Glu Thr Leu Phe
                165                 170                 175

Arg Cys Ile Arg Ser Met Pro Ser Asp Pro Asp Arg Ala Tyr Asn Ser
                180                 185                 190

Cys Tyr Ser Ala Gly Val Phe His Leu His Gln Gly Asp Ile Ile Thr
                195                 200                 205

Val Lys Ile Pro Arg Ala Asn Ala Lys Leu Ser Leu Ser Pro His Gly
                210                 215                 220

Thr Phe Leu Gly Phe Val Lys Leu
225                 230

<210> SEQ ID NO 24
<211> LENGTH: 190
<212> TYPE: PRT
<213> ORGANISM: Consensus

<400> SEQUENCE: 24

Met Gly Gly Val Arg Glu Pro Ala Leu Ser Val Ala Leu Trp Leu Ser
 1               5                  10                  15

Trp Gly Ala Leu Gly Ala Val Cys Ala Ala Leu Leu Gln Gln Thr Glu
                20                  25                  30

Leu Gln Ser Leu Arg Arg Glu Val Ser Arg Leu Gln Gly Gly Pro Ser
                35                  40                  45

Gln Pro Trp Gln Ser Leu Glu Gln Ser Asp Leu Glu Ala Trp Gly Ser
                50                  55                  60

Arg Arg Arg Ala Val Leu Thr Gln Lys Lys His Ser Val Leu His
 65                  70                  75                  80

Leu Val Pro Asn Thr Ser Lys Asp Ser Asp Val Thr Glu Val Met Trp
                 85                  90                  95

Gln Pro Leu Arg Arg Gly Arg Gly Gln Gly Val Arg Asp Gly Tyr Leu
                100                 105                 110

Leu Tyr Ser Gln Val Leu Phe Asp Val Thr Phe Thr Met Gly Gln Val
                115                 120                 125

Val Ser Arg Glu Gly Gln Gly Arg Glu Thr Leu Phe Arg Cys Ile Arg
                130                 135                 140

Ser Met Pro Ser Pro Asp Arg Ala Tyr Asn Ser Cys Tyr Ser Ala Gly
145                 150                 155                 160

Val Phe His Leu His Gln Gly Asp Ile Val Ile Pro Arg Ala Ala Lys
                165                 170                 175

Leu Leu Ser Pro His Gly Thr Phe Leu Gly Phe Val Lys Leu
                180                 185                 190
```

-continued

```
<210> SEQ ID NO 25
<211> LENGTH: 26
<212> TYPE: DNA
<213> ORGANISM: Mus musculus

<400> SEQUENCE: 25
cacaatacct gtggccctct taagag                                          26

<210> SEQ ID NO 26
<211> LENGTH: 26
<212> TYPE: DNA
<213> ORGANISM: Antisense

<400> SEQUENCE: 26
tggtaaacgg tcatcctaac gacatc                                          26

<210> SEQ ID NO 27
<211> LENGTH: 24
<212> TYPE: DNA
<213> ORGANISM: Homo sapiens

<400> SEQUENCE: 27
ttacttgtcc ttccaggctg ttct                                            24

<210> SEQ ID NO 28
<211> LENGTH: 25
<212> TYPE: DNA
<213> ORGANISM: Antisense

<400> SEQUENCE: 28
catagaaacc aaggaagttt ctacc                                           25

<210> SEQ ID NO 29
<211> LENGTH: 26
<212> TYPE: DNA
<213> ORGANISM: Homo sapiens

<400> SEQUENCE: 29
agcatcctga gtaatgagtg gcctgg                                          26

<210> SEQ ID NO 30
<211> LENGTH: 27
<212> TYPE: DNA
<213> ORGANISM: Antisense

<400> SEQUENCE: 30
gtgatgacga cctacagctg cactggg                                         27

<210> SEQ ID NO 31
<211> LENGTH: 394
<212> TYPE: PRT
<213> ORGANISM: Homo sapiens

<400> SEQUENCE: 31

Met Glu Trp Ser Trp Val Phe Leu Phe Phe Leu Ser Val Thr Thr Gly
1               5                   10                  15

Val His Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60
```

-continued

```
Val Ser His Glu Asp Pro Glu Val Lys Phe Asn Trp Tyr Val Asp Gly
 65              70                  75                  80

Val Glu Val His Asn Ala Lys Thr Lys Pro Arg Glu Glu Gln Tyr Asn
                 85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
            195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys Ser Arg Ala Val Leu Thr Gln Lys Gln Lys
                245                 250                 255

Lys Gln His Ser Val Leu His Leu Val Pro Ile Asn Ala Thr Ser Lys
            260                 265                 270

Asp Asp Ser Asp Val Thr Glu Val Met Trp Gln Pro Ala Leu Arg Arg
            275                 280                 285

Gly Arg Gly Leu Gln Ala Gln Gly Tyr Gly Val Arg Ile Gln Asp Ala
    290                 295                 300

Gly Val Tyr Leu Leu Tyr Ser Gln Val Leu Phe Gln Asp Val Thr Phe
305                 310                 315                 320

Thr Met Gly Gln Val Val Ser Arg Glu Gly Gln Gly Arg Gln Glu Thr
                325                 330                 335

Leu Phe Arg Cys Ile Arg Ser Met Pro Ser His Pro Asp Arg Ala Tyr
            340                 345                 350

Asn Ser Cys Tyr Ser Ala Gly Val Phe His Leu His Gln Gly Asp Ile
            355                 360                 365

Leu Ser Val Ile Ile Pro Arg Ala Arg Ala Lys Leu Asn Leu Ser Pro
    370                 375                 380

His Gly Thr Phe Leu Gly Phe Val Lys Leu
385                 390
```

METHODS AND COMPOSITIONS OF MATTER CONCERNING APRIL/G70, BCMA, BLYS/AGP-3 AND TACI

This application claims the benefit of U.S. Provisional Application Ser. No. 60/204,039, filed May 12, 2000 and U.S. Provisional Application Ser. No. 60/214,591, filed Jun. 27, 2000, which are incorporated herein by reference.

FIELD OF THE INVENTION

The present invention relates to proteins that are involved in inflammation and immunomodulation, survival, or activation or in lymphoproliferative disorders or other cancers. The invention further relates to proteins related to the tumor necrosis factor (TNF)/nerve growth factor (NGF) superfamily and related nucleic acids, expression vectors, host cells, and binding assays. The specification also describes compositions and methods for the treatment of immune-related and inflammatory, autoimmune and other immune-related diseases or disorders, such as rheumatoid arthritis (RA), Crohn's disease (CD), lupus, and graft versus host disease (GvHD) as well as for treatment of lymphoproliferative diseases and other cancers.

BACKGROUND OF THE INVENTION

After years of study in necrosis of tumors, tumor necrosis factors (TNFs) α and β were finally cloned in 1984. The ensuing years witnessed the emergence of a superfamily of TNF cytokines, including fas ligand (FasL), CD27 ligand (CD27L), CD30 ligand (CD30L), CD40 ligand (CD40L), TNF-related apoptosis-inducing ligand (TRAIL, also designated AGP-1), osteoprotegerin binding protein (OPG-BP or OPG ligand), 4-1BB ligand, LIGHT, APRIL, and TALL-1. Smith et al. (1994), *Cell,* 76: 959–962; Lacey et al. (1998), *Cell,* 93: 165–176; Chichepotiche et al. (1997), *J. Biol. Chem.,* 272: 32401–32410; Mauri et al. (1998), *Immunity,* 8: 21–30; Hahne et al. (1998), *J. Exp. Med.,* 188: 1185–90; Shu et al. (1999), *J. Leukocyte Biology,* 65: 680–3. This family is unified by its structure, particularly at the C-terminus. In addition, most members known to date are expressed in immune compartments, although some members are also expressed in other tissues or organs, as well. Smith et al. (1994), *Cell* 76: 959–62. All ligand members, with the exception of LT-α, are type II transmembrane proteins, characterized by a conserved 150 amino acid region within C-terminal extracellular domain. Though restricted to only 20–25% identity, the conserved 150 amino acid domain folds into a characteristic β-pleated sheet sandwich and trimerizes. This conserved region can be proteolyticaly released, thus generating a soluble functional form. Banner et al. (1993), *Cell,* 73: 431–445.

Many members within this ligand family are expressed in lymphoid enriched tissues and play important roles in the immune system development and modulation. Smith et al. (1994). For example, TNFα is mainly synthesized by macrophages and is an important mediator for inflammatory responses and immune defenses. Tracey & Cerami (1994), *Annu. Rev. Med.,* 45: 491–503. Fas-L, predominantly expressed in activated T cell, modulates TCR-mediated apoptosis of thymocyts. Nagata, S. & Suda, T. (1995) *Immunology Today,* 16:39–43; Castrim et al. (1996), *Immunity,* 5:617–27. CD40L, also expressed by activated T cells, provides an essential signal for B cell survival, proliferation and immunoglobulin isotype switching. Noelle (1996), *Immunity,* 4:415–9.

The cognate receptors for most of the TNF ligand family members have been identified. These receptors share characteristic multiple cysteine-rich repeats within their extracellular domains, and do not possess catalytic motifs within cytoplasmic regions. Smith et al. (1994). The receptors signal through direct interactions with death domain proteins (e.g. TRADD, FADD, and RIP) or with the TRAF proteins (e.g. TRAF2, TRAF3, TRAF5, and TRAF6), triggering divergent and overlapping signaling pathways, e.g. apoptosis, NF-κB activation, or JNK activation. Wallach et al. (1999), *Annual Review of Immunology* 17: 331–67. These signaling events lead to cell death, proliferation, activation or differentiation. The expression profile of each receptor member varies. For example, TNFR1 is expressed on a broad spectrum of tissues and cells, whereas the cell surface receptor of OPGL is mainly restricted to the osteoclasts. Hsu et al. (1999) *Proc. Natl. Acad. Sci. USA,* 96:3540–5. Such proteins are believed to play a role in inflammatory and immune processes, suggesting their usefulness in treating autoimmune and inflammatory disorders.

A number of research groups have recently identified TNF family ligands with the same or substantially similar sequence, but they have not identified the associated receptor. The ligand has been variously named neutrokine-α (WO 98/18921, published May 7, 1998), 63954 (WO 98/27114, published Jun. 25, 1998), TL5 (EP 869 180, published Oct. 7, 1998), NTN-2 (WO 98/55620 and WO 98/55621, published Dec. 10, 1998), TNRL1-alpha (WO 9911791, published Mar. 11, 1999), kay ligand (WO99/12964, published Mar. 18, 1999), and AGP-3 (U.S. Prov. App. No. 60/119, 906, filed Feb. 12, 1999 and No. 60/166,271, filed Nov. 18, 1999, respectively). Each of these references is hereby incorporated by reference. Hereinafter, this protein sequence is referred to as "AGP-3."

A recent paper has identified two previously known proteins as receptors for AGP-3. Gross et al. (2000), *Nature* 404: 995–9. The first receptor was previously identified as a lymphocyte surface receptor named Transmembrane Activator and CAML Interactor (TACI). See WO 98/39361, published Sep. 11, 1998, and von Bulow & Bram (1997), *Science,* 278:138–140, each of which is hereby incorporated by reference in its entirety. According to these references, TACI binds an intracellular cyclophilin ligand designated CAML, which modulates the calcium signaling pathway in lymphocytes.

The second receptor identified for AGP-3 is the so-called B cell maturation protein (BCMA). The human BCMA gene was discovered by molecular analysis of a t(4;16) translocation, which characteristic of a human T cell lymphoma. Laabi et al. (1993), *EMBO J.* 11: 3897–3904. BCMA mRNA was reported to be found mainly in lymphoid tissues. Human BCMA cDNA encodes a 184 amino acids protein (185 residues for the mouse), and the literature reports no obvious similarity with any known protein or motif, and its function remained unknown. The protein was reported to reside in the Golgi apparatus (Gras et al. (1995), *Intl. Immunol.* 7: 1093–1106). Recent speculation suggested that BCMA may be a distant member of the TNFR super family. Madry et al. (1998), *Intl. Immunol.* 10: 1693–1702.

A ligand called APRIL or G70 is a TNF family ligand that remains without a receptor reported in the literature. According to the literature, APRIL is associated with prostate cancer, breast cancer, Alzheimer's disease, immune disorders, inflammatory disorders, and gestational abnormalities. See WO 99/00518 (Jun. 26, 1997); WO 99/11791 (Sep. 5, 1997); WO 99/12965 (Sep. 12, 1997); EP 911 633 (Oct. 8, 1997); EP 919 620 (Nov. 26, 1997); WO 99/28462 (Dec. 3, 1997); WO 99/33980 (Dec. 30, 1997); WO 99/35170 (Jan. 5, 1998); and Hahne et al. (1998), *J. Exp.*

Med. 188: 1185–90. (Each of the foregoing references is hereby incorporated by reference in its entirety.) A recent paper described APRIL isoforms and suggested that APRIL causes cell death. Kelly et al. (2000), *Cancer Res.* 60: 1021–7. The art would benefit from identification of a receptor for APRIL and a clarification of its activity.

SUMMARY OF THE INVENTION

It has now been found that sG70 (APRIL) binds to cell-surface receptors on T and B lymphoma cells resulting in stimulation of proliferation of primary human and mouse B and T cells both in vitro and in vivo. It has now been found that BCMA and TACI are cell-surface receptors for APRIL. It has also been found that APRIL competes with AGP3's binding to TACI and BCMA. Furthermore it is shown here that sBCMA inhibits APRIL and AGP3 binding to its receptors. sBCMA ameliorates T cell dependent and T cell independent humoral immune responses in vivo. In addition it has now been found that sTACI inhibits APRIL and AGP3 binding to its receptors and ameliorates T cell dependent and T cell independent humoral immune responses in vivo. In addition it has now been found that sBCMA reduces lymphoma and colon carcinoma cell tumor growth in vivo. It has also now been found that sBCMA increases survival and reduces incidence of proteinurea, and development of anti-dsDNA antibodies in an animal model of lupus. It has also been found that BCMA exhibits similarity with TACI within a single cysteine rich domain located N-terminal to a potential transmembrane domain. It has also been found that APRIL stimulates B cell growth and immunoglobulin production in vitro and in vivo. Furthermore, treatment with a blocking anti-APRIL antibody ameliorates generation of antigen specific immunoglobulin, suggesting that endogenous APRIL is required for humoral immunity in vivo. This invention concerns novel methods of use and compositions of matter that exploit these discoveries. The discoveries provides a strategy for development of therapeutics for treatment of autoimmune diseases, and cancer, for prevention of transplant rejection.

These discoveries show that activity, disease states, and disease parameters associated with APRIL and AGP-3 may be affected by modulation of BCMA. Likewise, disease states and disease parameters associated with TACI can be affected by modulation of APRIL. Further, such disease states and disease parameters can be affected by modulation of any of TACI, BCMA, APRIL and AGP-3 together. This discovery further suggests molecules and methods of treatment by which more than one of TACI, BCMA, APRIL, and AGP-3 may be modulated by a single molecule.

DESCRIPTION OF THE FIGURES

FIG. 1 shows the sequence of human APRIL (SEQ ID NOS: 1 and 2)
Start and stop codons are underlined.

FIGS. 2A and 2B show the DNA and amino acid sequences of mouse APRIL/G70 (SEQ ID NOS: 3 and 4, respectively). Start and stop codons are underlined. The amino acid sequence of FLAG-tagged soluble mouse APRIL (SEQ ID NO: 19) is also provided.

FIG. 3 shows an alignment of human (SEQ ID NO: 22) and mouse (SEQ ID NO: 23) APRIL. The middle line of each row shows the consensus sequence (SEQ ID NO: 24).

FIG. 4 shows that G70/APRIL is a potent stimulator for B and T cell lymphoma.

FIG. 4A shows dose-dependent stimulation of proliferation of Jurkat cells (human leukemic T cells), Raji (human Burkitt lymphoma) and K562 cells (human chronic myelogenous leukemia cells). The proliferation of cells was determined by incubating $3 \times 10^4$ cells/well in 100 $\mu$l medium with indicated concentration of recombinant sG70/APRIL and phosphate-buffered saline (PBS, no ligand) as a control. After 48 hours, the number of viable cells were measured by Celltiter 96 AQ proliferation assay (Promega, Madison, Wis.).

FIGS. 5A and 5B show FACS analysis of G70/APRIL receptor binding. G70/APRIL receptor expression was assessed on indicated cell line using anti-Flag monoclonal antibody followed by FITC-conjugated goat antibody to mouse IgG. A anti-mouse CD16/CD32 monoclonal antibody (Fc Block) was used to block non-specific binding to cells.

FIG. 6 shows the effect of sG70/APRIL on human peripheral blood B cell, T cell and granulocyte proliferation. Human peripheral T cell (CD4+ and CD8+), B cells and granulocyte were purified from three different donors by using RosetteSep cocktail antibodies (Stem cell Tech. Vancouver). Purified cells were cultured in tissue culture-treated plastic wells(Becton-Dickinson, Lincoln park, N.J.) for 6 Days in RPMI-1640 medium supplemented with 10% fetal calf serum, 2 mM L-glutamine and 2-ME (50 uM) in the present different concentration of sG70/APRIL. For the B cell proliferation assay, plastic wells were coated with purified mouse anti-human Ig M monoclonal antibody (3 $\mu$g/ml, Pharmingen, San Diego, Calif.). The positive control for T cell stimulation is IL-2.

FIG. 7 shows the effect of G70/APRIL on murine T-and B-cell proliferation in vitro. T-and B-cells from the spleens of C57B1 mice were purified by selection through a murine T-cell and B-cell enrichment columns. $1 \times 10^5$ cells per well were cultured in the absence or presence of various G70/APRIL for 48 hours, pulsed during the last 18 hours with 0.5 $\mu$Ci $^3$H thymidine and harvested to count the incorporated radioactivity.

FIGS. 10A and 10B show the sequence of human BCMA (SEQ ID NO: 5). BCMA's extracellular domain (SEQ ID NO: 6) extends from aa 1 to aa 51 and is identified by arrows. The cysteine-rich consensus region (SEQ ID NO: 7, described further hereinafter) is shown in boldface. The transmembrane region (SEQ ID NO: 8) is underlined. huBCMA-Fc (SEQ ID NO: 9). mBCMA-Fc (SEQ ID NO: 10).

FIG. 11 shows an alignment of human BCMA amino acid sequence and murine BCMA amino acid sequence (SEQ ID NO: 11). The human sequence is shown on the top line, the murine on the bottom line in each row. The human-murine consensus sequence (SEQ ID NO: 12) appears as the middle line of each row. A "+" in the consensus sequence indicates a conservative substitution. The cysteine-rich portion of the consensus sequence (SEQ ID NO: 13) appears in boldface.

FIGS. 12A and 12B show the sequence of hTACI (SEQ ID NO: 14).

TACI's extracellular domain (SEQ ID NO: 15) extends from aa 1 to aa 166. The cysteine-rich consensus region (SEQ ID NO: 16) is shown in boldface, and the transmembrane region (SEQ ID NO: 17) is underlined. hTACI-Fc (SEQ ID NO: 18).

FIG. 13 shows an alignment of cysteine rich extracellular regions of human TACI and human BCMA. The BCMA cysteine rich consensus region (SEQ ID NO: 20) appears as the top line, the TACI cysteine rich consensus region (SEQ ID NO: 21) appears as the bottom line of each row. Conserved amino acid residues are indicated by a vertical bar (I). Related amino acid residues are indicated with a colon (:).

Figure 14A:
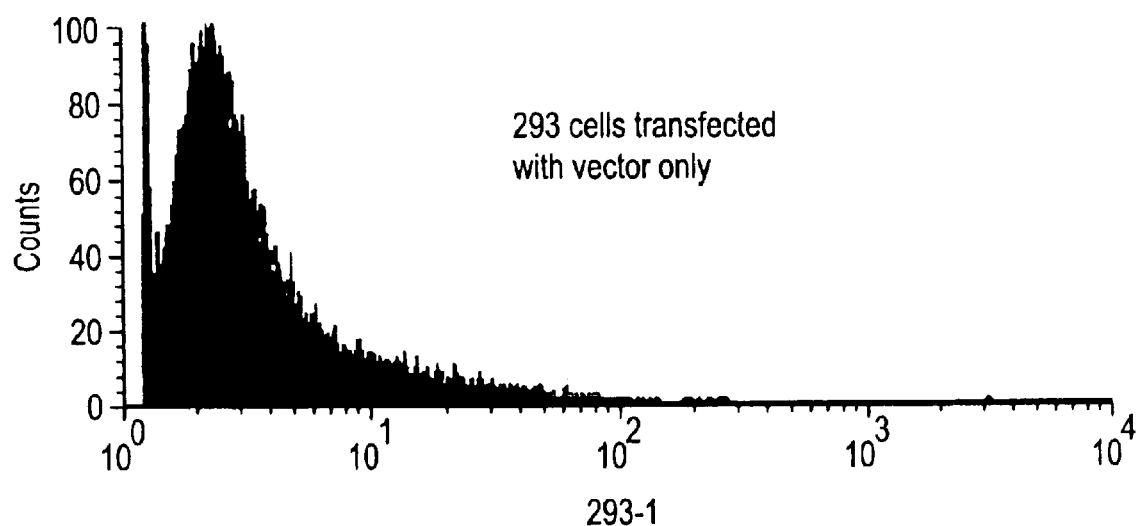
Figure 14B:
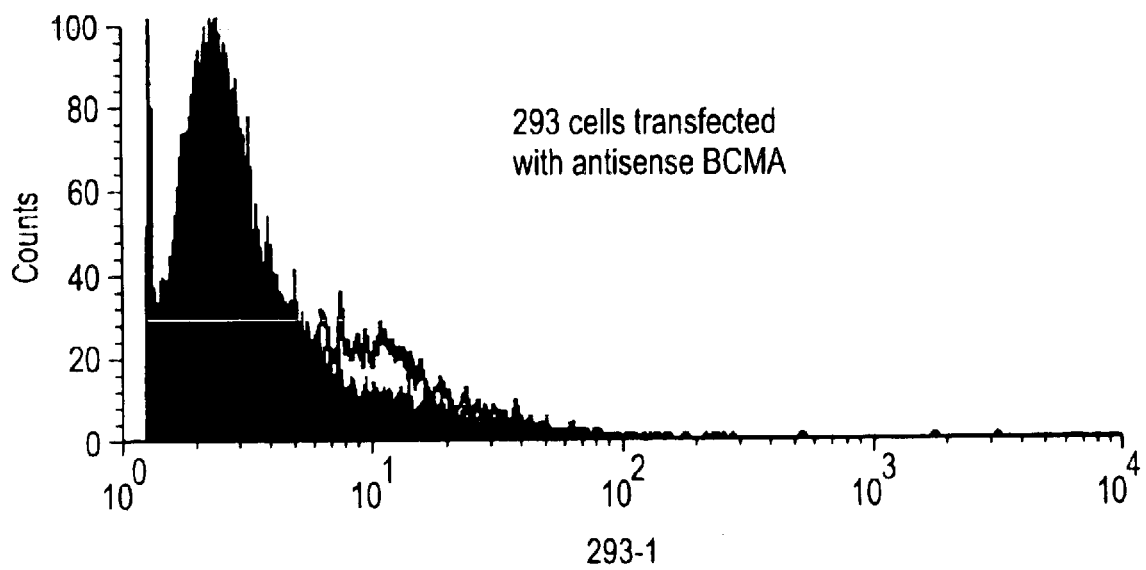
Figure 14C:
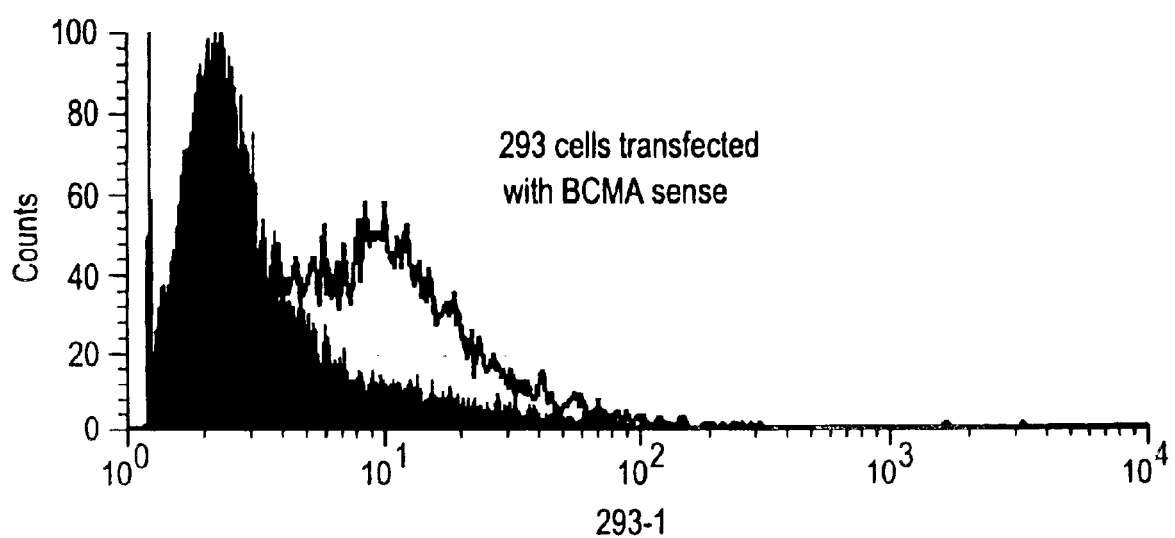

FIGS. 14A, 14B and 14C show soluble mouse G70/APRIL binding to 293 cells expressing the BCMA gene. Human 293 cells transfected with the pmBCMA and pcDNA3 vectors were incubated with G70/APRIL-Flag, followed by FITC-conjugated anti-Flag antibody staining for FACS analysis. A. 293 cells transfected with pcDNA3 vector only. B. 293 cells transfected with antisense pmBCMA vector. C. 293 cells transfected with sense pmBCMA vector.

Table 2 shows BIACore analysis of the stoichiometric binding kinetics of APRIL and AGP-3 to BCMA and TACI. Flag-APRIL specifically binds to murine and human BCMA with affinities of 0.25 nM and 0.29 nM, respectively, and to human TACI with an affinity of 1.48 nM. Also a longer version of Flag-tagged APRIL (aa 50–240) binds to BCMA and TACI with high affinity similar to that of Fc-AGP-3 (Table 2). In separate experiments, we determined that neither APRIL nor AGP-3 bind to OPG and also that TNFα, OPGL, LIGHT, TWEAK, and TRAIL do not bind to BCMA or TACI. Hence, APRIL and AGP-3 specifically bind to both BCMA and TACI with high affinity.

FIG. 15 shows G70/APRIL binding to 293 cells expressing the hTACI gene. Human 293 cells transfected with the phTACI and pcDNA3 vectors were incubated with G70/APRIL-Flag, followed by FITC-conjugated anti-Flag antibody staining for FACS analysis.

Figure 15A:
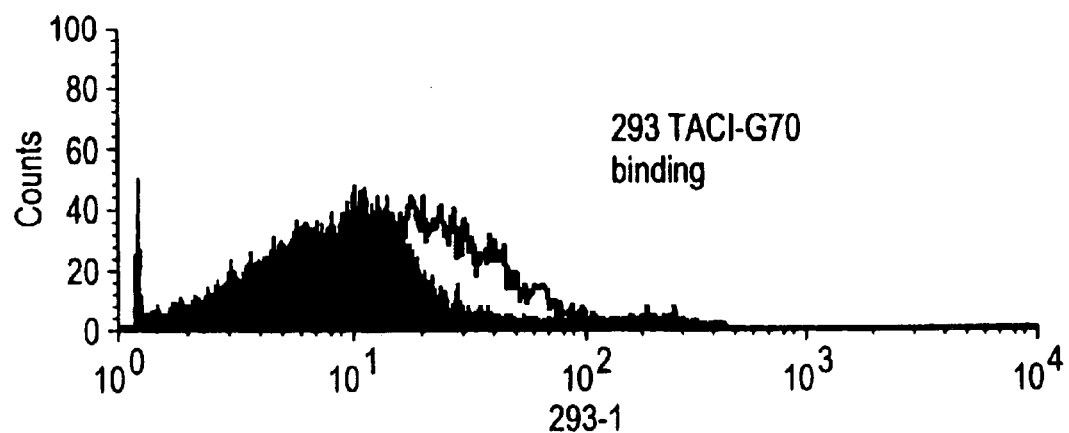

In FIG. 15A, 293 cells were transfected with phTACI vector.

Figure 15B:
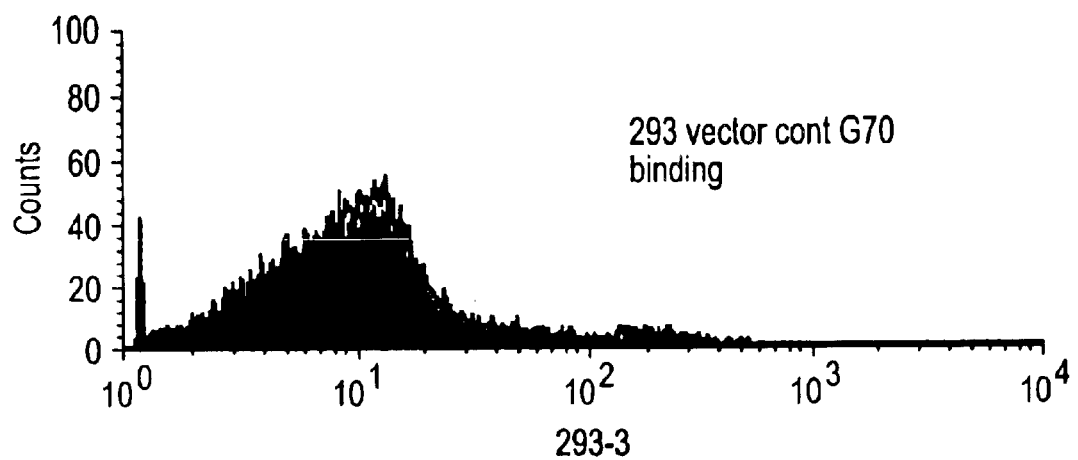

In FIG. 15B, 293 cells were transfected with pcDNA3 vector only.

Figures 16C, 16D:
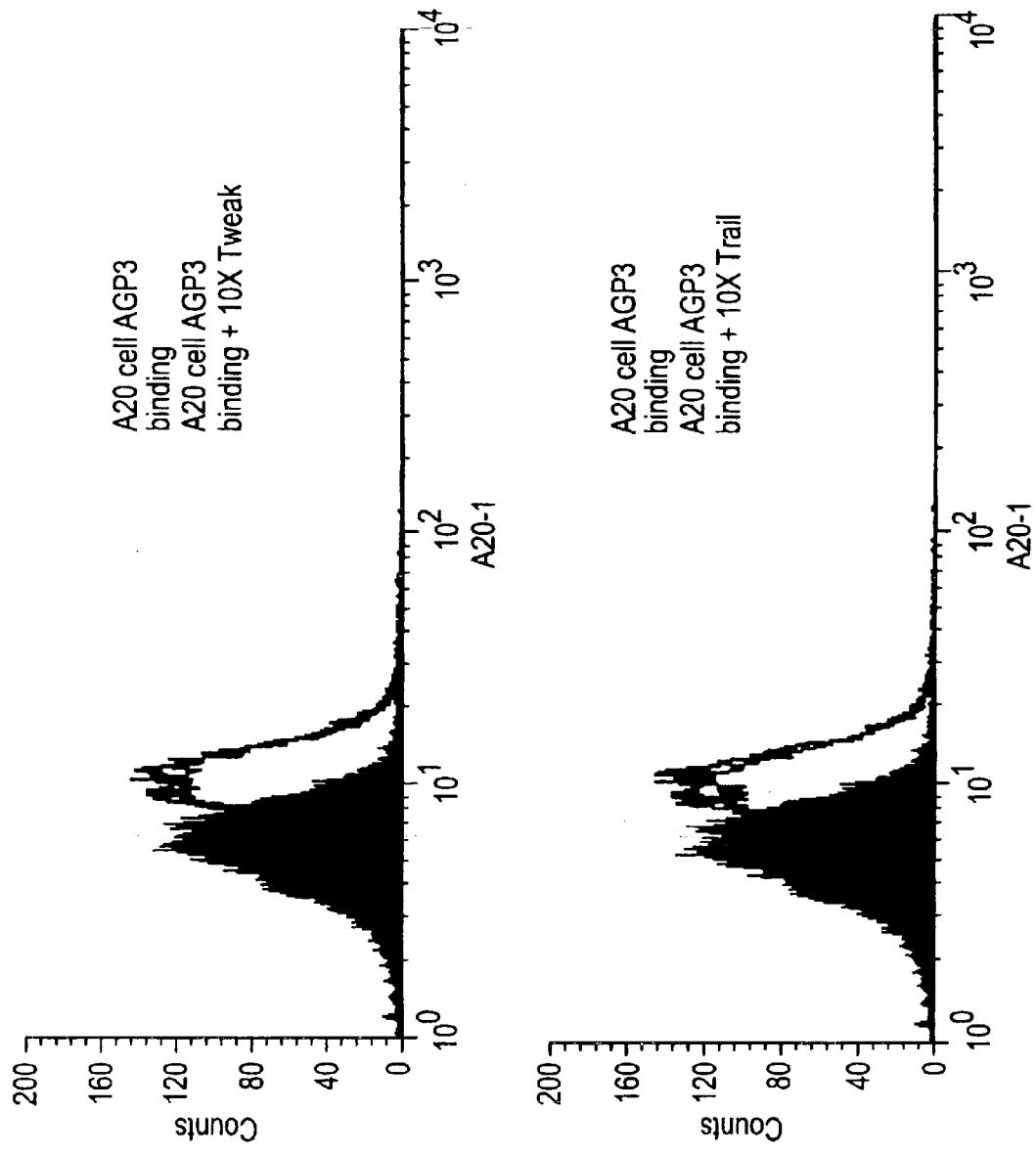

FIG. 16 shows G70/APRIL completely blocks AGP3 binding to its receptor. Mouse B lymphoma cells A20 were stained with AGP3-Fc or plus 10 fold excess G70/APRIL, CD40 ligand, TRAIL ligand and Tweak. After washing 3 times, cells were incubated with FITC-conjugated goat anti-human IgG-Fc secondary antibody. In FIG. 16A, 10 fold G70/APRIL completely blocked AGP3 binding to A20 cells. In FIGS. 16B,C and D, 10 fold CD40 ligand, Tweak and TRAIL do not have that effect on AGP3 binding.

Figure 17A:
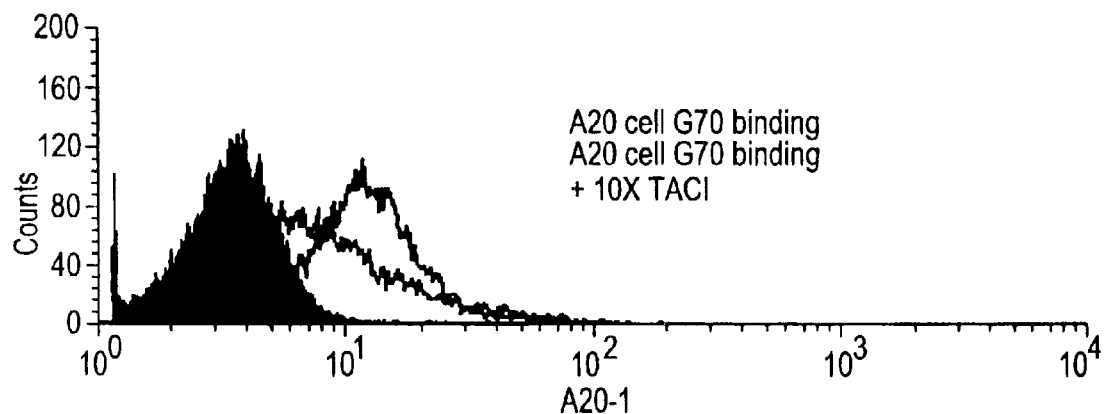
Figure 17B:
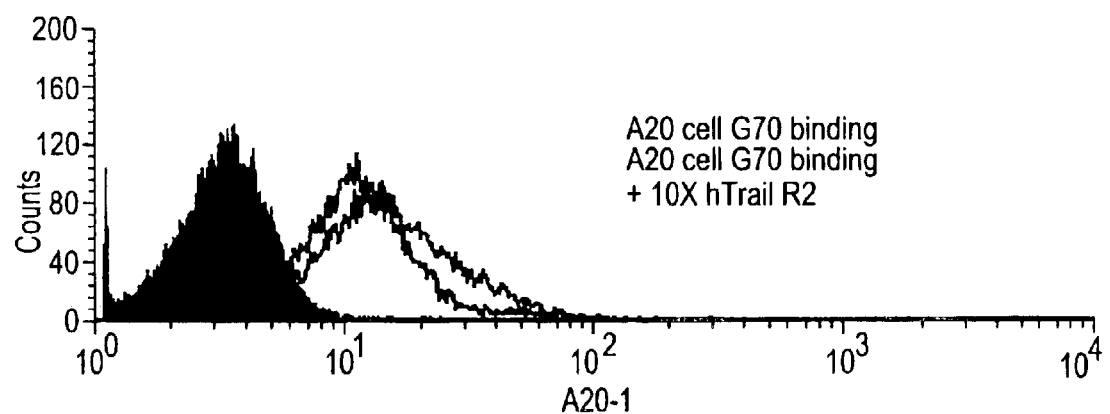
Figure 17C:
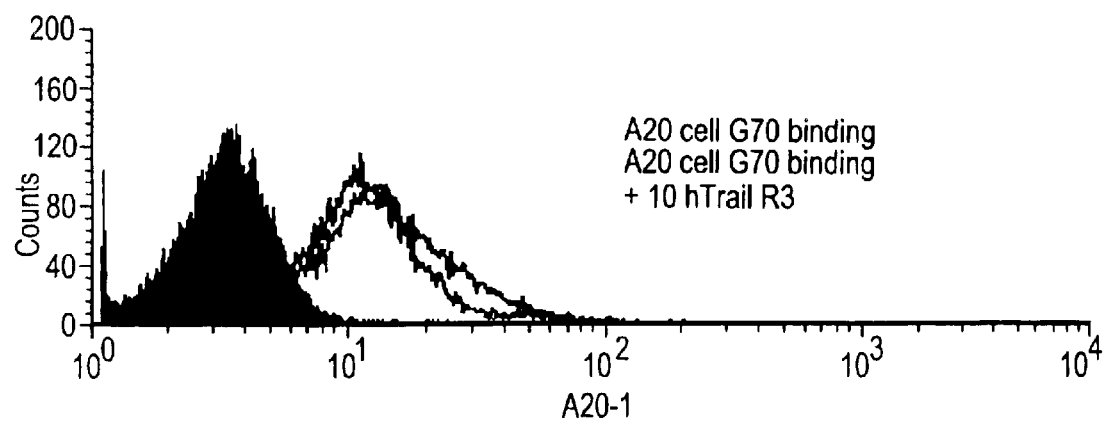

FIG. 17 shows that soluble TACI receptor (sTACI) binding competes with G70/APRIL binding to A20 cells. A20 cells were incubated with G70/APRIL or at same time plus 10 fold soluble TACI, TRAIL R2 and TRAIL R3 receptor, followed by FITC-conjugated anti-Flag antibody staining for FACS analysis. In FIG. 17A, soluble TACI receptor partially competed in binding G70/APRIL binding to A20 cells. In FIGS. 17B and C, soluble TRAIL R2 and TRAIL R3 receptors did not interfere with G70/APRIL binding.

Figure 18:
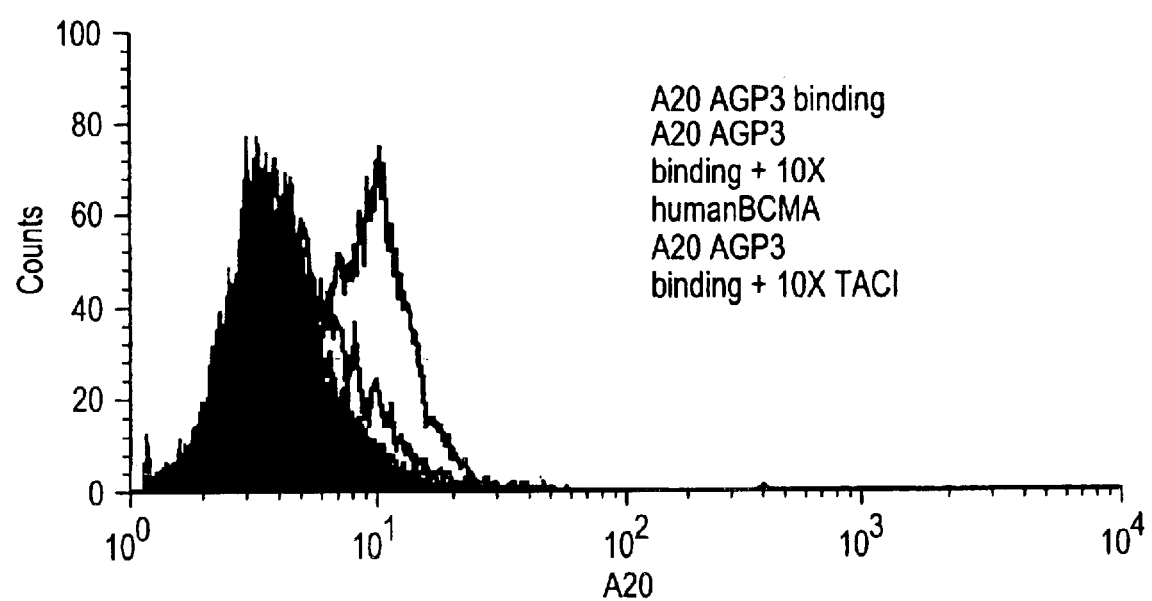

FIG. 18 shows that soluble human BCMA-Fc receptor fusion protein (shBCMA-Fc) and soluble human TACI-Fc receptor fusion protein (shTACI-Fc) completely blocks soluble human AGP-3-Fc receptor fusion protein (shAGP3-Fc) binding to A20 cells. A20 cells were incubated shAGP3-Fc or at same time plus 10 fold shBCMA-Fc or shTACI-Fc followed by FITC-conjugated anti-Flag antibody staining for FACS analysis.

Figure 19A:
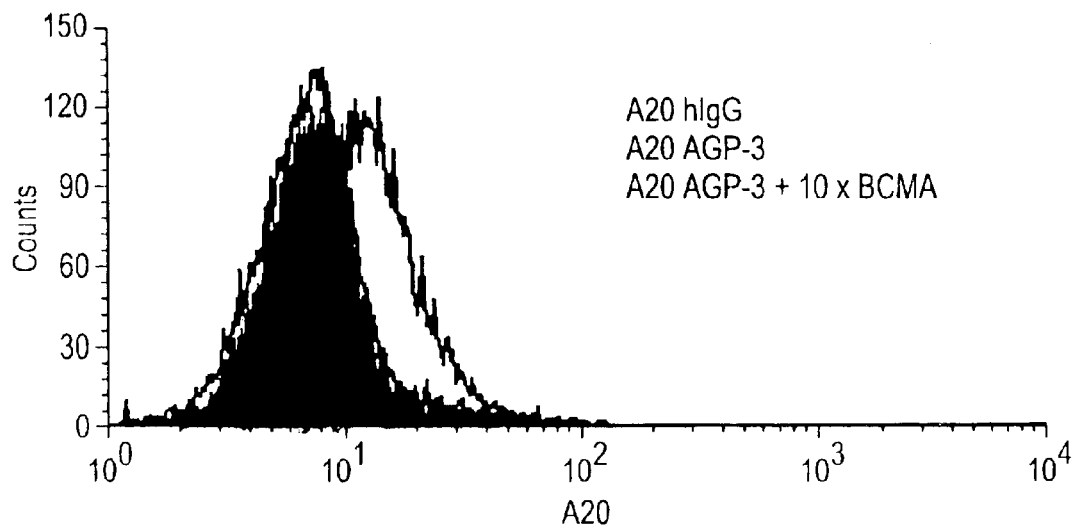
Figure 19B:
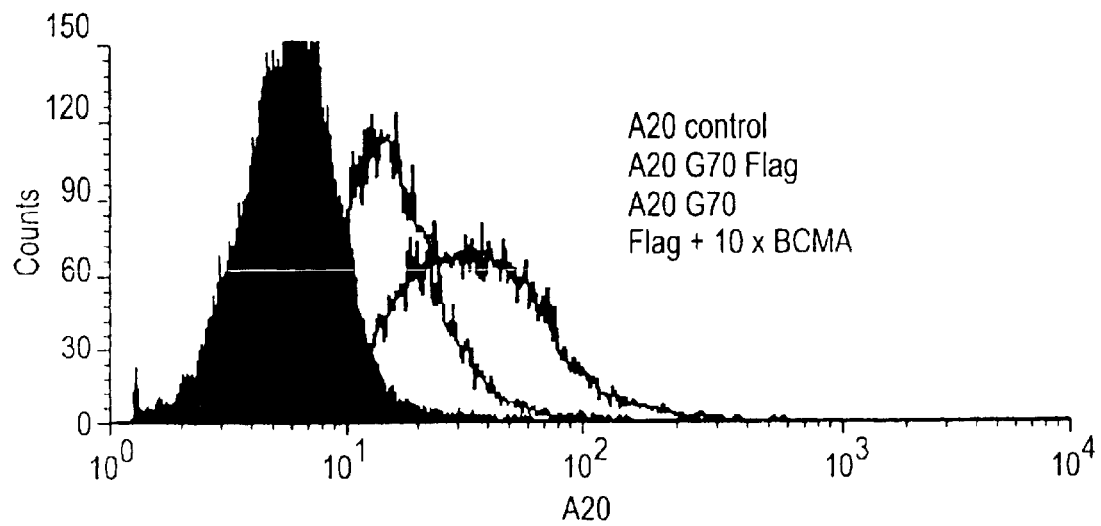

FIG. 19A shows shBCMA-Fc completely blocks shAGP3-Fc binding to A20 cells. A20 cells were incubated with shAGP3-Fc with or without 10 fold soluble hBCMA-Fc followed by FITC-conjugated anti-Flag antibody staining for FACS analysis. FIG. 19B shows that shBCMA-Fc blocks soluble murine APRIL (smAPRIL) binding to A20 cells. A20 cells were incubated with smAPRIL with or without 10 fold shBCMA-Fc followed by FITC-conjugated anti-Flag antibody staining for FACS analysis.

Figure 20A:
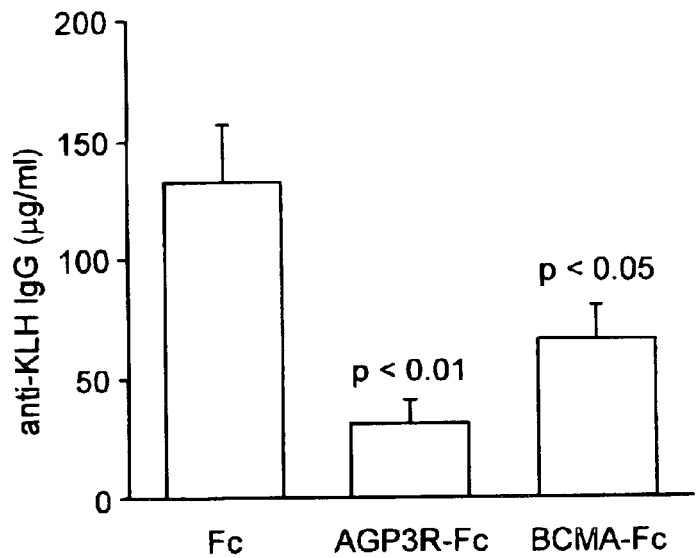
Figure 20B:
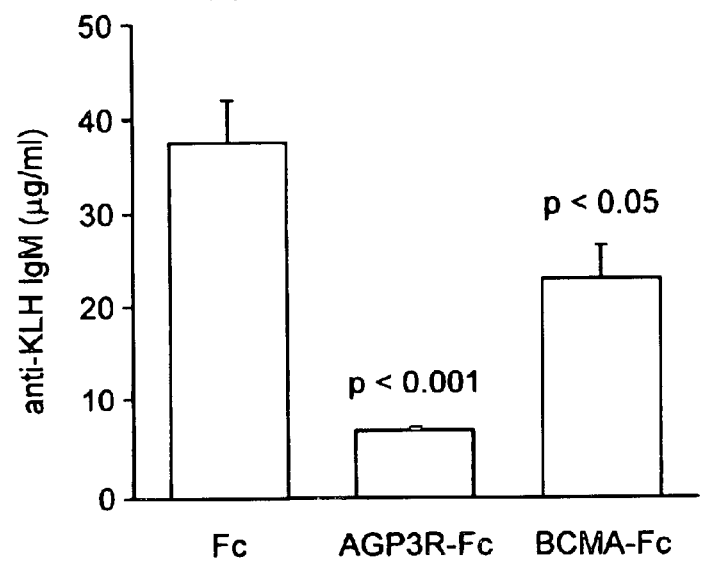
Figure 20C:
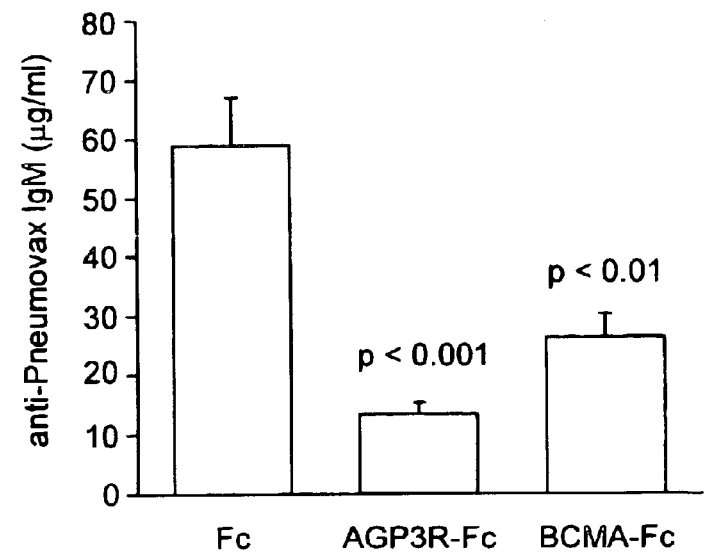

FIG. 20 shows serum levels of anti-KLH IgG and IgM and anti-Pneumovax IgM in mice treated with TACI-Fc or BCMA-Fc fusion proteins or non-fused Fc as a control. p values refer to the comparison with the Fc-treated group. n=7. See Materials and Methods hereinafter.

FIG. 21 shows the sequence of Fc linked human APRIL (SEQ ID NO: 31).

FIG. 22 shows the effect of Fc-humanAPRIL and soluble humanAGP3/BlyS/Tall-1 on proliferation of primary murine B cells. Purified murine spleen B cells were cultured in presence of various amounts of human Fc-APRIL and untagged AGP3 plus 2 µg/ml of anti-IgM. Data show incorporation of $^3$H thymidine as cpm,and represent mean of triplicate wells.

Figure 23:
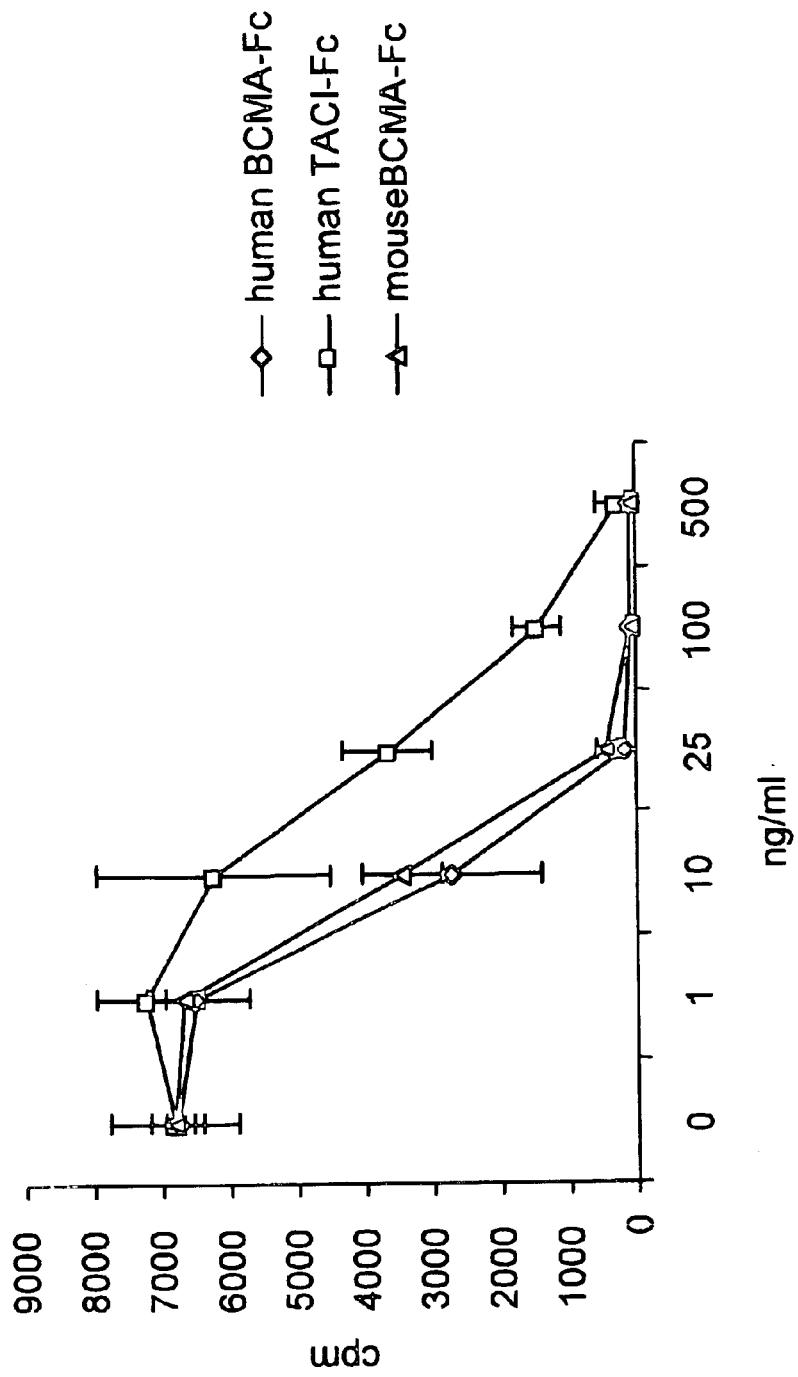

FIG. 23 shows that hBCMA-Fc and hTACI-Fc inhibits Flag-mAPRIL mediated mouse B cell proliferation. Purified murine spleen B cells were cultured with the indicated amounts of soluble BCMA-Fc and TACI-Fc in presence of 10 ng/ml of Flag-mAPRIL and 2 µg/ml of an anti-IgM for 72 hr. Incorporation of $^3$H thymidine is indicated as cpm. Data shown represent mean of triplicate wells.

FIG. 24 shows that administration of hBCMA-Fc (15 mg/kg intraperitoneally (ip__on day 0, 3, and 6) reduces mouse peripheral blood B cell levels measured at day seven. Normal mice (n=7) were treated with human BCMA-Fc and nonfused Fc as a control in day 0,3, and 6 (15 mg/kg). Peripheral blood B cell levels were measured on day 7.

FIG. 25 shows that administration of hBCMA-Fc (15 mg/kg ip on day 0, 3, and 6) reduces mouse spleen B cell levels measured at day seven.

FIG. 26 shows that Flag-mAPRIL and hAGP3 mediated IgA production is inhibited by hBCMA-Fc and hTACI-Fc in vitro. Purified murine spleen B cells were cultured with LPS (100 ng/ml),AGP3 (10 ng/ml),Flag-APRIL (10 ng/ml) or plus BCMA-Fc (100 ng/ml) and TACI-Fc (100 ng/ml) for 12 days. Culture supernatants were collected on day 7 and day 12 for detecting IgA level.

FIG. 27 shows that Flag-mAPRIL and hAGP3 mediated IgG production is inhibited by hBCMA-Fc and hTACI-Fc in vitro.

Figure 28:
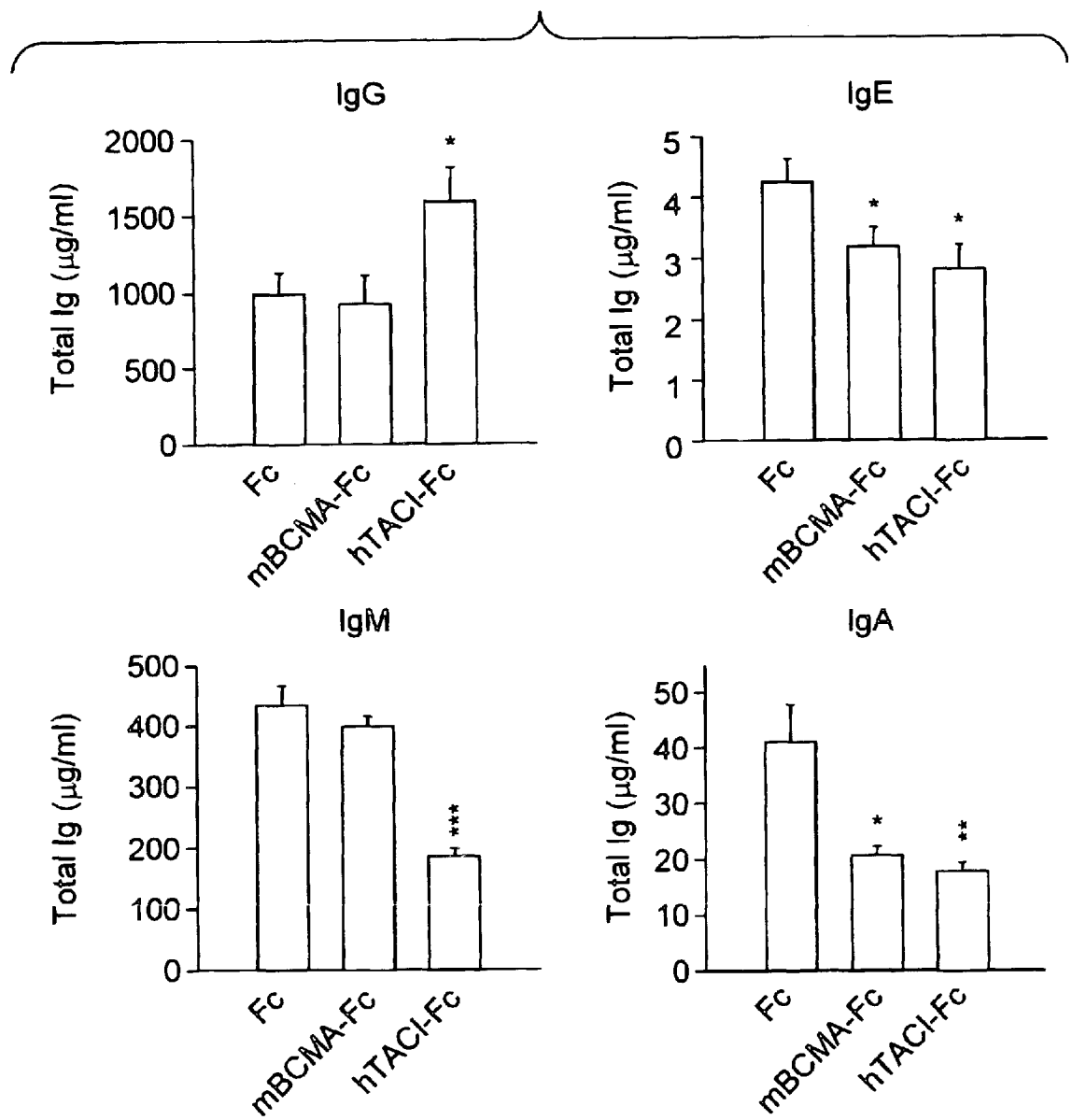

FIG. 28 shows reduced total IgE and IgA levels in normal mice treated with mBCMA-Fc and truncated hTACI-Fc (5 mg/kg ip day 0, 3, and 6). Normal mice (n=7) were treated with human BCMA-Fc, truncated TACI-Fc and nonfused Fc as a control in day 0, 3, and 6 (5 mg/kg). Immunoglobulin levels in serum were measured on day 7.

Figure 29:
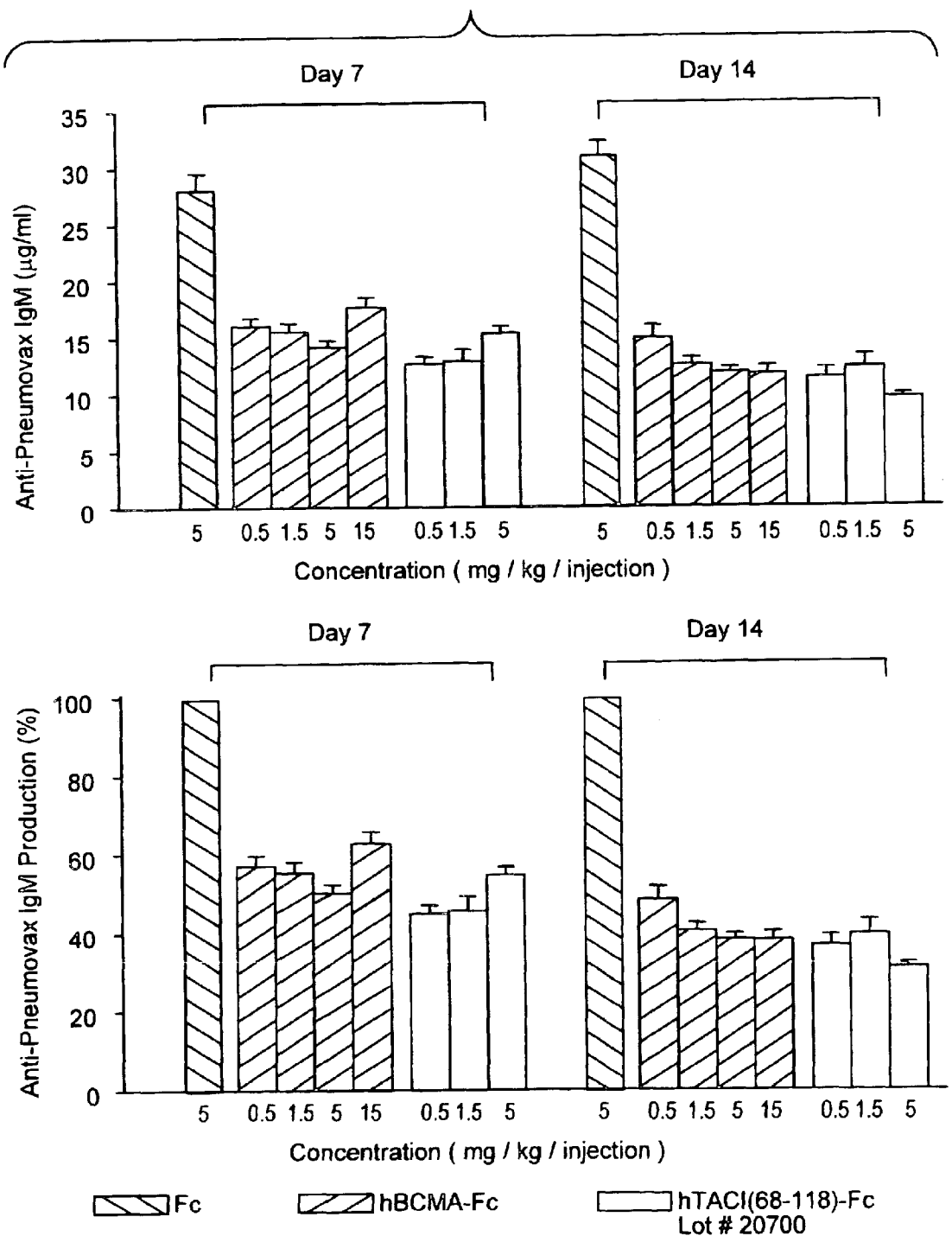

FIG. 29 shows that treatment with hBCMA-Fc or truncated-hTACI-Fc reduces anti-Pneumovacs specific IgM levels in normal mice. Normal mice (n=7) were treated with human BCMA-Fc, truncated TACI-Fc and nonfused Fc as a control in daily doses of 0.5 mg/kg to 15 mg/kg for 7 days. At preimmunization anti-KLH and anti-Pneumovax were undetectable. Antibodies were measured on day 7 and day 14.

Figure 30:
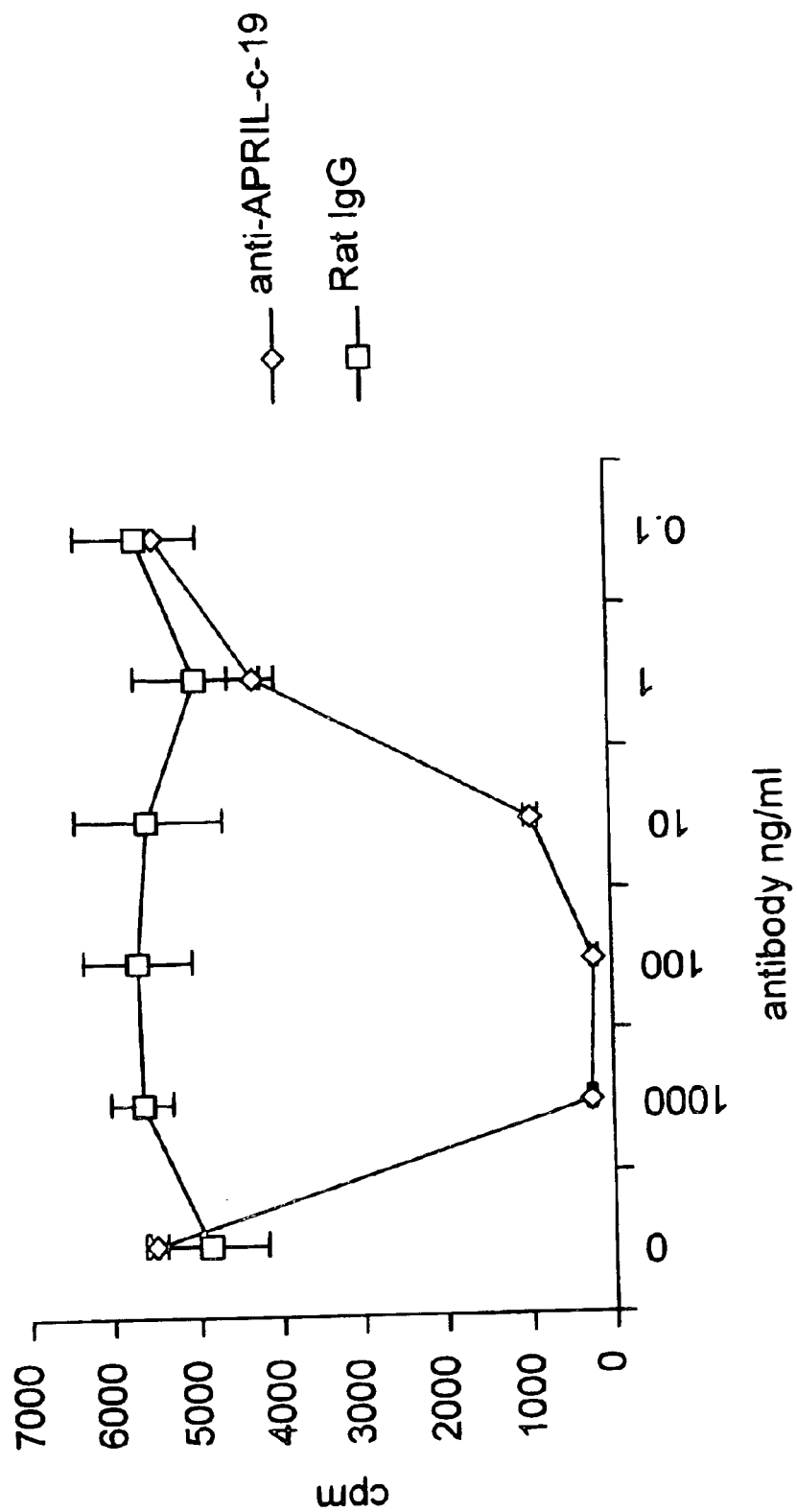

FIG. 30 shows that the anti-mAPRIL specific monoclonal antibody #c19 inhibits Flag-rnAPRIL mediated mouse B cell proliferation. Purified murine spleen B cells were cultured in presence 10 ng/ml mFlag-APRIL plus 2 ug/ml of anti-IgM. anti-Flag-APRIL monoclonal antibody c-19 and rat IgG control were added into culture in same time. Data show incorporation of $^3$H thymidine as cpm, and represent mean of triplicate wells.

Figure 31:
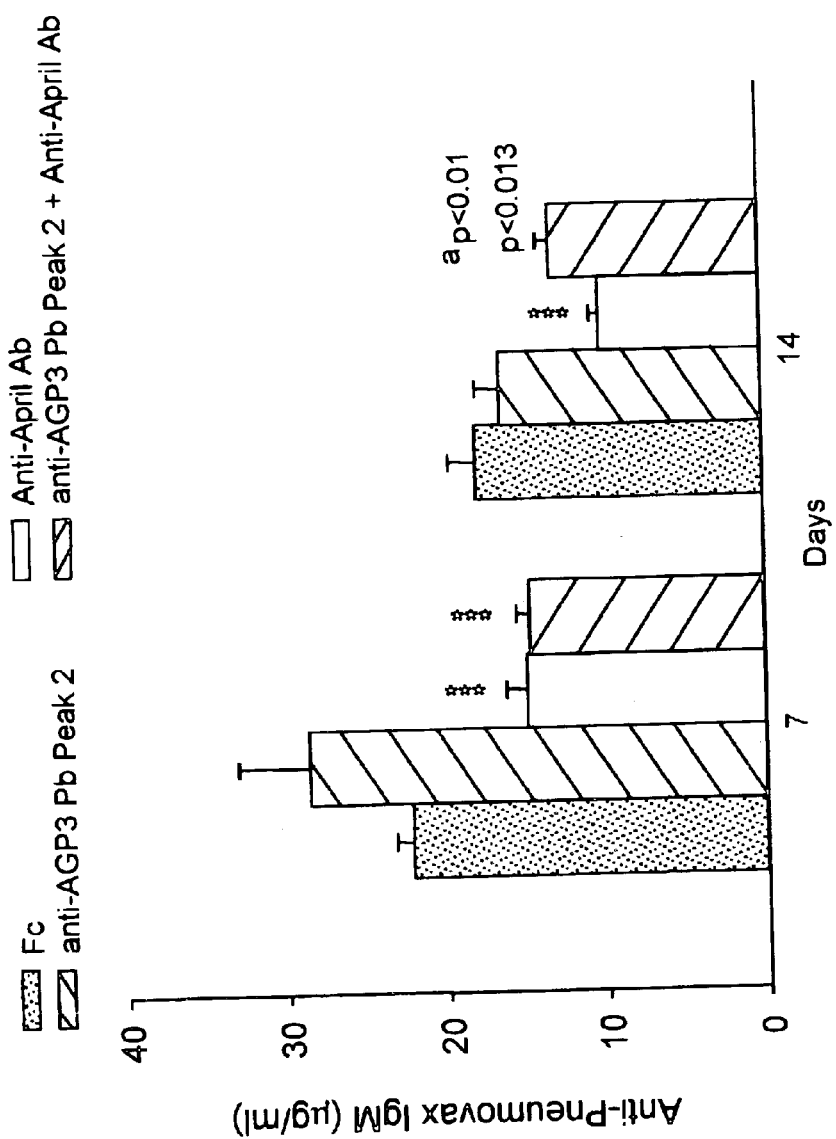

FIG. 31 shows that treatment with the anti-mAPRIL specific monoclonal antibody #c19 inhibits generation of anti-Pneumovacs specific antibodies in vivo.

Figure 32:
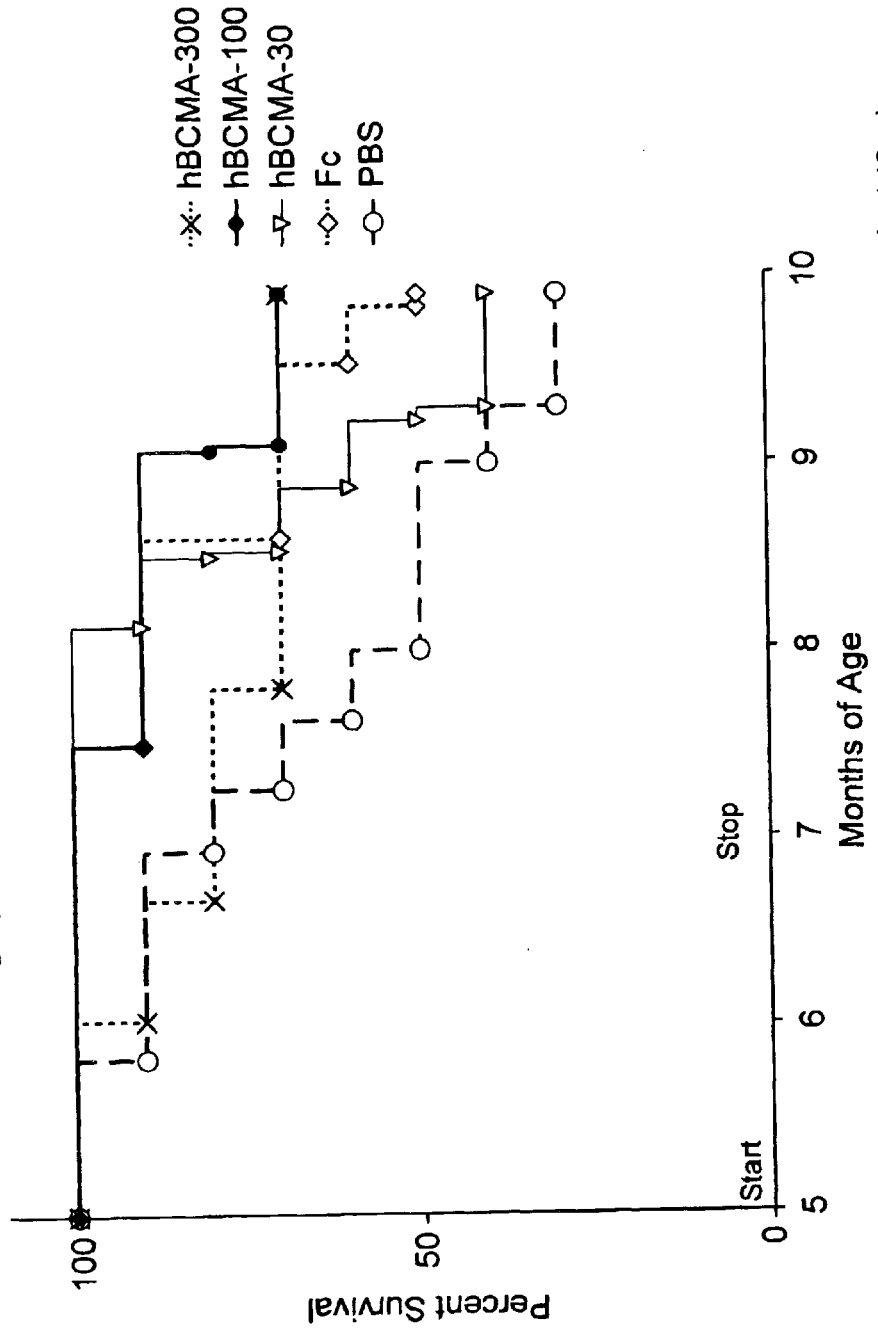

FIG. 32 shows that that treatment with hBCMA-Fc increases survival in the NZB/NZWF1 mouse model of SLE.

Figure 33:
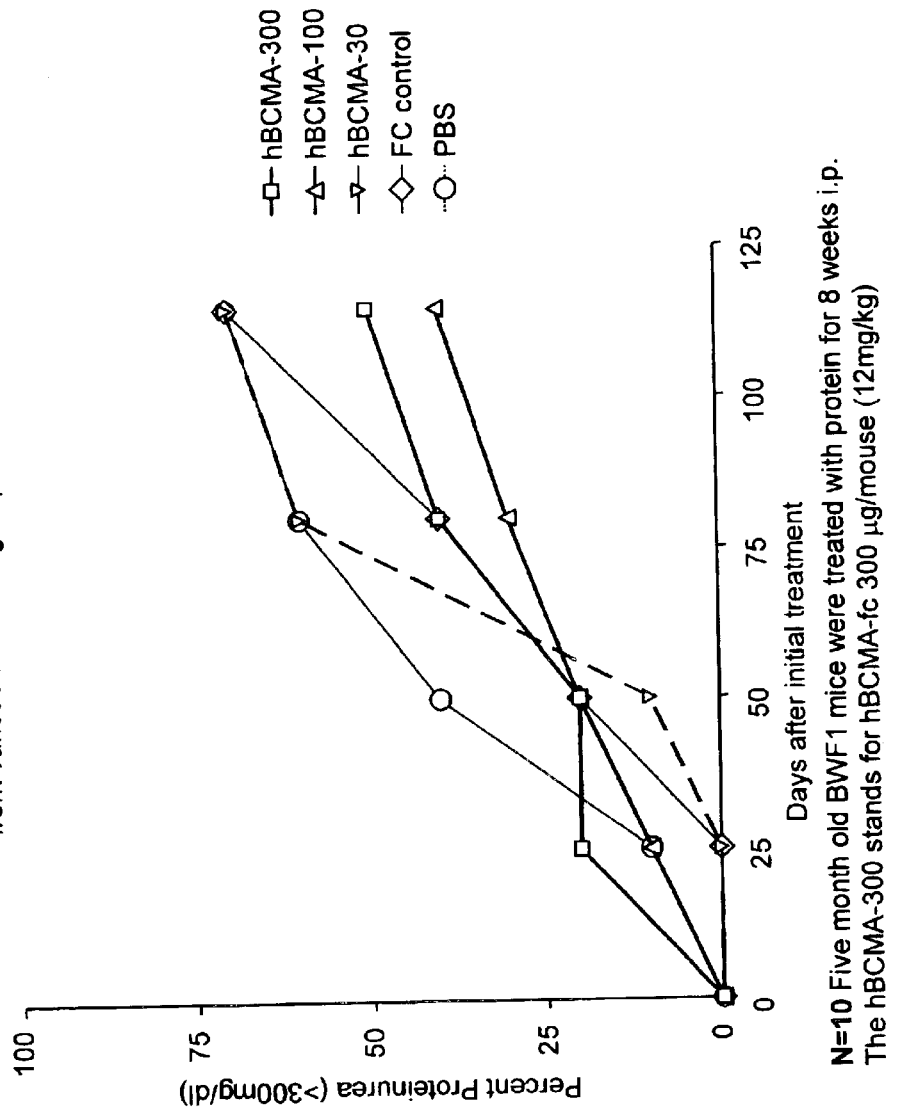

FIG. 33 shows that that treatment with hBCMA-Fc reduces the incidence of proteinurea in the NZB/NZWF1 mouse model of SLE.

FIG. 34 shows that treatment with hBCMA-Fc decreases anti-dsDNA specific antibody levels in the NZB/NZWF1 mouse model of SLE.

FIG. 35 shows that that treatment with hBCMA-Fc decreases peripheral blood % B cells in the NZB/NZWF1 mouse model of SLE.

FIG. 36 shows that APRIL binds to a number of tumor cell lines. APRIL binding to human tumor cell lines were determined by incubating cell with lug/ml Fc-APRIL or Flag-APRIL following FITC labeled secondary antibody staining and FACS analysis.

Figure 37:
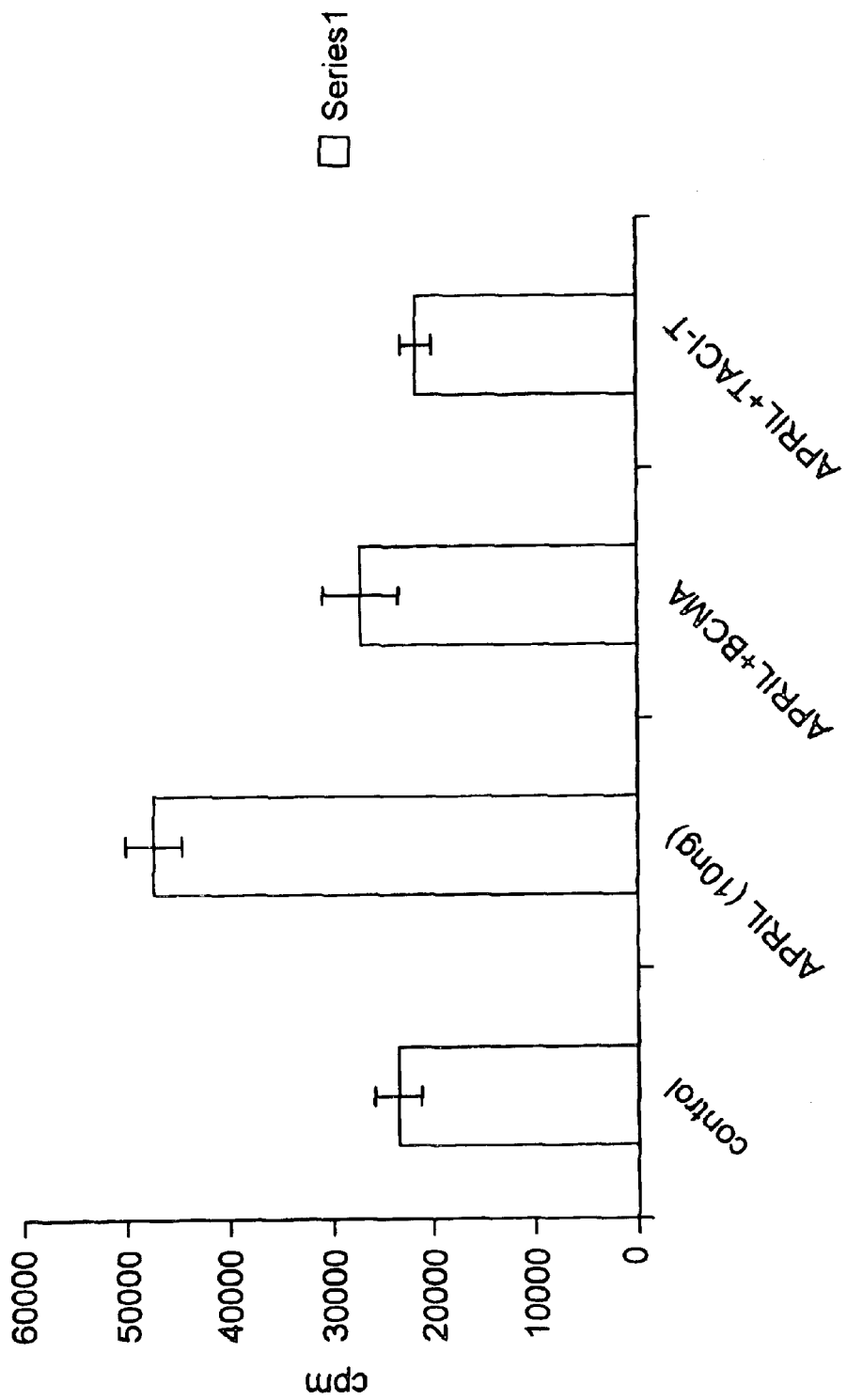

FIG. 37 shows that APRIL stimulates U266-B1 cell growth and that this can be inhibited by BCMA-Fc or TACI-Fc. U266 cells were cultured in presence 10 ng/ml human Fc-APRIL or plus 50 ng/ml soluble BCMA-Fc, Truncated TACI-Fc for 48 hr. Incorporation of $^3$H thymidine is indicated as cpm. Data shown represent mean of triplicate wells.

Figure 38:
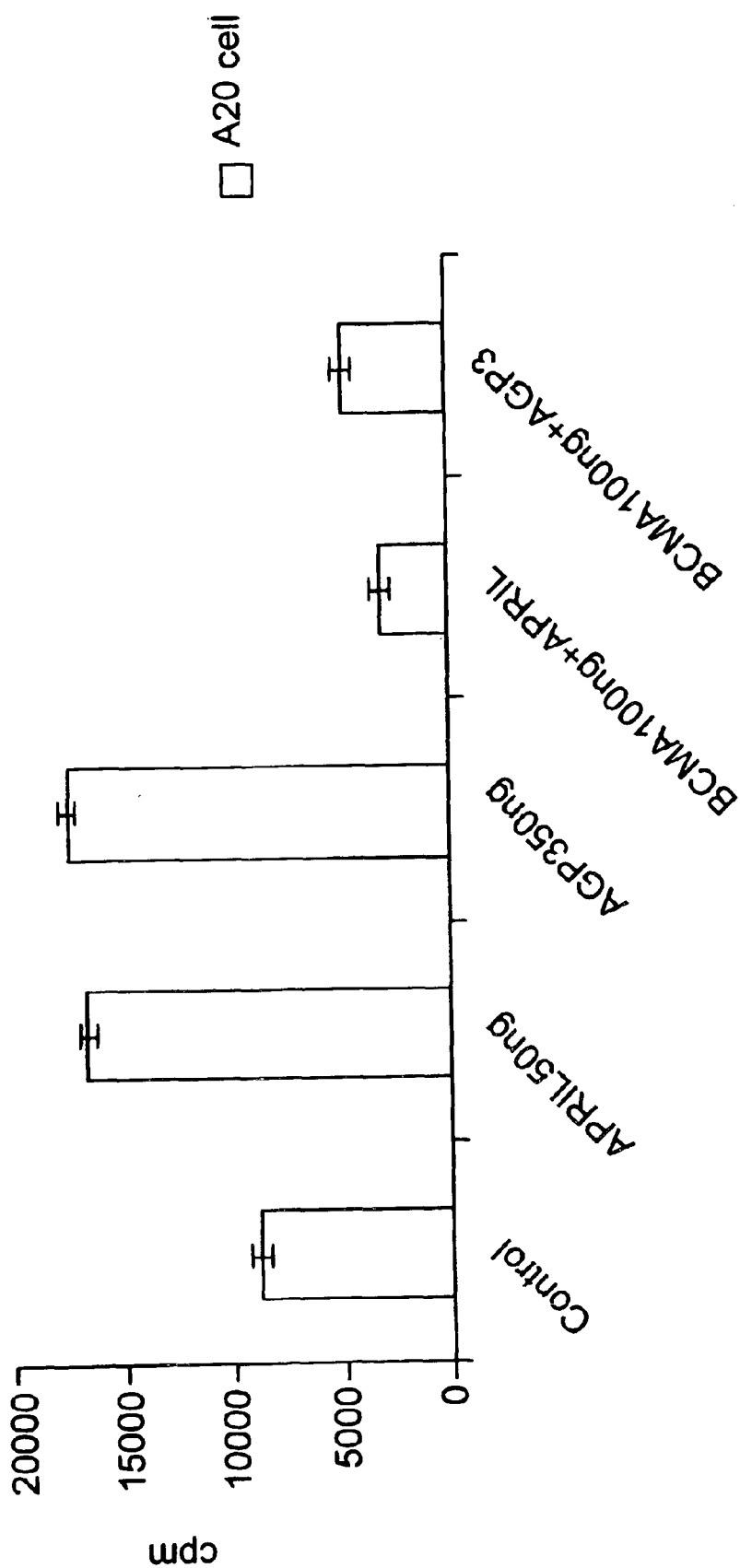

FIG. 38 shows that APRIL stimulates mouse B lymphoma A20 cell growth and that this can be inhibited by BCMA-Fc or TACI-Fc. A20 mouse B cell lymphoma were cultured in presence 50 ng/ml mouse Flag-APRIL, human Flag-AGP3 or plus 100 ng/ml soluble BCMA-Fc for 48 hr. Incorporation of $^3$H thymidine is indicated as cpm. Data shown represent mean of triplicate wells.

Figure 39:
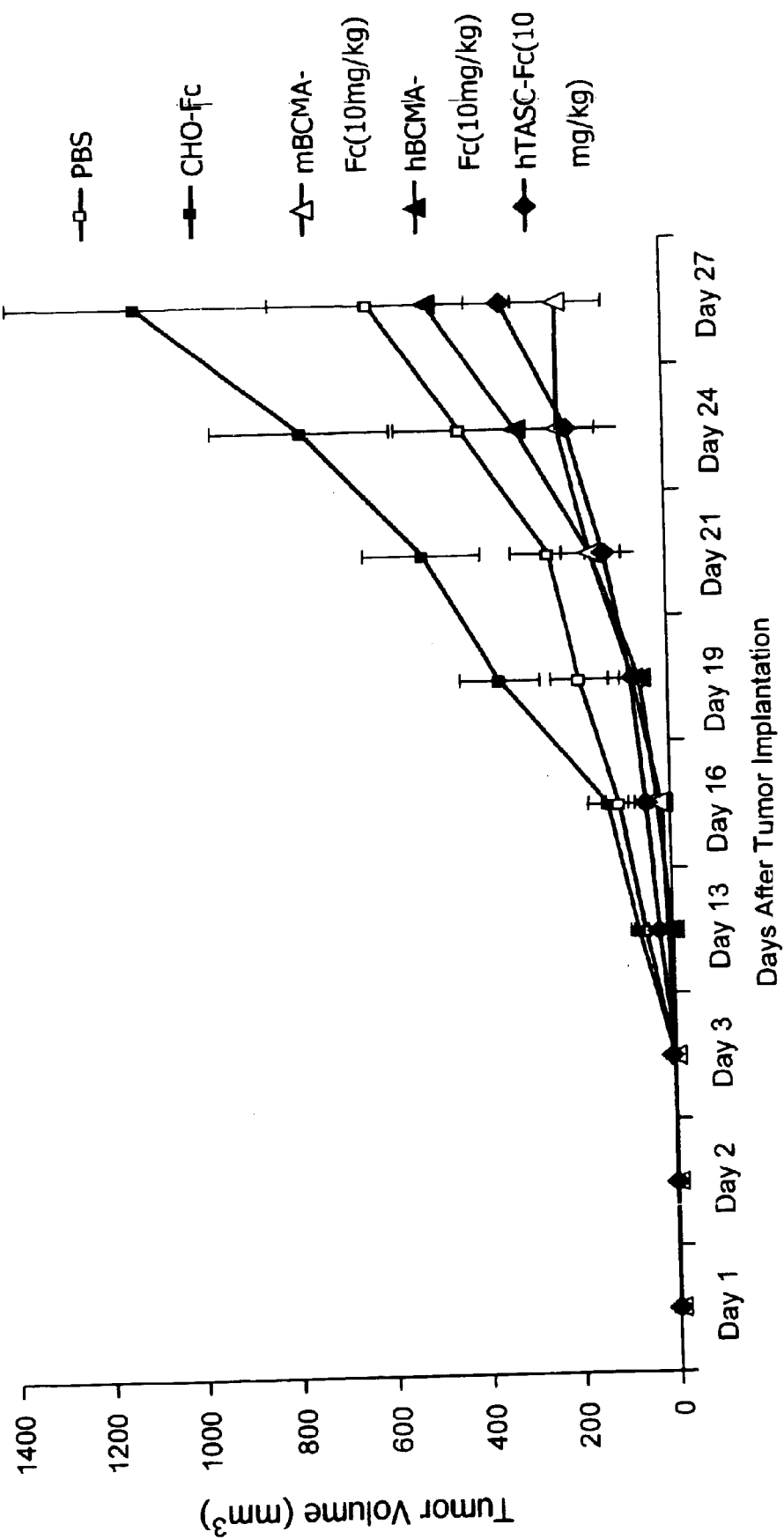

FIG. 39 shows that treatment with BCMA-Fc reduces A20 B lymphoma tumor cell growth in Balb/c mice. A20 (0.2 million) cells were implanted, id, on day 0. Treatments with PBS, CHO-Fc, mBCMA-Fc, hBCMA-Fc, mTACI-Fc, hTACI-Fc were given (10 mg/kg, ip) on days 0, 7, 10, 13, 16, 19, 22. Tumor measurements were made twice per week. Mice were sacrificed on days 27–31, tumors were snap frozen for RNA isolation, blood was collected and serum samples were frozen.

Figure 40:
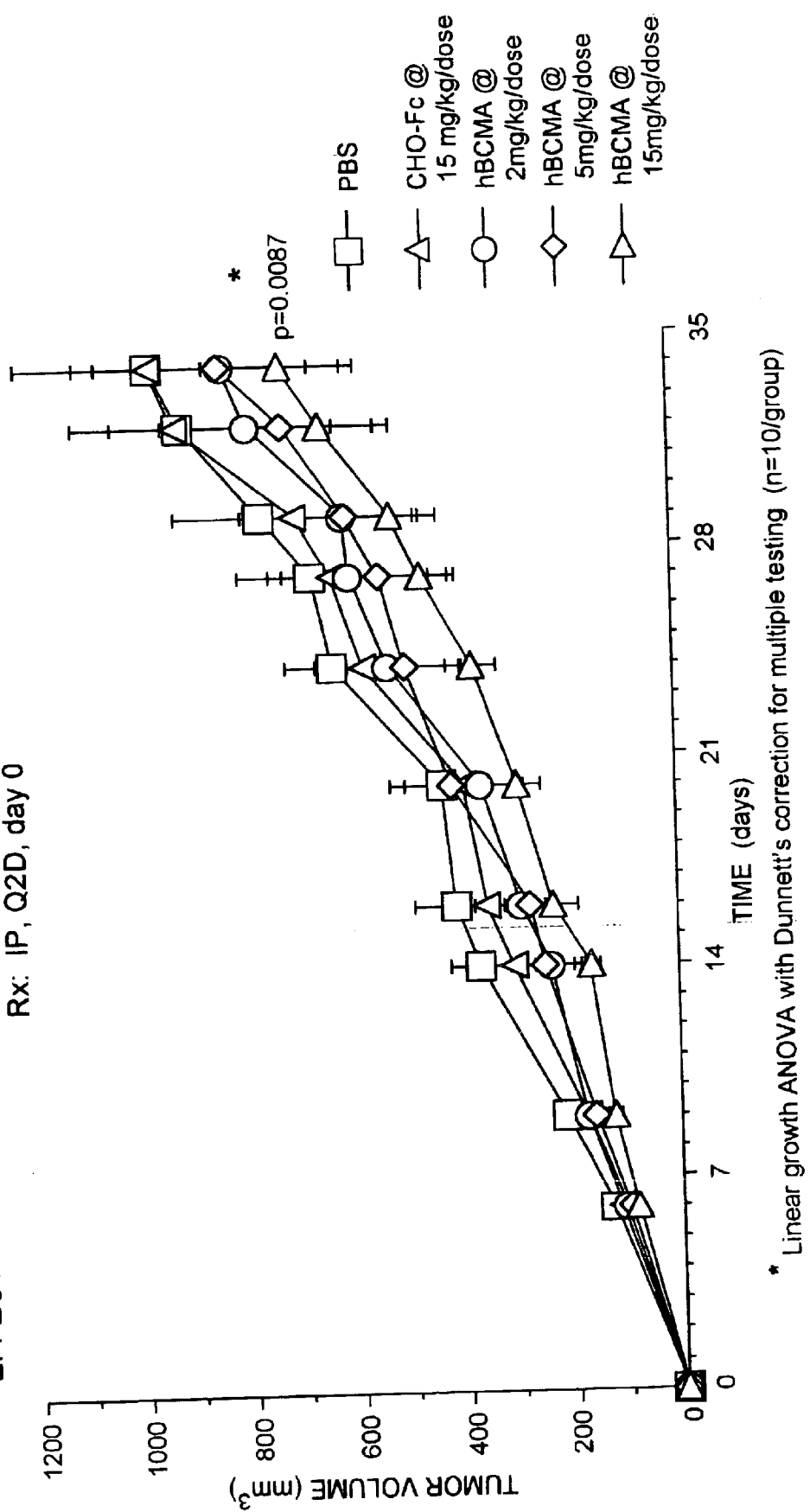

FIG. 40 shows that treatment with hBCMA-Fc reduces human colon carcinoma cell line HT29 tumor volume growth in mice. $2 \times 10^6$ cells plus 50% matrigel injected subcutaneously into athymic nude mice. Rx: human BCMA-Fc at 2,5, and 15 mg/kg Q2D, starting at day 0 (n=10/group). Control 1: CHO-Fc at 15 mg/kg Q2D. Control 2: 0.2 ml of PBS Q2D IP. Tumor volume: 3/week, from day 7. Tumor weight at end of study. Body weight 2/week.

Figure 41:
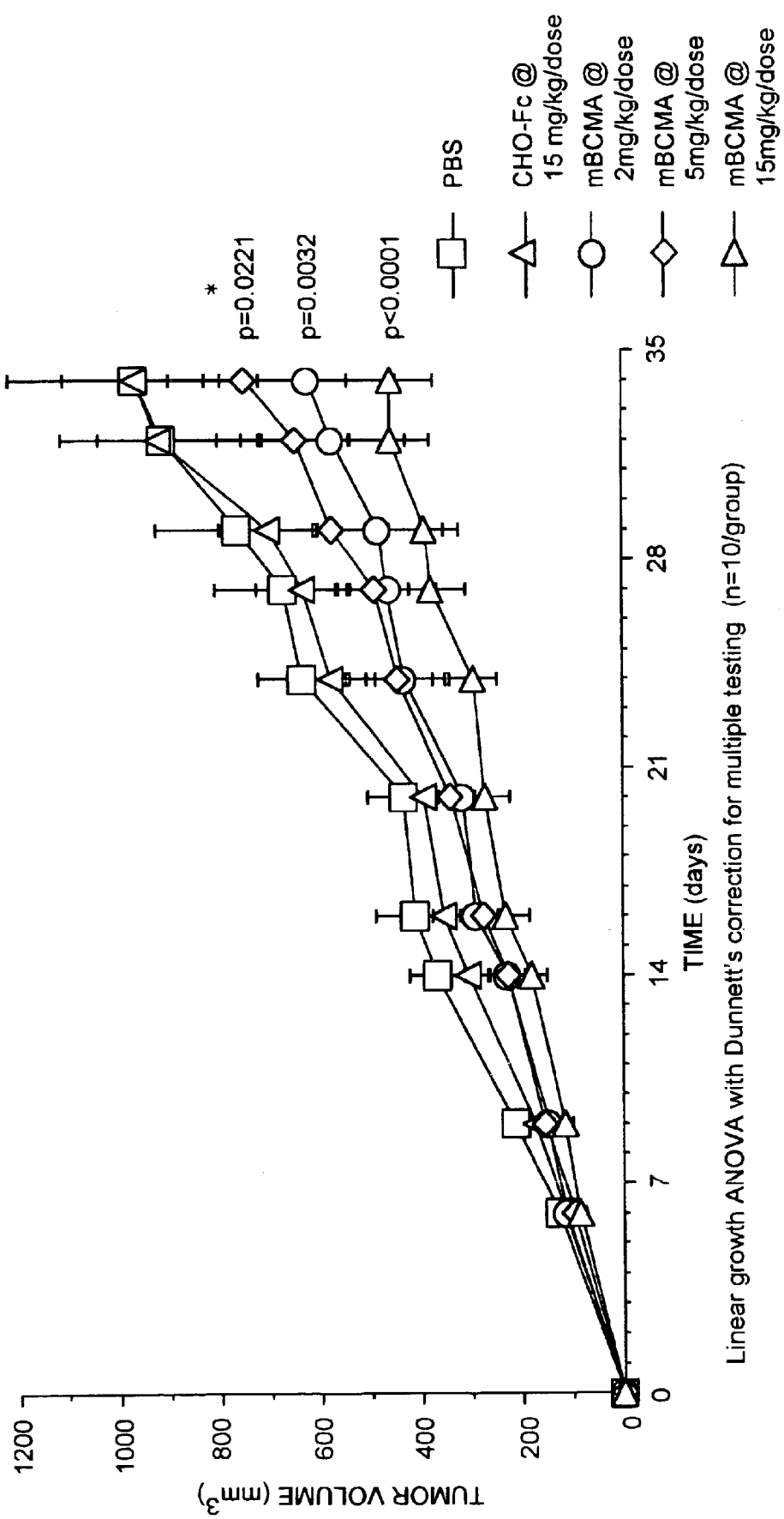

FIG. 41 shows that treatment with mBCMA-Fc reduces human colon carcinoma cell line HT29 tumor volume growth in mice. $2 \times 10^6$ cells plus 50% matrigel injected subcutaneously into athymic nude mice. Rx: mouse BCMA-Fc at 2,5, and 15 mg/kg Q2D, starting at day 0 (n=10/group). Control 1: CHO-Fc at 15 mg/kg Q2D. Control 2: 0.2 ml of PBS Q2D IP. Tumor volume: 3/week, from day 7. Tumor weight at end of study. Body weight 2/week.

DETAILED DESCRIPTION OF THE INVENTION

Definition of Terms

The terms used throughout this specification are defined as follows, unless otherwise limited in specific instances.

The term "comprising" means that a compound may include additional amino acids on either or both of the N- or C-termini of the given sequence. Of course, these additional amino acids should not significantly interfere with the activity of the compound.

"AGP-3 activity" refers to modulation of cell growth, survival, or activation resulting from binding by natural human AGP-3 to TACI or BCMA, particularly in B cells. Conversely, "AGP-3 antagonist activity" refers to activity in opposition to AGP-3 activity, as would result, for example, by inhibition of binding of AGP-3 to TACI or BCMA. Such activity can be determined, for example, by such assays as described in "Biological activity of AGP-3" in the Materials & Methods of PCT/US00/03653, which is hereby incorporated by reference. Additional assays by which AGP-3 activity may be identified appear in the references WO 98/18921 (May 7, 1998); WO 98/27114 (Jun. 25, 1998); EP 869 180 (Oct. 7, 1998); WO 98/55620 and WO 98/55621 (Dec. 10, 1998); WO 99/11791 (Mar. 11, 1999); WO99/12964 (Mar. 18, 1999); and Gross et al. (2000), *Nature* 404: 995–9. Any of the assays described therein may be modified as needed by methods known to persons having ordinary skill in the art.

"APRIL activity" refers to modulation of cell growth, survival, or activation resulting from binding of natural human APRIL to TACI or BCMA, particularly in T cells. Conversely, "APRIL antagonist activity" refers to activity in opposition to APRIL activity, as would result, for example, by inhibition of binding of APRIL to TACI or BCMA. Such activity can be determined, for example, by such assays as described in the Materials & Methods hereinafter. Additional assays by which APRIL activity may be identified appear in the references WO 99/00518 (Jun. 26, 1997); WO 99/11791 (Sep. 5, 1997); WO 99/12965 (Sep. 12, 1997); EP 911 633 (Oct. 8, 1997); EP 919 620 (Nov. 26, 1997); WO 99/28462 (Dec. 3, 1997); WO 99/33980 (Dec. 30, 1997); WO 99/35170 (Jan. 5, 1998); and Hahne et al. (1998), *J. Exp. Med.* 188: 1185–90. Any of the assays described therein and herein may be modified as needed by methods known to persons having ordinary skill in the art.

"BCMA activity" refers to modulation of cell growth, survival, or activation resulting from binding by natural human APRIL or natural human AGP-3 to BCMA. Conversely, "BCMA antagonist activity" refers to activity in opposition to BCMA activity, as would result, for example, by inhibition of binding of AGP-3 or APRIL to BCMA. Such activity can be determined, for example, by such assays as described in the Materials & Methods hereinafter. Additional assays by which BCMA activity may be identified appear in the references WO 99/00518 (Jun. 26, 1997); WO 99/11791 (Sep. 5, 1997); WO 99/12965 (Sep. 12, 1997); EP 911 633 (Oct. 8, 1997); EP 919 620 (Nov. 26, 1997); WO 99/28462 (Dec. 3, 1997); WO 99/33980 (Dec. 30, 1997); WO 99/35170 (Jan. 5, 1998); Hahne et al. (1998), *J. Exp. Med.* 188:1185–90; WO 98/18921 (May 7, 1998); WO 98/27114 (Jun. 25, 1998); EP 869 180 (Oct. 7, 1998); WO 98/55620 and WO 98/55621 (Dec. 10, 1998); WO 99/11791 (Mar. 11, 1999); WO99/12964 (Mar. 18, 1999); and Gross et al. (2000), *Nature* 404: 995–9. Any of the assays described therein and herein may be modified as needed by methods known to persons having ordinary skill in the art.

"TACI activity" refers to modulation of cell growth, survival, or activation resulting from binding by natural human AGP-3 or natural human APRIL to TACI. Conversely, "TACI antagonist activity" refers to activity in opposition to TACI activity, as would result, for example, by inhibition of binding of AGP-3 or APRIL to TACI. Such activity can be determined, for example, by such assays as described in the Materials & Methods of PCT/US00/03653, WO 98/18921 (May 7, 1998), WO 98/27114 (Jun. 25, 1998), EP 869 180 (Oct. 7, 1998), WO 98/55620 and WO 98/55621 (Dec. 10, 1998), WO 99/11791 (Mar. 11, 1999), WO99/12964 (Mar. 18, 1999), WO 98/39361 (Sep. 11, 1998), von Bulow & Bram (1997), *Science,* 278:138–140, and Gross et al. (2000), *Nature* 404: 995–9. Any of the assays described therein may be modified as needed by methods known to persons having ordinary skill in the art.

The term "specific binding partner" refers to any molecule that preferentially binds to a protein of interest, regardless of the antagonistic or agonistic activity of the molecule toward the protein of interest. Exemplary specific binding partners include antibodies, solubilized receptors, peptides, modified peptides as described hereinafter, and the like.

The term "vehicle" refers to a molecule that prevents degradation and/or increases half-life, reduces toxicity, reduces immunogenicity, or increases biological activity of a therapeutic protein. Exemplary vehicles include an Fc domain (which is preferred) as well as a linear polymer (e.g., polyethylene glycol (PEG), polylysine, dextran, etc.); a branched-chain polymer (see, for example, U.S. Pat. No. 4,289,872 to Denkenwalter et al, issued Sep. 15, 1981; U.S. Pat. No. 5,229,490 to Tam, issued Jul. 20, 1993; WO 93/21259 by Frechet et al., published Oct. 28, 1993); a lipid; a cholesterol group (such as a steroid); a carbohydrate or oligosaccharide; or any natural or synthetic protein, polypeptide or peptide that binds to a salvage receptor. Vehicles are further described hereinafter.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgAl1, IgGA2). One example of a native Fc is a disulfide-bonded dimer resulting from papain digestion of an IgG (see Ellison et al. (1982), *Nucleic Acids Res.* 10: 4071–9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail in WO 00/24782, published May 4, 2000, which is hereby incorporated by reference in its entirety.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by other means.

The term "multimer" as applied to Fc domains or molecules comprising Fc domains refers to molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently.

The terms "derivatizing" and "derivative" or "derivatized" comprise processes and resulting compounds respectively in which (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —NRR$^1$, NRC(O)R$^1$, —NRC(O)OR$^1$, —NRS(O)$_2$R$^1$, —NHC(O)NHR, a succinimide group, or substituted or unsubstituted benzyloxycarbonyl-NH—, wherein R and R$^1$ and the ring substituents are as defined hereinafter; (5) the C-terminus is replaced by —C(O)R$^2$ or —NR$^3$R$^4$ wherein R$^2$, R$^3$ and R$^4$ are as defined hereinafter; and (6) compounds in which individual amino acid moieties are modified through treatment with agents capable of reacting with selected side chains or terminal residues. Derivatives are further described hereinafter.

The term "peptide" refers to molecules of 2 to 40 amino acids, with molecules of 3 to 20 amino acids preferred and those of 6 to 15 amino acids most preferred. Exemplary peptides may be randomly generated by any of the methods cited above, carried in a peptide library (e.g., a phage display library), or derived by digestion of proteins.

The term "randomized" as used to refer to peptide sequences refers to fully random sequences (e.g., selected by phage display methods) and sequences in which one or more residues of a naturally occurring molecule is replaced by an amino acid residue not appearing in that position in the naturally occurring molecule. Exemplary methods for identifying peptide sequences include phage display, E. coli display, ribosome display, yeast-based screening, RNA-peptide screening, chemical screening, rational design, protein structural analysis, and the like. Randomized peptides and methods of generating them appear in WO 00/24782, published May 4, 2000, which is hereby incorporated by reference in its entirety.

The term "pharmacologically active" means that a substance so described is determined to have activity that affects a medical parameter (e.g., T cell proliferation) or disease state (e.g., cancer, autoimmune disorders). Thus, pharmacologically active compounds comprise agonistic or mimetic and antagonistic compounds as defined below.

The terms "-mimetic" and "agonist" refer to a molecule having biological activity comparable to a protein (e.g., APRIL, AGP-3) that interacts with a protein of interest. These terms further include molecules that indirectly mimic the activity of a protein of interest, such as by potentiating the effects of the natural ligand of the protein of interest.

The terms "antagonist" or "inhibitor" refer to a molecule that blocks or in some way interferes with the biological activity of the associated protein of interest, or has biological activity comparable to a known antagonist or inhibitor of the associated protein of interest.

Additionally, physiologically acceptable salts of the compounds of this invention are also encompassed herein. By "physiologically acceptable salts" is meant any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate.

Methods of Treatment

The present invention concerns a method of inhibiting T cell proliferation in a mammal, which comprises administering a therapeutic agent comprising:
a. a specific binding partner for TACI, wherein the specific binding partner has TACI antagonist activity;
b. a specific binding partner for BCMA, wherein the specific binding partner has BCMA antagonist activity;
c. both a and b; or
d. a specific binding partner for TACI and BCMA, wherein the specific binding partner has TACI antagonist activity, BCMA antagonist activity or both.

The present invention also concerns a method of inhibiting APRIL activity in a mammal, which comprises administering a therapeutic agent comprising a through d above.

The invention also concerns a method of inhibiting TACI activity, BCMA activity, or both in a mammal, which comprises administering a specific binding partner for APRIL. This method may further comprise administering a specific binding partner for AGP-3.

Some indications benefit from an increase in the immune response. Accordingly, the invention further relates to a method of increasing T cell proliferation in a mammal, which comprises administering a therapeutic agent comprising:
a. a specific binding partner for TACI, wherein the specific binding partner has TACI agonist activity;
b. a specific binding partner for BCMA, wherein the specific binding partner has BCMA agonist activity;
c. both a and b; or
d. a specific binding partner for TACI and BCMA, wherein the specific binding partner has TACI agonist activity, BCMA agonist activity or both.

The invention also concerns a method of increasing APRIL activity in a mammal, which comprises administering a therapeutic agent comprising a through d above.

The inventors contemplate carrying out the foregoing methods of treatment with any of several different types of molecules, including small molecules, antibodies, and engineered peptides and fusion molecules described hereinafter. These molecules may also be used in assays to identify cells and tissues that express AGP-3, TACI, APRIL, or BCMA. The invention further concerns nucleic acids, vectors, and host cells useful in preparing such molecules.

The invention further concerns methods of identifying compounds that are useful in the aforementioned methods of use. Such compounds include nucleic acids, peptides, proteins, carbohydrates, lipids or small molecular weight organic molecules and may act either as agonists or antagonists of BCMA, TACI, AGP-3 or APRIL-protein activity.

AGP-3, APRIL, BCMA, and TACI are believed to play a role in regulation of immune function. Accordingly, these molecules, their soluble forms, and agonists and antagonists thereof may be useful for the diagnosis and/or treatment of inflammation and immune function diseases. Indications for antagonists include, but are not limited to the following:

infections such as bacterial, fungal, protozoan and viral infections, especially HIV-1 or HIV-2;

diarrhorea;

psoriasis;

inflammation;

allergies;

atopic dermatitis;

respiratory allergic diseases such as asthma, allergic rhinitis, hypersensitivity lung disease, hypersensitivity pneumonitis, eosinophilic pneumonia (e.g. Loeffler's syndrome, chronic eosinophilic pneumonia, interstitial lung disease (ILD), such as idiopathic pulmonary fibrosis or ILD associated with rheumatoid arthritis, systemic lupus erythematosus, ankylosing spondylitis, systemic sclerosis, Sjogren's syndrome, polymyositis or dermatomyositis);

systemic anaphylaxis or hypersensitivity responses;

drug allergy;

insect sting allergy;

inflammatory bowel disease, such as Crohn's disease and ulcerative colitis;

spondyloarthropathy;

scleroderma;

psoriasis;

inflammatory dermatosis such as dermatitis, eczema, atopic dermatitis, allergic contact dermatitis, urticaria, vasculitis (e.g. necrotizing, cutaneous and hypersensitivity vasculitis), eosinphilic myositis and eosinophilic fasciitis;

autoimmune diseases such as rheumatoid arthritis, psoriatic arthritis, multiple sclerosis, systemic lupus erythematosus, myasthenia gravis, juvenile onset diabetes, glomerulonephritis, autoimmune thyroiditis and Behcet's disease;

graft rejection, including allograft rejection or graft-versus-host disease;

cancers with leukocyte infiltration of the skin or organs;

reperfusion injury;

atherosclerosis;

certain haematologic malignancies;

shock, including septic shock and endotoxic shock.

Agonists can be used for treating:

immunosuppression e.g. in AIDS patients or individuals undergoing radiation therapy, chemotherapy, therapy for autoimmune disease or other drug therapy, and immunosuppression due congenital deficiency in receptor function or other causes; and infectious diseases such as parasitic diseases, including helminth infections, such as nematodes (round worms).

Compositions of Matter

Any number of molecules may serve as specific binding partners within the present invention. Of particular interest are antibodies, peptides, and Fc-peptide fusion molecules.

Antibodies.

The invention also provides for an antibody or antigen binding domain thereof, or a fragment, variant, or derivative thereof, which binds to an epitope on any of the target molecules (APRIL, AGP-3, TACI, or BCMA) and has partial or complete agonist or antagonist activity. Preferably, the target molecule is mammalian, more preferably human, and may be in soluble or cell surface associated forms, or fragments, derivatives and variants thereof.

A number of methods for antibody generation are known in the art. All such methods are useful in generating molecules useful in accordance with the present invention. Conventionally, an antibody may be prepared by immunizing an animal with the target molecule (e.g., murine or human BCMA or TACI) or with an immunogenic fragment, derivative or variant thereof. In addition, an animal may be immunized with cells transfected with a vector containing a nucleic acid molecule encoding the target molecule such that the target molecule is expressed and associated with the surface of the transfected cells. Alternatively, specific binding partners that are antibodies may be obtained by screening a library comprising antibody or antigen binding domain sequences for binding to the target molecule. Such a library is conveniently prepared in bacteriophage as protein or peptide fusions to a bacteriophage coat protein which are expressed on the surface of assembled phage particles and the encoding DNA sequences contained within the phage particles (so-called "phage display library"). In one example, a phage display library contains DNA sequences encoding human antibodies, such as variable light and heavy chains. Sequences binding to the target molecule may be further evolved by multiple rounds of mutagenesis and screening.

Specific binding partners that are antibodies or antigen binding domains may be tetrameric glycoproteins similar to native antibodies, or they may be single chain antibodies; for example, Fv, Fab, Fab' or F(ab)' fragments, bispecific antibodies, heteroantibodies, or other fragments, variants, or derivatives thereof, which are capable of binding the target molecule and partially or completely neutralize the target molecule activity. Antibodies or antigen binding domains may be produced in hybridoma cell lines (antibody-producing cells such as spleen cells fused to mouse myeloma cells, for example) or may be produced in heterologous cell lines transfected with nucleic acid molecules encoding said antibody or antigen binding domain.

Antibodies of the invention include polyclonal monospecific polyclonal, monoclonal, recombinant, chimeric, humanized, fully human, single chain and/or bispecific antibodies. Antibody fragments include those portions of an antibody that bind to an epitope on a target molecule. Examples of such fragments include Fab F(ab'), F(ab)', Fv, and sFv fragments. The antibodies may be generated by enzymatic cleavage of full-length antibodies or by recombinant DNA techniques, such as expression of recombinant plasmids containing nucleic acid sequences encoding antibody variable regions.

Polyclonal antibodies are heterogeneous populations of antibody molecules derived from the sera of animals immunized with an antigen. An antigen is a molecule or a portion of a molecule capable of being bound by an antibody which is additionally capable of inducing an animal to produce antibody capable of binding to an epitope of that antigen. An antigen can have one or more epitope. The specific reaction referred to above is meant to indicate that the antigen will react, in a highly selective manner, with its corresponding antibody and not with the multitude of other antibodies which can be evoked by other antigens.

Polyclonal antibodies directed toward a target molecule generally are raised in animals (e.g., rabbits or mice) by multiple subcutaneous or intraperitoneal injections of the target molecule and an adjuvant. In accordance with the invention, it may be useful to conjugate the target molecule, or a variant, fragment, or derivative thereof to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. After immunization, the animals are bled and the serum is assayed for anti-target antibody titer.

Monoclonal antibodies (mAbs) contain a substantially homogeneous population of antibodies specific to antigens, which population contains substantially similar epitope binding sites. Such antibodies may be of any immunoglobulin class including IgG, IgM, IgE, IgA, IgD and any subclass thereof. A hybridoma producing a monoclonal antibody of the present invention may be cultivated in vitro, in situ, or in vivo. Production of high titers in vivo or in situ is a preferred method of production.

Monoclonal antibodies directed toward the target molecule are produced using any method which provides for the production of antibody molecules by continuous cell lines in culture. Examples of suitable methods for preparing monoclonal antibodies include hybridoma methods of Kohler et al., *Nature* 256, 495–497 (1975), and the human B-cell hybridoma method, Kozbor, *J. Immunol.* 133, 3001 (1984); Brodeur et al., Monoclonal Antibody Production Techniques and Applications, pp. 51–63 (Marcel Dekker, Inc., New York, 1987); and Harlow and Lane, Antibodies: A Laboratory Manual, Cold Spring Harbor Laboratory (1988); the contents of which references are incorporated entirely herein by reference.

Preferred specific binding partners include monoclonal antibodies which will inhibit partially or completely the binding of the human target molecule to its cognate ligand or receptor or an antibody having substantially the same specific binding characteristics, as well as fragments and regions thereof. Preferred methods for determining monoclonal antibody specificity and affinity by competitive inhibition can be found in Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, *Meth. Enzymol.*, 92:589–601 (1983). Each of these references is incorporated herein by reference in its entirety.

Also provided by the invention are hybridoma cell lines which produce monoclonal antibodies reactive with target polypeptides.

Chimeric antibodies are molecules in which different portions are derived from different animal species, such as those having a variable region derived from a murine monoclonal antibody and a human immunoglobulin constant region. Chimeric antibodies are primarily used to reduce immunogenicity in application and to increase yields in production, for example, where murine monoclonal antibodies have higher yields from hybridomas but higher immunogenicity in humans, such that human/murine chimeric monoclonal antibodies are used.

Chimeric antibodies and methods for their production are known in the art. Cabilly et. al. *Proc. Natl. Acad. Sci. USA,* 81:3273–3277 (1984); Morrison et al., *Proc. Natl. Acad. Sci. USA,* 81:6851–6855 (1984); Boulianne et al., *Nature,* 312:643–646 (1984); Neuberger et al., *Nature,* 314:268–270 (1985); Liu et al., *Proc. Natl. Acad. Sci. USA,* 84:3439–3443 (1987); and Harlow and Lane *Antibodies: A Laboratory Manual,* Cold Spring Harbor Laboratory (1988). These references are incorporated herein by reference in their entirety.

A chimeric monoclonal antibody of the invention may be used as a therapeutic agent. In such a chimeric antibody, a portion of the heavy and/or light chain is identical with or homologous to corresponding sequence in antibodies derived from a particular species or belonging to one particular antibody class or subclass, while the remainder of the chain(s) is identical with or homologous to corresponding sequence in antibodies derived from another species or belonging to another antibody class or subclass, as well as fragments of such antibodies, so long as they exhibit the desired biological activity (see U.S. Pat. No. 4,816,567; Morrison et al., *Proc. Natl. Acad. Sci.* 81, 6851–6855 (1985).

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a $C_H$ region that aggregates (e.g., from an IgM H chain, or $\mu$ chain).

Murine and chimeric antibodies, fragments and regions of the present invention may comprise individual heavy (H) and/or light (L) immunoglobulin chains. A chimeric H chain comprises an antigen binding region derived from the H chain of a non-human antibody specific for the target molecule, which is linked to at least a portion of a human H chain C region ($C_H$), such as $CH_1$ or $CH_2$.

A chimeric L chain according to the present invention comprises an antigen binding region derived from the L chain of a non-human antibody specific for the target molecule, linked to at least a portion of a human L chain C region ($C_L$).

Specific binding partners, such as antibodies, fragments, or derivatives, having chimeric H chains and L chains of the same or different variable region binding specificity, can also be prepared by appropriate association of the individual polypeptide chains, according to known method steps, e.g., according to Ausubel et al., eds. *Current Protocols in Molecular Biology,* Wiley Interscience, N.Y. (1993), and Harlow et al., Antibodies: A Laboratory Manual, Cold Spring Harbor Laboratory Press, Cold Spring Harbor, N.Y. (1988). The contents of these references are incorporated entirely herein by reference. With this approach, hosts expressing chimeric H chains (or their derivatives) are separately cultured from hosts expressing chimeric L chains (or their derivatives), and the immunoglobulin chains are separately recovered and then associated. Alternatively, the hosts can be co-cultured and the chains allowed to associate spontaneously in the culture medium, followed by recovery of the assembled immunoglobulin, fragment or derivative.

As an example, the antigen binding region of the specific binding partner (such as a chimeric antibody) of the present invention is preferably derived from a non-human antibody specific for the human analog of the target molecule. Preferred sources for the DNA encoding such a non-human antibody include cell lines which produce antibodies, such as hybrid cell lines commonly known as hybridomas.

The invention also provides for fragments, variants and derivatives, and fusions of anti-target antibodies, wherein the terms "fragments", "variants", "derivatives" and "fusions" are defined herein. The invention encompasses fragments, variants, derivatives, and fusions of anti-target antibodies which are functionally similar to the unmodified antibody, that is, they retain at least one of the activities of the unmodified antibody. In addition to the modifications set forth above, also included is the addition of genetic sequences coding for cytotoxic proteins such as plant and bacterial toxins. The fragments, variants, derivatives and fusions of the antibodies can be produced from any of the hosts of this invention.

Suitable fragments include, for example, Fab, Fab', F(ab')$_2$, Fv and scFv. These fragments lack the Fc fragment of an intact antibody, clear more rapidly from the circulation, and can have less non-specific tissue binding than an intact antibody. See Wahl et al., *J. Nucl. Med.,* 24:316–325 (1983). These fragments are produced from intact antibodies using methods well known in the art, for example by proteolytic cleavage with enzymes such as papain (to produce Fab fragments) or pepsin (to produce F(ab')$_2$ fragments). The identification of these antigen binding regions and/or epitopes recognized by monoclonal antibodies of the present invention provides the information necessary to generate additional monoclonal antibodies with similar binding characteristics and therapeutic or diagnostic utility that parallel the embodiments of this invention.

Variants of specific binding partners are also provided. In one embodiment, variants of antibodies and antigen binding domains comprise changes in light and/or heavy chain amino acid sequences that are naturally occurring or are introduced by in vitro engineering of native sequences using recombinant DNA techniques. Naturally occurring variants include "somatic" variants which are generated in vivo in the corresponding germ line nucleotide sequences during the generation of an antibody response to a foreign antigen.

Variants of antibodies and antigen binding domains are also prepared by mutagenesis techniques known in the art. In one example, amino acid changes may be introduced at random throughout an antibody coding region and the resulting variants may be screened for a desired activity, such as binding affinity for the target molecule. Alternatively, amino acid changes may be introduced in selected regions of an antibody, such as in the light and/or heavy chain CDRs, and framework regions, and the resulting antibodies may be screened for binding to the target molecule or some other activity. Amino acid changes encompass one or more amino acid substitutions in a CDR, ranging from a single amino acid difference to the introduction of all possible permutations of amino acids within a given CDR, such as CDR3. In another method, the contribution of each residue within a CDR to target binding may be assessed by substituting at least one residue within the CDR with alanine (Lewis et al. (1995), *Mol. Immunol.* 32:

1065–72). Residues which are not optimal for binding to the target molecule may then be changed in order to determine a more optimum sequence. Also encompassed are variants generated by insertion of amino acids to increase the size of a CDR, such as CDR3. For example, most light chain CDR3 sequences are nine amino acids in length. Light chain CDR3 sequences in an antibody which are shorter than nine residues may be optimized for binding to the target molecule by insertion of appropriate amino acids to increase the length of the CDR.

In one embodiment, antibody or antigen binding domain variants comprise one or more amino acid changes in one or more of the heavy or light chain CDR1, CDR2 or CDR3 and optionally one or more of the heavy or light chain framework regions FR1, FR2 or FR3. Amino acid changes comprise substitutions, deletions and/or insertions of amino acid residues.

Variants may also be prepared by "chain shuffling" of either light or heavy chains. Marks et al. (1992), Biotechnology 10: 779–83. Typically, a single light (or heavy) chain is combined with a library having a repertoire of heavy (or light) chains and the resulting population is screened for a desired activity, such as binding to the target molecule. This technique permits screening of a greater sample of different heavy (or light) chains in combination with a single light (or heavy) chain than is possible with libraries comprising repertoires of both heavy and light chains.

The specific binding partners of the invention can be bispecific. Bispecific specific binding partners of this invention can be of several configurations. For example, bispecific antibodies resemble single antibodies (or antibody fragments) but have two different antigen binding sites (variable regions). Bispecific antibodies can be produced by chemical techniques (see e.g., Kranz et al., Proc. Natl. Acad. Sci. USA, 78:5807 (1981)), by "polydoma" techniques (see U.S. Pat. No. 4,474,893 to Reading) or by recombinant DNA techniques. For example, a bispecific antibody in accordance with this invention may bind to APRIL and AGP-3. As another example, a bispecific antibody may bind to TACI and BCMA.

The specific binding partners of the invention may also be heteroantibodies. Heteroantibodies are two or more antibodies, or antibody binding fragments (Fab) linked together, each antibody or fragment having a different specificity.

The invention also relates to "humanized" antibodies. Methods for humanizing non-human antibodies are well known in the art. Generally, a humanized antibody has one or more amino acid residues introduced into a human antibody from a source which is non-human. In general, non-human residues will be present in CDRs. Humanization can be performed following methods known in the art (Jones et al., Nature 321, 522–525 (1986); Riechmann et al., Nature, 332, 323–327 (1988); Verhoeyen et al., Science 239, 1534–1536 (1988)), by substituting rodent complementarily-determining regions (CDRs) for the corresponding regions of a human antibody.

The specific binding partners of the invention, including chimeric, CDR-grafted, and humanized antibodies can be produced by recombinant methods known in the art. Nucleic acids encoding the antibodies are introduced into host cells and expressed using materials and procedures described herein and known in the art. In a preferred embodiment, the antibodies are produced in mammalian host cells, such as CHO cells. Fully human antibodies may be produced by expression of recombinant DNA transfected into host cells or by expression in hybridoma cells as described above.

Techniques for creating recombinant DNA versions of the antigen-binding regions of antibody molecules which bypass the generation of monoclonal antibodies are encompassed within the practice of this invention. To do so, antibody-specific messenger RNA molecules are extracted from immune system cells taken from an immunized animal, and transcribed into complementary DNA (cDNA). The cDNA is then cloned into a bacterial expression system. One example of such a technique suitable for the practice of this invention uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind the antigen. Such target molecule specific binding partners (Fab fragments with specificity for the target molecule) are specifically encompassed within the term "antibody" as it is defined, discussed, and claimed herein.

Also within the scope of the invention are techniques developed for the production of chimeric antibodies by splicing the genes from a mouse antibody molecule of appropriate antigen-specificity together with genes from a human antibody molecule of appropriate biological activity, such as the ability to activate human complement and mediate ADCC. (Morrison et al., Proc. Natl. Acad. Sci. 81:6851 (1984); Neuberger et al., Nature, 312:604 (1984)). One example is the replacement of a Fc region with that of a different isotype. Specific binding partners such as antibodies produced by this technique are within the scope of the invention.

In a preferred embodiment of the invention, the antibodies are fully human antibodies. Thus encompassed by the invention are antibodies that bind target molecules and are encoded by nucleic acid sequences which are naturally occurring somatic variants of human germline immunoglobulin nucleic acid sequence, and fragments, synthetic variants, derivatives and fusions thereof. Such antibodies may be produced by any method known in the art. Exemplary methods include immunization with a target antigen (any target polypeptide capable of elicing an immune response, and optionally conjugated to a carrier) of transgenic animals (e.g., mice) that are capable of producing a repertoire of human antibodies in the absence of endogenous immunoglobulin production. See, for example, Jakobovits et al., Proc. Natl. Acad. Sci., 90, 2551–2555 (1993); Jakobovits et al., Nature, 362, 255–258 (1993); Bruggermann et al., Year in Immunol., 7, 33 (1993).

Alternatively, human antibodies may be generated through the in vitro screening of phage display antibody libraries. See Hoogenboom et al, J. Mol. Biol., 227 381 (1991); Marks et al., J. Mol. Biol., 222, 581 (1991), incorporated herein by reference. Various antibody-containing phage display libraries have been described and may be readily prepared by one skilled in the art. Libraries may contain a diversity of human antibody sequences, such as human Fab, Fv, and scFv fragments, that may be screened against an appropriate target. As described further below, phage display libraries may comprise peptides or proteins other than antibodies which may be screened to identify specific binding partners of the target molecule.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the monoclonal antibody with the monoclonal antibody to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference. The anti-Id antibody may also be used as an "immunogen" to induce an immune response in yet another animal, producing a so-called anti-anti-Id antibody. The anti-anti-Id may be epitopically identical to the original monoclonal antibody which induced the anti-Id. Thus, by using antibodies to the idiotypic determinants of a mAb, it is possible to identify other clones expressing antibodies of identical specificity.

Peptides and Peptide fusion molecules.

The patent application WO 00/24782, published May 4, 2000, mentioned previously herein describes in detail various peptide generation techniques. That patent application further describes various derivatives and fusion molecules.

In particular, a peptide used as a specific binding partner may be comprised within a molecule of the formula $$(X^1)_a—F^1—(X^2)_b$$

wherein:

$F^1$ is a vehicle;

$X^1$ and $X^2$ are each independently selected from
—$(L^1)_c$—$P^1$, —$(L^1)_c$—$P^1$—$(L^2)_d$—$P^2$, —$(L^1)_c$—$P^1$—$(L^2)_d$—$P^2$—$(L^3)_e$—$P^3$, and —$(L^1)_c$—$P^1$—$(L^2)_d$—$P^2$—$(L^3)_e$—$P^3$—$(L^4)_f$—$P^4$ $P^1$, $P^2$, $P^3$, and $P^4$ are each independently peptide sequences, wherein at least one is a specific binding partner;

$L^1$, $L^2$, $L^3$, and $L^4$ are each independently linkers; and a, b, c, d, e, and f are each independently 0 or 1, provided that at least one of a and b is 1.

Preferably, such a molecule comprises a structure of the formulae $$X^1—F^1$$

or $$F^1\text{-}X^2.$$

A more preferred molecule comprises a structure of the formula $$F^1\text{-}(L^1)_c\text{-}P^1.$$

or a structure of the formula $$F^1—(L^1)_c\text{-}P^1—(L^2)_d—P^2$$

wherein $P^1$ and/or $P^2$ is a specific binding partner for TACI or BCMA. Such molecules facilitate modulation of both TACI and BCMA; for example, one of $P^1$ and $P^2$ is a specific binding partner for TACI and the other is a specific binding partner for BCMA. Conversely, in a ligand inhibitor, one of $P^1$ and $P^2$ is a specific binding partner for APRIL and the other is a specific binding partner for AGP-3.

For all of these molecules, the preferred vehicle is an Fc domain.

Among Fc domains, IgG Fc, particularly IgG1, are preferred.

The Fc domains, linkers, and processes of preparation of the foregoing molecules is described in WO 00/24782, published May 4, 2000.

Soluble Receptor Fragments

Another class of specific binding partners are soluble receptor fragments. Of particular interest are the fragments identified in the figures:

a. the extracellular region of TACI (SEQ ID NO: 15).
b. the extracellular region of BCMA (SEQ ID NO: 6).
c. the consensus region of TACI (SEQ ID NO: 16).
d. the consensus region of BCMA (SEQ ID NO: 7).
e. the TACI/BCMA extracellular consensus sequence (SEQ ID NO: 13).

These molecules have the heretofore unrecognized advantage of binding both APRIL and AGP-3. Like the aforementioned peptides, these specific binding partners may also be covalently linked to a vehicle, preferably an Fc domain.

Muteins

Additional useful peptide sequences may result from conservative and/or non-conservative modifications of the amino acid sequences of the aforementioned antibodies, peptides, Fc-fusion peptides, and receptor fragments.

Conservative modifications will produce molecules having functional and chemical characteristics similar to those of the molecule from which such modifications are made. In contrast, substantial modifications in the functional and/or chemical characteristics of the molecules may be accomplished by selecting substitutions in the amino acid sequence that differ significantly in their effect on maintaining (a) the structure of the molecular backbone in the area of the substitution, for example, as a sheet or helical conformation, (b) the charge or hydrophobicity of the molecule at the target site, or (c) the size of the molecule.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, *Acta Physiol. Scand. Suppl.* 643:55–67; Sasaki et al., 1998, *Adv. Biophys.* 35:1–24, which discuss alanine scanning mutagenesis).

Desired amino acid substitutions (whether conservative or non-conservative) can be determined by those skilled in the art at the time such substitutions are desired. For example, amino acid substitutions can be used to identify important residues of the molecule sequence, or to increase or decrease the affinity of the molecules described herein. Exemplary amino acid substitutions are set forth in Table 3.

TABLE 3

| Amino Acid Substitutions | | |
|---|---|---|
| Original Residues | Exemplary Substitutions | Preferred Substitutions |
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |

TABLE 3-continued

Amino Acid Substitutions

| Original Residues | Exemplary Substitutions | Preferred Substitutions |
|---|---|---|
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

As noted in the foregoing section "Definition of Terms," naturally occurring residues may be divided into classes based on common sidechain properties that may be useful for modifications of sequence. For example, non-conservative substitutions may involve the exchange of a member of one of these classes for a member from another class. Such substituted residues may be introduced into regions of the molecule that are homologous with non-human orthologs, or into the non-homologous regions of the molecule. In addition, one may also make modifications using P or G for the purpose of influencing chain orientation.

In making such modifications, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J. Mol. Biol.,* 157: 105–131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within +1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants of the polypeptide as set forth in the foregoing sequences using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a molecule to similar molecules. With such a comparison, one can identify residues and portions of the molecules that are conserved among similar polypeptides. It will be appreciated that changes in areas of a molecule that are not conserved relative to such similar molecules would be less likely to adversely affect the biological activity and/or structure of the molecule. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the molecule structure.

Additionally, one skilled in the art can review structure-function studies identifying residues in similar molecules that are important for activity or structure. In view of such a comparison, one can predict the importance of amino acid residues in a molecule that correspond to amino acid residues that are important for activity or structure in similar molecules. One skilled in the art may opt for chemically similar amino acid substitutions for such predicted important amino acid residues of the molecules.

One skilled in the art can also analyze the three-dimensional structure and amino acid sequence in relation to that structure in similar polymolecules. In view of that information, one skilled in the art may predict the alignment of amino acid residues of a molecule with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such data could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.,* 7(4): 422–427 (1996), Chou et al., *Biochemistry,* 13(2): 222–245 (1974); Chou et al., *Biochemistry,* 113(2): 211–222 (1974); Chou et al., *Adv. Enzymol. Relat. Areas Mol. Biol.,* 47: 45–148 (1978); Chou et al., *Ann. Rev. Biochem.,* 47: 251–276 and Chou et al., *Biophys. J.* 26: 367–384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., *Nucl. Acid. Res.,* 27(1): 244–247 (1999). It has been suggested (Brenner et al., *Curr. Op. Struct. Biol.,* 7(3): 369–376 (1997)) that there are a limited number of folds in a given polypeptide or protein and that once a critical number of structures have been resolved, structural prediction will gain dramatically in accuracy.

Additional methods of predicting secondary structure include "threading" (Jones, D., *Curr. Opin. Struct. Biol.,* 7(3): 377–87 (1997); Sippl et al., *Structure,* 4(1): 15–9 (1996)), "profile analysis" (Bowie et al., *Science,* 253: 164–170 (1991); Gribskov et al., *Meth. Enzym.,* 183: 146–159 (1990); Gribskov et al., *Proc. Nat. Acad. Sci.,* 84(13): 4355–8 (1987)), and "evolutionary linkage" (See Home, supra, and Brenner, supra).

Production of Specific Binding Partners

When the specific binding partner to be prepared is a proteinaceous specific binding partner, such as an antibody or an antigen binding domain or an Fc-peptide fusion molecule, various biological or chemical methods for producing said partner are available.

Biological methods are preferable for producing sufficient quantities of a specific binding partner for therapeutic use. Standard recombinant DNA techniques are particularly useful for the production of antibodies and antigen binding domains of the invention. Exemplary expression vectors, host cells and methods for recovery of the expressed product are described below.

A nucleic acid molecule encoding an antibody or antigen binding domain is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding an antibody may be amplified/expressed in prokaryotic, yeast, insect (baculovirus systems) and/or eukaryotic host cells. Selection of the host cell will depend in part on whether an antibody is to be post-transitionally modified (e.g., glycosylated and/or phosphorylated). If so, yeast, insect, or mammalian host cells are preferable. For a review of expression vectors, see *Meth. Enz.* v. 185, (D. V. Goeddel, ed.), Academic Press Inc., San Diego, Calif. (1990).

Typically, expression vectors used in any host cells will contain one or more of the following components: a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element. Each of these sequences is discussed in more detail below.

The vector components may be homologous (i.e., from the same species and/or strain as the host cell), heterologous (i.e., from a species other than the host cell species or strain), hybrid (i.e., a combination of different sequences from more than one source), synthetic, or native sequences which normally function to regulate immunoglobulin expression. As such, a source of vector components may be any prokaryotic or eukaryotic organism, any vertebrate or invertebrate organism, or any plant, provided that the components are functional in, and can be activated by, the host cell machinery.

An origin of replication is selected based upon the type of host cell being used for expression. For example, the origin of replication from the plasmid pBR322 (Product No. 303-3s, New England Biolabs, Beverly, Mass.) is suitable for most Gram-negative bacteria while various origins from SV40, polyoma, adenovirus, vesicular stomatitis virus (VSV) or papillomaviruses (such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding regions and serves to terminate transcription. Usually, a transcription termination sequence in prokaryotic cells is a G-C rich fragment followed by a poly T sequence. While the sequence is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the marker present in the vector. Selection pressure is imposed by culturing the transformed cells under conditions in which the concentration of selection partner in the medium is successively changed, thereby leading to amplification of both the selection gene and the DNA that encodes an antibody. As a result, increased quantities of an antibody are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. The Shine-Dalgarno sequence is varied but is typically a polypurine Le., having a high A-G content). Many Shine-Dalgarno sequences have been identified, each of which can be readily synthesized using methods set forth above and used in a prokaryotic vector.

A leader, or signal, sequence is used to direct secretion of a polypeptide. A signal sequence may be positioned within or directly at the 5' end of a polypeptide coding region. Many signal sequences have been identified and may be selected based upon the host cell used for expression. In the present invention, a signal sequence may be homologous (naturally occurring) or heterologous to a nucleic acid sequence encoding an antibody or antigen binding domain. A heterologous signal sequence selected should be one that is recognized and processed, i.e., cleaved, by a signal peptidase, by the host cell. For prokaryotic host cells that do not recognize and process a native immunoglobulin signal sequence, the signal sequence is substituted by a prokaryotic signal sequence selected, for example, from the group of the alkaline phosphatase, penicillinase, or heat-stable enterotoxin II leaders. For yeast secretion, a native immunoglobulin signal sequence may be substituted by the yeast invertase, alpha factor, or acid phosphatase leaders. In mammalian cell expression the native signal sequence is satisfactory, although other mammalian signal sequences may be suitable.

In most cases, secretion of an antibody or antigen binding domain from a host cell will result in the removal of the signal peptide from the antibody. Thus the mature antibody will lack any leader or signal sequence.

In some cases, such as where glycosylation is desired in a eukaryotic host cell expression system, one may manipulate the various presequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid found in the peptidase cleavage site, attached to the N-terminus. Alternatively, use of some enzyme cleavage sites may result in a slightly truncated form of the desired polypeptide, if the enzyme cuts at such area within the mature polypeptide.

The expression vectors of the present invention will typically contain a promoter that is recognized by the host organism and operably linked to a nucleic acid molecule encoding an antibody or antigen binding domain. Either a native or heterologous promoter may be used depending the host cell used for expression and the yield of protein desired.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence(s), using linkers or adapters as needed to supply any required restriction sites.

Suitable promoters for use with yeast hosts are also well known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be used for expressing the specific binding partners of the invention include, but are not limited to: the SV40 early promoter region (Benoist and Chambon (1981), *Nature*, 290:304–310); the CMV promoter; the promoter contained in the 3' long terminal repeat of Rous sarcoma virus (Yamamoto et al. (1980), *Cell*, 22: 787–97); the herpes thymidine kinase promoter (Wagner et al. (1981), *Proc. Natl. Acad. Sci. U.S.A.*, 78: 1444–5); the regulatory sequences of the metallothionine gene (Brinster et al. (1982), *Nature*, 296: 39–42): prokaryotic expression vectors such as the beta -lactamase promoter (Villa-Kamaroff et al. (1978), *Proc. Natl. Acad. Sci. U.S.A.*, 75: 3727–31); or the tac promoter (DeBoer, et al. (1983), *Proc. Natl. Acad. Sci. U.S.A.*, 80: 21–25). Also of interest are the following animal transcriptional control regions, which exhibit tissue specificity and have been utilized in transgenic animals: the elastase I gene control region which is active in pancreatic acinar cells (Swift et al. (1984), *Cell*, 38: 639–46; Ornitz et al. (1986), *Cold Spring Harbor Symp. Quant. Biol.* 50: 399–409; MacDonald (1987), *Hepatology*, 7: :425–515); the insulin gene control region which is active in pancreatic beta cells (Hanahan (1985), *Nature*, 315: 115–122); the immunoglobulin gene control region which is active in lymphoid cells (Grosschedl et al. (1984), *Cell*, 38: 647–58; Adames et al. (1985), *Nature*, 318: 533–8; Alexander et al. (1987), *Mol. Cell. Biol.*, 7: 1436–44); the mouse mammary tumor virus control region which is active in testicular, breast, lymphoid and mast cells (Leder et al. (1986), *Cell*, 45: 485–95), albumin gene control region which is active in liver (Pinkert et al. (1987), *Genes and Devel.*, 1: 268–76); the alphafetoprotein gene control region which is active in liver (Krumlauf et al. (1987), *Mol. Cell. Biol.*, 5: 1639–48; Hammer et al. (1987), *Science*, 235: 53–58); the alpha 1-antitrypsin gene control region which is active in the liver (Kelsey et al. (1987), *Genes and Devel.*, 1: 161–171); the beta-globin gene control region which is active in myeloid cells (Mogram et al. (1985), *Nature*, 315: 338–340; Kollias et al. (1986), *Cell*, 46: 89–94); the myelin basic protein gene control region which is active in oligodendrocyte cells in the brain (Readhead et al. (1987), *Cell*, 48: 703–712); the myosin light chain-2 gene control region which is active in skeletal muscle (Sani (1985), *Nature*, 314: 283–286); and the gonadotropic releasing hormone gene control region which is active in the hypothalamus (Mason et al. (1986), *Science*, 234: 1372–8).

An enhancer sequence may be inserted into the vector to increase transcription in eucaryotic host cells. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to the polypeptide coding region, it is typically located at a site 5' from the promoter.

Preferred vectors for practicing this invention are those which are compatible with bacterial, insect, and mammalian host cells. Such vectors include, inter alia, pCRII, pCR3, and pcDNA3.1 (Invitrogen Company, San Diego, Calif.), pBSII (Stratagene Company, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII; Invitrogen), pDSR-alpha (PCT Publication No. WO90/14363) and pFastBacDual (Gibco/BRL, Grand Island, N.Y.).

Additional possible vectors include, but are not limited to, cosmids, plasmids or modified viruses, but the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.). The recombinant molecules can be introduced into host cells via transformation, transfection, infection, electroporation, or other known techniques.

Host cells of the invention may be prokaryotic host cells (such as *E. coli*) or eukaryotic host cells (such as a yeast cell, an insect cell, or a vertebrate cell). Prokaryotic host cells such as *E. coli* produce unglycosylated protein; for example, unglyclosylated shBCMA and unglycosylated shTACI, which may possess advantages over the glycosylated eukaryotic molecules. The host cell, when cultured under appropriate conditions, expresses an antibody or antigen binding domain of the invention which can subsequently be collected from the culture medium (if the host cell secretes it into the medium) or directly from the host cell producing it (if it is not secreted). Selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), Manassas, Va. Examples include mammalian cells, such as Chinese hamster ovary cells (CHO) (ATCC No. CCL61) CHO DHFR-cells (Urlaub et al. (1980), *Proc. Natl. Acad. Sci. USA* 7, 4216–20), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the American Type Culture Collection, Manassas, Va.). Each of these cell lines is known by and available to those skilled in the art of protein expression.

Similarly useful as host cells suitable for the present invention are bacterial cells. For example, the various strains of *E. coli* (e.g., HB101, (ATCC No. 33694) DH5α, DH10, and MC1061 (ATCC No. 53338)) are well-known as host cells in the field of biotechnology. Various strains of Pseudomonas spp., *B. subtilis*, other Bacillus spp., Streptomyces spp., and the like may also be employed in this method.

Many strains of yeast cells known to those skilled in the art are also available as host cells for expression of the polypeptides of the present invention. Preferred yeast cells include, for example, *Saccharomyces cerivisae*.

Additionally, where desired, insect cell systems may be utilized in the methods of the present invention. Such systems are described for example in Kitts et al. (1993), *Biotechniques*, 14: 810–7, Lucklow (1993), *Curr. Opin. Biotechnol.*, 4: 564–72, and Lucklow et al. (1993), *J. Virol.*, 67: 4566–79. Preferred insect cells are Sf-9 and Hi5 (Invitrogen, Carlsbad, Calif.).

Transformation or transfection of a nucleic acid molecule encoding a specific binding partner into a selected host cell may be accomplished by well known methods including methods such as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

One may also use transgenic animals to express glycosylated specific binding partners, such as antibodies and antigen binding domain. For example, one may use a transgenic milk-producing animal (a cow or goat, for example) and obtain glycosylated binding partners in the animal milk. Alternatively, one may use plants to produce glycosylated specific binding partners.

Host cells comprising (as by transformation or transfection) an expression vector encoding a specific binding partner of the target molecule may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalburnin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline and neomycin.

The amount of an antibody or antigen binding domain produced by a host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays.

Purification of a specific binding partner that has been secreted into the cell media can be accomplished using a variety of techniques including affinity, immunoaffinity or ion exchange chromatography, molecular sieve chromatography, preparative gel electrophoresis or isoelectric focusing, chromatofocusing, and high pressure liquid chromatography. For example, antibodies comprising a Fc region may be conveniently purified by affinity chromatography with Protein A, which selectively binds the Fc region. Modified forms of an antibody or antigen binding domain may be prepared with affinity tags, such as hexahistidine or other small peptide such as FLAG (Eastman Kodak Co., New Haven, Conn.) or myc (Invitrogen) at either its carboxyl or amino terminus and purified by a one-step affinity column. For example, polyhistidine binds with great affinity and specificity to nickel, thus an affinity column of nickel (such as the Qiagen® nickel columns) can be used for purification of polyhistidine-tagged specific binding partners. See for example, Ausubel et al., eds. (1993), *Current*

Protocols in Molecular Biology, Section 10.11.8, John Wiley & Sons, New York. In some instances, more than one purification step may be required.

Specific binding partners of the invention which are expressed in procaryotic host cells may be present in soluble form either in the periplasmic space or in the cytoplasm or in an insoluble form as part of intracellular inclusion bodies. Specific binding partners can be extracted from the host cell using any standard technique known to the skilled artisan. For example, the host cells can be lysed to release the contents of the periplasm/cytoplasm by French press, homogenization, and/or sonication followed by centrifugation.

Soluble forms of an antibody or antigen binding domain present either in the cytoplasm or released from the periplasmic space may be further purified using methods known in the art, for example Fab fragments are released from the bacterial periplasmic space by osmotic shock techniques.

If an antibody or antigen binding domain has formed inclusion bodies, they can often bind to the inner and/or outer cellular membranes and thus will be found primarily in the pellet material after centrifugation.

The pellet material can then be treated at pH extremes or with chaotropic partner such as a detergent, guanidine, guanidine derivatives, urea, or urea derivatives in the presence of a reducing partner such as dithiothreitol at alkaline pH or tris carboxyethyl phosphine at acid pH to release, break apart, and solubilize the inclusion bodies. The soluble specific binding partner can then be analyzed using gel electrophoresis, immunoprecipitation or the like. If it is desired to isolate a solublized antibody or antigen binding domain, isolation may be accomplished using standard methods such as those set forth below and in Marston et al. (1990), *Meth. Enz.*, 182: 264–75.

In some cases, an antibody or antigen binding domain may not be biologically active upon isolation. Various methods for "refolding" or converting the polypeptide to its tertiary structure and generating disulfide linkages, can be used to restore biological activity. Such methods include exposing the solubilized polypeptide to a pH usually above 7 and in the presence of a particular concentration of a chaotrope.

The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing partner or the reducing partner plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, and 2-mercaptoethanol (bME)/dithio-b(ME). In many instances, a cosolvent may be used or may be needed to increase the efficiency of the refolding and the more common repartners used for this purpose include glycerol, polyethylene glycol of various molecular weights, arginine and the like.

Specific binding partners of the invention may also be prepared by chemical synthesis methods (such as solid phase peptide synthesis) using techniques known in the art such as those set forth by Merrifield et al. (1963),*J. Am. Chem. Soc.,* 85: 2149; Houghten et al. (1985), *Proc Natl Acad. Sci. USA,* 82: 5132; and Stewart and Young (1984), *Solid Phase Peptide Synthesis,* Pierce Chemical Co., Rockford, Ill. Such polypeptides may be synthesized with or without a methionine on the amino terminus. Chemically synthesized antibodies and antigen binding domains may be oxidized using methods set forth in these references to form disulfide bridges. Antibodies so prepared will retain at least one biological activity associated with a native or recombinantly produced antibody or antigen binding domain.

The invention will now be further described by specific experimental examples. These examples are meant to be illustrative rather than limiting.

Working Examples

Materials and Methods

Isolation of BCMA and TACI cDNA

```
Mouse and human BCMA cDNA were isolated by PCR
using the mouse BCMA sense primer
5'-CACAATACCTGTGGCCCTCTTAAGAG-3' (SEQ ID NO:25),
and antisense primer 5'-TGGTAAACGGTCATCCTAACGACATC-3' (SEQ ID NO:26),
the human BCMA sense primer 5'-TTACTTGTCCTTCCAGGCTGTTCT-3' (SEQ ID NO:27),
and antisense primer 5'-CATAGAAACCAAGGAAGTTTCTACC-3' (SEQ ID NO:28).
For isolation of human TACI cDNA, the sense primer 5'-AGCATCCTGAGTAATGAGTGGCCTGG-3' (SEQ ID NO:29)
and antisense primer

5'-GTGATGACGACCTACAGCTGCACTGGG-3' (SEQ ID NO:30)
``` were used. Poly (A)+ RNA from the mouse B lymphoma cell line -A20 and human lymph Node were reverse—transcribed and cDNA were synthesized by using the Smart RACE cDNA amplification Kit (Clontech, palo Alto, Califormia). The full-length cDNA of mouse and human BCMA genes as well as human TACI gene were cloned into pcDNA3 vector for mammalian cell expression (Invitrogen, Carlsbad, Calif.).

Recombinant Proteins

Soluble murine APRIL-Flag protein was generated by fusing Flag sequence in frame to the N-terminus of APRIL amino acid 101–239. Soluble mAPRIL-Flag protein was expressed in *E. coli* and the refolded protein was affinity-purified by anti-Flag M2 antibody column. Fc-tagged AGP3 protein was generated by fusing OPG signal peptide followed by human IgG-yl Fc in frame to the N-terminus of AGP3 amino acid 128–285. The protein was expressed in baculovirus and purified with protein A sepharose column. Fc-tagged human APRIL was encoded by a similar construct (see FIG. 21) and expressed in CHO cells and purified with protein A sepharose coloumn.

Soluble TACI protein (amino acids 1–165) and BCMA protein (amino acid 4–55) followed by human IgGy1 Fc in frame was expressed in *E. coli*. The inclusion bodies formed were solubilized. The refolded protein was purified by cation exchange chromatography.

Purification of Human BCMA-Fc

Purification of human BCMA-Fc produced in recombinant *E. coli* was initiated by solubilizing 53.3 g of a washed inclusion body preparation in a solution having a final composition of 6M guanidinium chloride, 50 mM Tris(HCl), 8.0 mM dithiothreitol. The final volume of solution was approximately 200 mL. The solution was adjusted to pH 9.0 at 23 degrees Centigrade and allowed to stir at room temperature for one hour.

The solubilized polypeptide solution was then added to 3.8 L of cold 4 M urea, 160 mM L-arginine, 20% (volume) glycerol, 4 mM cysteine, 1 mM cystamine, 50 mM Tris. The pH was adjusted to 8.9 at 12 degrees Centigrade and the mixture was allowed to stir at 4–8 for approximately 60 hours.

The refolding mixture was then clarified by filtration through a 0.9 square foot Cuno 10SP cartridge. The filtrate was then concentrated approximately five fold and diafiltered with five retentate volumes of 10 mM sodium phosphate/40 mM sodium chloride, pH 9 using a 1.0 square foot Pall Filtron regenerated cellulose TFF cassette having a nominal molecular weight cutoff of 50 kDa. Processing was performed at 4–8 degrees Centigrade.

The retentate was removed from the unit, warmed to 20 degrees Centigrade, and adjusted to pH 5.0 using 1 M acetic acid. The precipitated solids were then removed by centrifugation in a Beckman J6-B centrifuge operating at 20 degrees Centigrade at approximately 2500× g for approximately 15 minutes. The supernatant was aliquotted and stored frozen at −30 degrees Centigrade.

Aliquots of supernatant were thawed and processed over a 5.0 cm diameter×27.5 cm height column of SP-Sepharose Fast Flow. All phases of the chromatography were performed at 8 degrees Centigrade. The column was equilibrated using 25 mM sodium phosphate, pH 6.5. The product was conditioned for loading by adjusting the pH to 6.5. Following the load, the column was washed with equilibration buffer, and the product was then eluted with a linear gradient from 17 mM to 60 mM sodium chloride in a background of 25 mM sodium phosphate pH 6.5, over 20 column volumes. Fractions were selected for further processing based on their appearance on a Coomassie blue-stained SDS polyacrylamide gel.

The pooled SP-Sepharose Fast Flow fractions were further processed over a 5.0 cm diameter×27.5 cm height column of Butyl Toyopearl 650M, operated at 21 degrees Centigrade. The product was conditioned prior to loading by adding solid potassium phosphate to give a final concentration of approximately 0.6 M. The column was equilibrated using 0.6M potassium phosphate, pH 7.0. After loading, the column was washed with 0.5 bed volumes of equilibration buffer, and the product was then eluted using a linear gradient from 0.5 M to 0.3 M potassium phosphate over 15 column volumes. Fractions from the predominant UV elution peak were pooled for further processing.

The pooled fractions from the Butyl Toyopearl chromatography were concentrated twenty fold and diafiltered against six retentate volumes of phosphate buffered saline using a Millipore XL TFF cassette, operated at 4–8 degrees Centigrade. The final retentate pool was aliquotted and stored at −30 degrees Centigrade.

In Vivo Study

B6 mice (6–8 weeks old)were purchased from Charles River Laboratories and murine APRIL-Flag and other TNF proteins were injected i.p. of 1 mg/kg/day for 5 days. On day 7, cells from mouse spleens and mesenteric lymph nodes were collected and B and T cell activation and differentiation was analyzed by FACS using specific monoclonal antibodies staining.

Cell Lines and Proliferation Assays 293 human kidney epithelial cells, Raji Burkitt lymphoma, human T lymphoblastoma Jurkat cells and A20, mouse B lymphoma cell line were purchased from the American Type Culture Collection (Rockville, Md.).Raji, Jurkat and A20 cells were maintained in a complete medium of RPMI-1640 (life Technologies) supplemented with 10%fetal bovine serum (HyClone, Logan, Utah)and 25 mM HEPES. 293 cells were cultured in Dulbecco's modified Eagle's medium (Life Technologies) with 10% fetal bovine serum.The proliferation of cells were determined by incubating $5\times10^4$ cells/well in 100 μL medium with the indicated concentration of APRIL-flag protein using the celltiter 96 AQ proliferation assay (Promega Corp.,Madison, Wis.) following the manufacturer's instructions. Alternatively, cells were pulsed for 18 h with $^3$H thymidine (0.5 μCi/well), after harvesting cells, $^3$H thymidine incorporation was monitored by liquid scintillation counting.

Transfection and Flow Cytometric Analysis

For 293 cell expressing BCMA and TACI receptor, $2\times10^6$ 293 cells were plated into 6 well plate, cells were transfected with lipofectAMINE 2000 following the manufacturer's procedure (Life Technologies), 48 h after transfection, cells were collected and incubated at 4 C with 1 μg/ml APRIL-Flage ligand or Blys (AGP3)-Fc ligand for 60 min, after washing 3 times with PBS (containing 2% FBS), cells were stained with FITC-conjugated secondary antibody for 30 min, then washed 3 times with PBS and fluorescence was analyzed by FACS scanner (Becton Dickinson, Mountain View, Calif.).

Determination of the Binding Affinities of APRIL and TALL-1 for BCMA and TACI

Biomolecular interaction analysis (BIA) was performed using a BIACORE 2000 (Biacore AB, Uppsala, Sweden). The receptors, BCMA-Fc and TACI-Fc (2 μg/ml in 10 mM sodium acetate, pH 4.5), were immobilized on Sensor Chip CM5 using the BIACORE standard amine coupling procedure. An immobilization level of approximately 120 RU's was achieved. The analytes, Flag-APRIL and Fc-AGP-3 were diluted between 100 nM-0.01 nM in running buffer (10 mM HEPES, 0.5 M NaCl, 3 mM EDTA, 0.005% Tween 20, 2 mg/ml CM dextran, pH 6.8). The analytes were injected over an immobilized receptor surface for 2 minutes at 50 μl/min and allowed to dissociate for 10 minutes. Bound protein was removed by a 1 minute injection of 50 mM HCl. Binding affinities were determined using a 1:1 Langmuir model (BIA Evaluation software Version 3.1.2, BIACORE).

T Cell Co-Stimulation Assay

T cells from the spleens of C57 Bl/6 mice were purified by negative selection through a murine T cell enrichment column (R&D Systems). T cells ($1\times10^5$ per well) were cultured in the absence or presence of various APRIL-Flag protein for 48 hr. Alternatively, 96 well plates were pre-coated with subliminal quantities of anti-CD3 antibody, T cells were treated with APRIL-Flag protein for 72 hr, pulsed during the last 18 hr with 1 μCi of $^3$H thymidine and harvested to count the incorporation radioactivity.

B Cell Proliferation and Ig Secretion

Mouse B cell were negatively selected from spleens by mouse B cell recovery column (Cedarlane, Hornby, Ontario Canada). $1\times10^6$/ml were seeded in 96-well flat bottom tissue culture plates in medium (RPMI-1640, 5% FBS, $5\times10^{-5}$M 2 ME, affinity-purified goat anti-mouse IgM 2.5 μg/ml Pharmingen, San Diego). B cells were then treated with APRIL-Flag protein plus different concentration of soluble BCMA-Fc protein for 72 hr and culture received 1 μCi of $^3$H thymidine during the last 18 hr. proliferation of B cell was quantitated by measuring the incorporation of radioactivity.

For analysis of Ig secretion from B cells, purified B cells $5\times10^5$/ml were cultured in 96well flat bottom tissue culture plates in the presence of APRIL-Flag for six days. The culture supernatant were harvested and IgG, IgM and IgA levels were determined by an isotype specific sandwich ELISA technique. Ig concentration in test samples were determined by comparing triplicate test values with isotype control standard.

Induction and Detection of Anti-keyhole Limpet Hemocyanin (KLH) and Anti-Pneumovax Antibodies.

Mice (Balb/c females of 9–11 wk and 19–21 g, Charles River Laboratories, Wilmington, Mass.) were immunized on day 0 with 100 μg of KLH (Pierce, Rockford, Ill.) in CFA s.c. or with 115 μg of Pneumovax (Merck, West Point, Pa.) i.p. Starting on day 0, mice received 7 daily i.p. injections of 5 mg/Kg of either TACI-Fc or BCMA-Fc fusion proteins or non-fused Fc and were then bled on day 7. Anti-KLH and anti-Pneumovax IgG and IgM were measured in serum by ELISA. Briefly, for the measurement of anti-KLH antibodies, plates were coated with KLH in PBS, blocked, and added with dilutions of standard and test samples. Captured anti-KLH IgG or IgM were revealed using anti-IgG or anti-IgM biotinylated antibodies and neutravidin-conjugated HRP. For the measurement of anti-Pneumovax IgM, plates were coated with Pneumovax using poly-L-lysine, blocked, and added with dilutions of standard and test samples. Captured anti-Pneumovax IgM were revealed using an anti-IgM biotinylated antibody and neutravidin-conjugated HRP. Results were compared with the Student t test.

In a second experiment, normal mice (n=7) were treated with human BCMA-Fc, truncated TACI-Fc and nonfused Fc as a control in daily doses of 0.5 mg/kg to 15 mg/kg for 7 days. At preimmunization anti-KLH and anti-Pneumovax were undetectable. Antibodies were measured on day 7 and Day 14. hBCMA-Fc effect on mouse peripheral blood B cell in vivo. Normal mice (15 mg/kg ip on day 0, 3, and 6; n=7) were treated with human BCMA-Fc and nonfused Fc as a control in day 0,3, and 6 (15 mg/kg). Peripheral blood and spleen B cell level were measured on day 7. Flag-mAPRIL, hAGP3, hBCMA-Fc and hTACI-Fc effects on immunoglobulin production in vitro. Purified murine spleen B cells were cultured with LPS (100 ng/ml),AGP3 (10 ng/ml),Flag-APRIL (10 ng/ml) or plus BCMA-Fc (100 ng/ml) and TACI-Fc (100 ng/ml) for 12 days. Culture supernatants were collected on day 7 and day 12 for detecting IgA and IgG levels. mBCMA-Fc and trun hTACI-Fc effect on immunoglobulin levels in vitro.

Normal mice were treated with mBCMA-Fc; trun hTACI-Fc; or Fc-control (5 mglkg ip day 0, 3, and 6; n=7). Immunoglobulin levels in serum were measured on day 7.

Generation and Analysis of Anti-mAPRIL Specific Monoclonal Antibody.

Flag-mAPRIL was used as antigen for generation of rat anti-nAPRIL specific monoclonal antibodies following standard procedures. Fourty clones that recognized Flag-APRIL in an ELISA were identified. The clones effect on Flag-mAPRIL mediated mouse B cell proliferation was determined. Purified murine spleen B cells were cultured in presence 10 ng/ml mFlag-APRIL plus 2 ug/ml of anti-IgM. anti-Flag-APRIL monoclonal antibody and rat IgG control were added into culture in same time. Data show incorporation of $^3$H thymidine as cpm,and represent mean of triplicate wells. Anti-mAPRIL specific monoclonal antibody #c19 5 mg/kg ip on day 0, 3, and 6 was used for determining the effect of blocking endogenous APRIL on anti-Pheumovacs IgM In Vivo.

NZBxNZWF1 Lupus Model.

Five months old NZBxNZWF1 mice were treated 3 times/week (mon, wed, fri) for a period of 5 months with the indicated amount of protein. 100 ug dose translates to 4 mg/Kg. Mice were bled at day of treatment to later be analyzed for DNA-specific antibodies, histone proteins, etc. Also at day 0, urine were taken and analyzed for proteins levels. Animals are excluded that already have high levels of protein in the urine, a sign of lupus. Treatment was injected i.p. Urine and blood are taken every 30 days and analyzed until day 150.

APRIL Binding and Stimulation of Tumor Cells.

APRIL binding to human tumor cell lines were determined by incubating cell with lug/ml Fc-APRIL or Flag-APRIL following FITC labeled secondary antibody staining and FACS analysis. APRIL and BCMA-Fc or TACI-Fc effect on U266-B1 cell growth: U266 cells were cultured in presence lOng/ml human Fc-APRIL or plus 50 ng/ml soluble BCMA-Fc, Truncated TACI-Fc for 48 hr. Incorporation of $^3$H thymidine is indicated as cpm. Data shown represent mean of triplicate wells. A20 mouse B cell lymphoma were cultured in presence 50 ng/ml mouse Flag-APRIL,human Flag-AGP3 or plus 100 ng/ml soluble BCMA-Fc for 48 hr. Incorporation of $^3$H thymidine is indicated as cpm. Data shown represent mean of triplicate wells.

A20 B Lymphoma Tumor Cell Growth in Balb/c Mice.

A20 (0.2 million) cells were implanted, id, on day 0. Treatments with PBS, CHO-Fc, mBCMA-Fc, hBCMA-Fc, mTACI-Fc, hTACI-Fc were given (10 mg/kg, ip) on days 0, 7, 10, 13, 16, 19, 22. Tumor measurements were made twice per week. Mice were sacrificed on days 27–31, tumors were snap frozen for RNA isolation, blood was collected and serum samples were frozen.

Human Colon Carcinoma Cell Line HT29 Tumor Growth.

$2\times10^6$ HT29 cells plus 50% matrigel injected subcutaneously into athymic nude mice. Rx: human or mouse BCMA-Fc at 2,5, and 15 mg/kg Q2D, starting at day 0 (n=10/group). Control 1: CHO-Fc at 15 mg/kg Q2D. Control 2: 0.2 ml of PBS Q2D IP. Tumor volume: 3/week, from day 7. Tumor weight at end of study. Body weight 2/week.

Results

G70/APRIL In Vitro Function

Figure 4B:
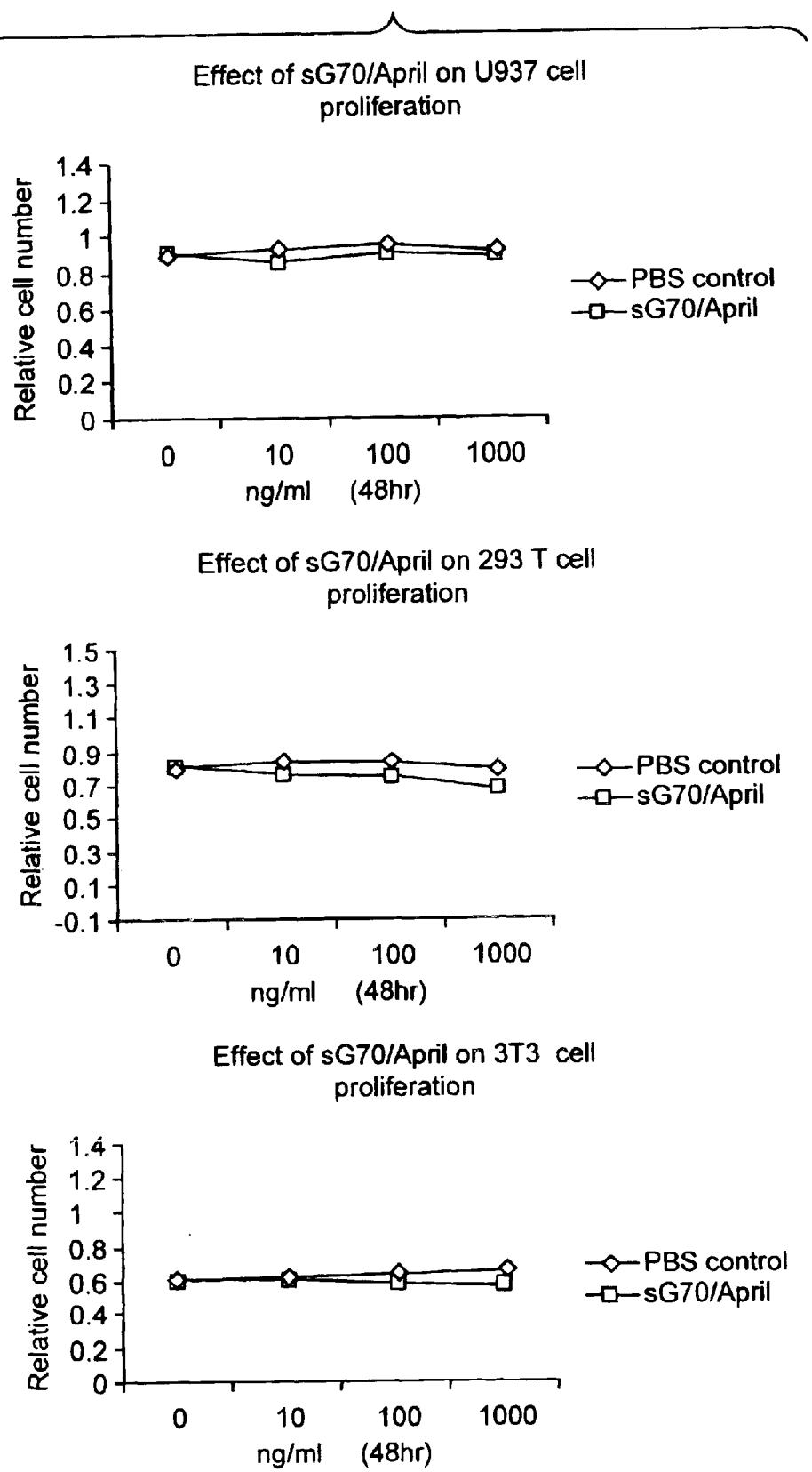
In FIG. 4B, U937 cell (monocyte-like leukemia cells), NIH/3T3 (mouse embryo cell line) and 293 (transformed human primary embryonal kidney cell line) did not respond to sG70/APRIL stimulation.
Figures 1, 5B:
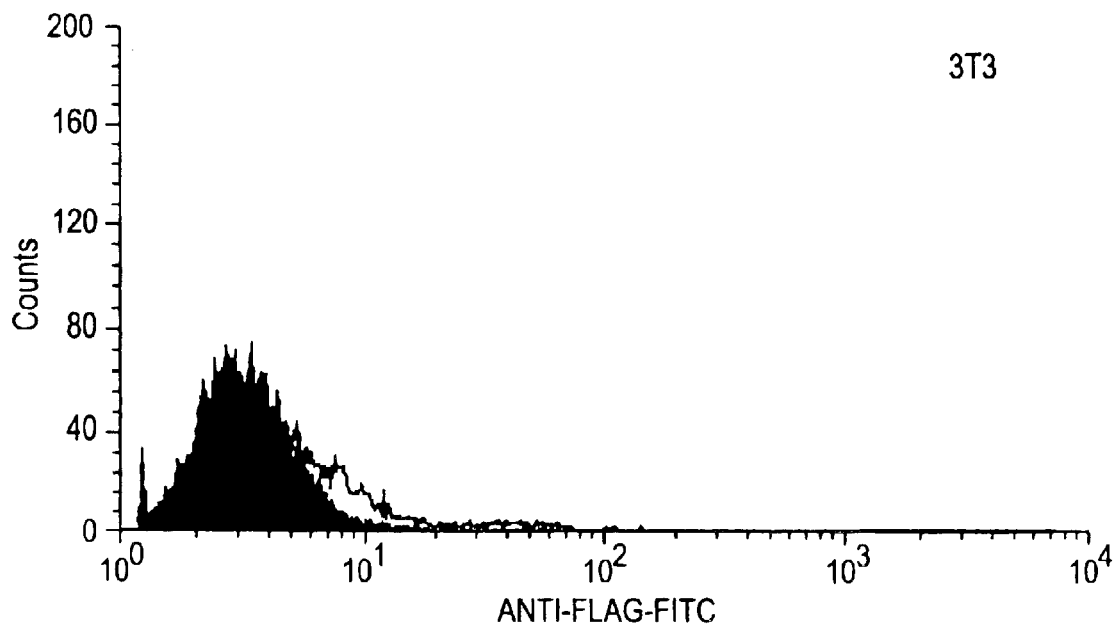
Figures 2, 5B:
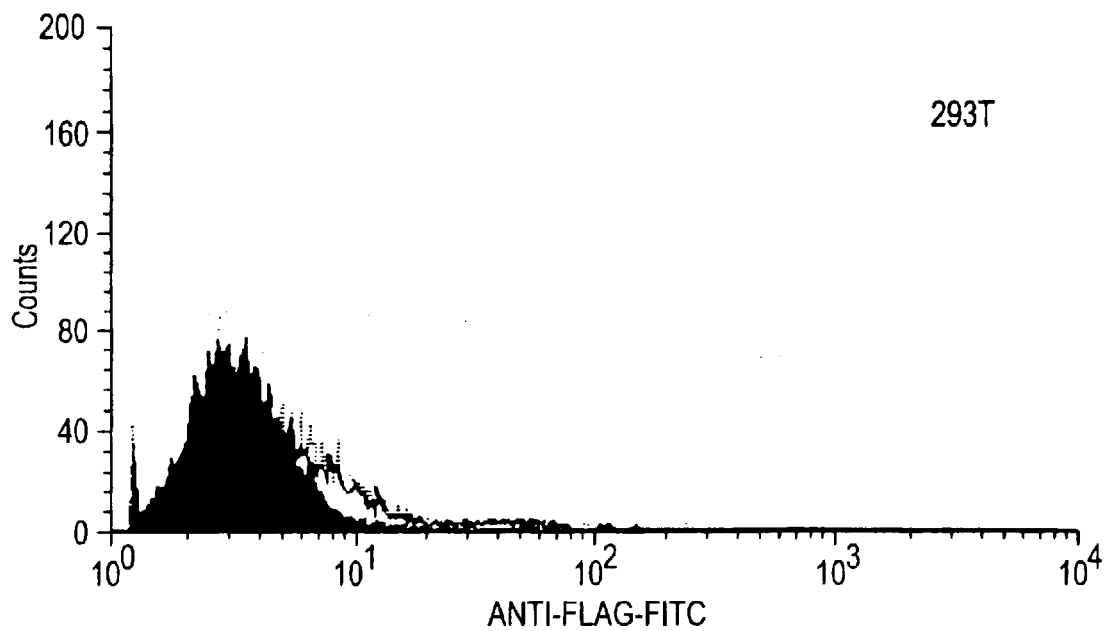
Figures 3, 5B:
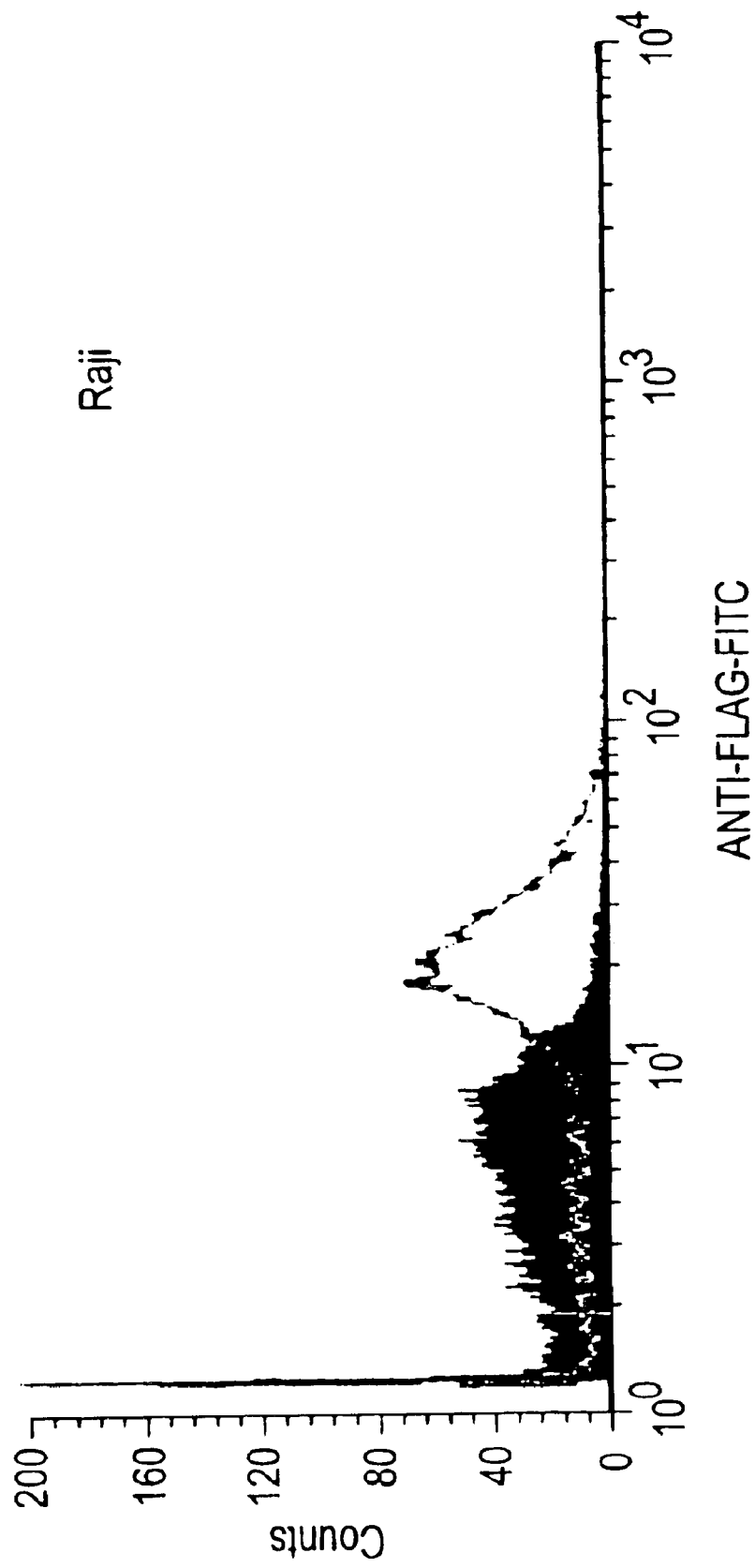
Figure 8:
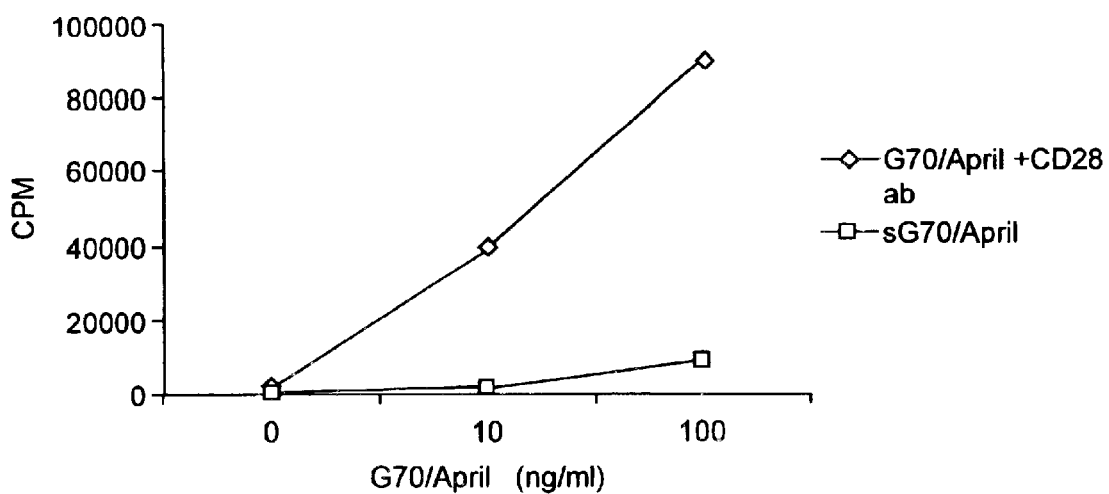
FIG. 8 shows the effect of G70/APRIL on murine T cell proliferation costimulated though anti-CD28 antibody. T-cells from the spleens of C57B1 mice were purified by selection through a murine T-cell enrichment column. $1 \times 10^5$ T-cells per well were treated with G70/APRIL in the absence or presence of subliminal concentration of anti-CD28 antibody (0.9 $\mu$g/ml) for 48 hours, pulsed during the last 18 hours with 0.5 $\mu$Ci $^3$H thymidine and harvested to count the incorporated radioactivity.
Figure 9:
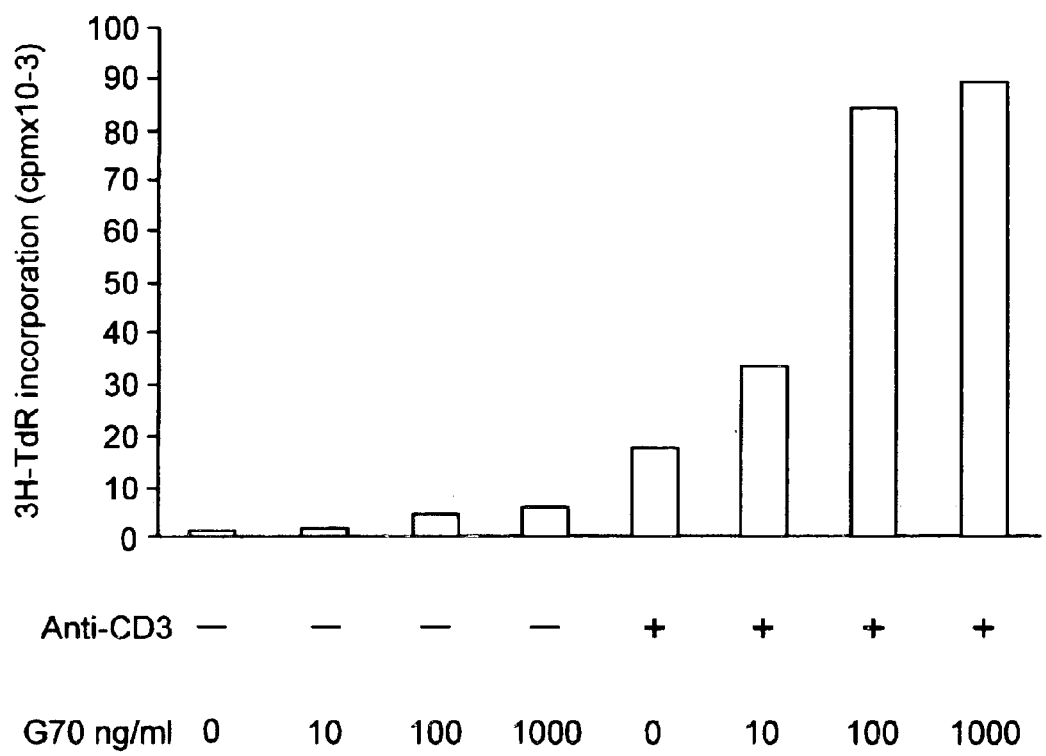
FIG. 9 shows the effect of G70/APRIL on murine T cell proliferation costimulated though anti-CD3 antibody. T-cells from the spleens of C57B1 mice were purified by selection through a murine T-cell enrichment column. $1 \times 10^5$ T-cells per well were treated with G70/APRIL in the absence or presence of subliminal concentration of anti-CD3 antibody (0.9 $\mu$g/ml) for 48 hours, pulsed during the last 18 hours with 0.5 $\mu$Ci $^3$H thymidine and harvested to count the incorporated radioactivity. Table 1 shows FACS analysis of spleen (Table 1A), and mesenteric lymph nodes (Table 1B) after in vivo systemic administration of TNF family members. Several members of TNF family have been tested in vivo, each group have 5 mice (BDF-1, 8 weeks of age, Dose: 1 mg/kg/day 0.2 ml for 5 days). Spleen, thymus and mesenteric lymph nodes from three mice of each group have been isolated for FACS analysis using a panel of T cell and B cell surface mark antibodies. Results of FACS analysis have been summarized as following tables.

Human and mouse G70, also called APRIL, was isolated and characterized (FIGS. 1, 2, and 3). FLAG-tagged soluble mouse G70 (smG70) was produced in *E. coli* purified and refolded (FIG. 2). Soluble G70 (smG70) specifically stimulates B and T cell lymphoma cell proliferation in a dose-dependent manner (FIG. 4). Furthermore, soluble G70:

1) specifically binds to cell-surface receptors expressed on human B and T lymphoma cells (FIG. 5);
2) specifically stimulates proliferation of purified human peripheral blood B and T cells (FIG. 6);
3) stimulates proliferation of purified murine spleen B and T cells in a dose-dependent manner (FIG. 7);
4) acts synergistically with anti-CD28 antibody to stimulate proliferation of purified murine T cells (FIG. 8);
5) has a strong costimulatory activity on purified murine T cells (FIG. 9) in the presence of sub-optimal concentration of the T cell receptor activator: anti-CD3 antibody.

G70/APRIL In Vivo Function

A series of experiments were performed to elucidate soluble G70/APRIL's biological activity in normal mice in vivo. Each group consisted of 5 mice (BDF-1, 8 weeks of age, dosed at 1 mg/kg/day, 0.2 ml for 5 days). Spleen, thymus and mesenteric lymph nodes from three mice of each group was used for FACS analysis using a panel of T cell and B cell surface marker antibodies and all the mice were analyzed by standard necropsy and pathological analysis.

Spleen (Table 1A): murine soluble G70 caused an average about 60% decrease in the percentage of CD3+T cells. In addition, there was an average 5-fold increase in T-helper cells activation and an average 22-fold increase in cytotoxic T cell activation as measured by IL-2 receptor expression. In addition the percentage of immature B cells increased about 2-fold while the percentage of mature B-cells increased 3- to 4-fold.

The total percentage of lymphocytes (T+B) was unchanged compared to control.

Mesenteric Lymph Nodes (Table 1B): soluble G70 treated mice had an average of 25% decrease in the percentage of T cells. There was an average 3-fold increase in % activated T-helper cells and 36-fold increase in activated cytotoxic T-cells as measured by CD25/IL-2 receptor expression. In addition the percentage of immature B cells was increased on average 2-fold whereas mature B cells were up on average 4-fold.

In summary our preliminary observations indicate that G70/APRIL stimulates both T and B cells in the spleen and mesenteric lymph nodes. Pathological analysis revealed that soluble G70 treated mice have slightly enlarged spleens of normal morphology.

G70/APRIL is a Ligand for BCMA and TACI

G70/APRIL is related to the TNF ligand family member AGP3/BlyS. The TNFR receptor family member TACI (FIG. 12) was recently shown to be a receptor for AGP3 ([A-570A patent application ser. no.]). Furthermore, TACI has a match to the orphan TNFR receptor family member BCMA (FIG. 10) in a conserved extracellular cysteine rich domain (FIG. 13). These observations together prompted us to investigate whether G70/APRIL is a ligand for BCMA and TACI and to test whether in addition to TACI AGP3/BlyS is also a ligand for BCMA.

Soluble mouse G70 specifically binds to 293 cells expressing exogenous BCMA (FIG. 14). G70 also binds to 293 cells expressing TACI (FIG. 15). Furthermore soluble G70 specifically blocks AGP3/BlyS binding to cell-surface receptors located on mouse B lymphoma cells (FIG. 16). This suggest that G70 and AGP3 both binds to BCMA and TACI.

smBCMA-Fc and shTACI-Fc Prevent G70 and AGP3 Ligand Binding to Cell-Surface Receptors Soluble BCMA (smBCMA-Fc; FIG. 10) and soluble TACI (shTACI-Fc) were produced in *E. coli* purified to homogeneity and refolded.

Soluble TACI receptor specifically prevents G70 from binding to mouse B cells. (FIG. 17). Furthermore, shBCMA-Fc and shTACI-Fc both prevent binding of AGP3 to B cells (FIG. 18; and FIG. 19 A). Soluble hBCMA-Fc also ameliorates G70 binding to A20 cells (FIG. 19 B).

In summary: 1) both G70 and AGP3 binds the orphan TNFR receptor family members TACI and BCMA; 2) soluble BCMA and TACI both effectively inhibits G70 and AGP3 from binding to B cells; 3) G70 and AGP3 competes for binding to cell-surface receptors.

Effects of TACI-Fc and BCMA-Fc Treatment on the Production of Anti-KLH and Anti-Pneumovax Antibodies.

Treatment with either TACI-Fc or BCMA-Fc significantly inhibited the production of anti-KLH and anti-Pneumovax antibodies. Serum levels of both anti-KLH IgG and IgM were approximately 25% and 19% lower, respectively, in the TACI-Fc-treated mice than controls (FIG. 20). Serum anti-KLH IgG and IgM were approximately 52% and 66% lower, respectively, in the BCMA-Fc-treated mice than controls (FIG. 20). Serum levels of anti-Pneumovax IgM were also lower in the TACI-Fc- and BCMA-Fc-treated mice than controls (24% and 42%, respectively, FIG. 20). Second experiment: Treatment with hBCMA-Fc or Trun-hTACI-Fc reduces anti-Pneumovacs specific IgM levels in normal mice (FIG. 29). Normal mice (n=7) were treated with human BCMA-Fc,truncated TACI-Fc and nonfused Fc as a control in daily doses of 0.5 mg/kg to 15 mg/kg for 7 days. At preimmunization anti-KLH and anti-Pneumovax were undetectable. Antibodies were measured on day 7 and Day 14.

Effects of hBCMA-Fc on Progression of Lupus in NZBX-NZWF1 Mice.

Treatment of NZB/NXWF1 mice with human BCMA-Fc increased survival, decreased proteinurea, decreased the level of anti-dsDNA specific antibodies, and decreased % B cells in peripheral blood. Protocol for SLE: Five months old NZBxNZWF1 mice were treated 3 times/week (mon, wed, fri) for a period of 5 months with the indicated amount of protein. 100 ug dose translates to 4 mg/Kg. Mice were bled at day of treatment to later be analyzed for DNA-specific antibodies, histone proteins, etc. Also at day 0, urine were taken and analyzed for proteins levels. Animals are excluded that already have high levels of protein in the urine, a sign of lupus. Treatment was injected i.p. Urine and blood are taken every 30 days and analyzed until day 150.

Effects of hBCMA-Fc on A20 Lymphoma Cell Growth In Vivo.

Treatment with BCMA-Fc reduces A20 B lymphoma tumor cell growth in Balb/c mice. A20 (0.2 million) cells were implanted, id, on day 0. Treatments with PBS, CHO-Fc, mBCMA-Fc, hBCMA-Fc, mTACI-Fc, hTACI-Fc were given (10 mg/kg, ip) on days 0, 7, 10, 13, 16, 19,22. Tumor measurements were made twice per week. Mice were sacrificed on days 27–31, tumors were snap frozen for RNA isolation, blood was collected and serum samples were frozen.

Effects of hBCMA-Fc on Human Colon Carcinoma HT29 Cell Growth In Vivo.

Treatment with hBCMA-Fc reduces human colon carcinoma cell line HT29 tumor volume growth in mice. $2 \times 10^6$ cells plus 50% matrigel injected subcutaneously into athymic nude mice. Rx: human BCMA-Fc at 2, 5, and 15 mg/kg Q2D, starting at day 0 (n=10/group). Control 1: CHO-Fc at 15 mg/kg Q2D. Control 2: 0.2 ml of PBS Q2D IP. Tumor volume: 3/week, from day 7. Tumor weight at end of study. Body weight 2/week.

Fc-APRIL Effect on B Cells

Fc-humanAPRIL and soluble humanAGP3/BlyS/Tall-1 stimulates incorporation of $^3$H thymidine in primary murine B cells. Purified murine spleen B cells were cultured in presence of various amounts of human Fc-APRIL and untaged AGP3 plus 2 ug/ml of anti-IgM. Data show incorporation of $^3$H thymidine as cpm,and represent mean of triplicate wells.

hBCMA-Fc Effect on APRIL Mediated B Cell Proliferation hBCMA-Fc and hTACI-Fc inhibits Flag-mAPRIL mediated mouse B cell proliferation (FIG. 23). Purified murine spleen B cells were cultured with the indicated amounts of soluble BCMA-Fc and TACI-Fc in presence of 10 ng/ml of Flag-mAPRIL and 2 ug/ml of an anti-IgM for 72 hr. Incorporation of $^3$H thymidine is indicated as cpm. Data shown represent mean of triplicate wells.

hBCMA-Fc Effect on Peripheral Blood B Cell LevelshBCMA-Fc (15 mg/kg ip on day 0, 3, and 6) reduces mouse peripheral blood and B cell levels measured at day seven (FIGS. 24 and 25). Normal mice (n=7) were treated with human BCMA-Fc and nonfused Fc as a control in day 0,3, and 6 (15 mg/kg). Peripheral blood and spleen B cell (B220) level were measured on day 7.

Flag-mAPRIL and hAGP3 mediated IgA production is inhibited by hBCMA-Fc and hTACI-Fc in vitro (FIG. 26. Purified murine spleen B cells were cultured with LPS (100 ng/ml),AGP3 (10 ng/ml),Flag-APRIL (10 ng/ml) or plus BCMA-Fc (100 ng/ml) and TACI-Fc (100 ng/ml) for 12 days. Culture supernatants were collected on day 7 and day 12 for detecting IgA level. Flag-mAPRIL and hAGP3 mediated IgG production is inhibited by hBCMA-Fc and hTACI-Fc in vitro (FIG. 27).

BCMA-Fc Effect on Total Immunoglobulin In Vivo.

Total IgE and IgA levels are reduced in normal mice treated with mBCMA-Fc and trun hTACI-Fc (5 mg/kg ip day 0, 3, and 6). Normal mice (n=7) were treated with human BCMA-Fc Truncated TACI-Fc and nonfused Fc as a control in day 0,3, and 6 (5 mg/kg). Immunoglobulin levels in serum were measured on day 7.

Anti-mAPRIL Specific Monoclonal Antibody Effect.

The anti-mAPRIL specific monoclonal antibody #c19 inhibits Flag-mAPRIL mediated mouse B cell proliferation (FIG. 30). Purified murine spleen B cells were cultured in presence 10 ng/ml mFlag-APRIL plus 2 ug/ml of anti-IgM. anti-Flag-APRIL monoclonal antibody c-19 and rat IgG control were added into culture in same time. Data show incorporation of $^3$H thymidine as cpm,and represent mean of triplicate well2. Treatment with the anti-mAPRIL specific monoclonal antibody #c19 inhibits generation of anti-Pneumovacs specific antibodies in vivo (FIG. 31).

APRIL Binding and Effect on Tumor Cells.

APRIL binds to a number of tumor cell lines (FIG. 36). APRIL binding to human tumor cell lines were determined by incubating cell with lug/ml Fc-APRIL or Flag-APRIL following FITC labeled secondary antibody staining and FACS analysis. APRIL stimulates U266-B1 cell growth and that this can be inhibited by BCMA-Fc or TACI-Fc (FIG. 37). U266 cells were cultured in presence 10 ng/ml human Fc-APRIL or plus 50 ng/ml soluble BCMA-Fc, Truncated TACI-Fc for 48 hr. Incorporation of $^3$H thymidine is indicated as cpm. Data shown represent mean of triplicate wells.

What is claimed is:

1. A method of inhibiting TACI activity, BCMA activity, or both in a mammal, which comprises administering a specific binding partner for APRIL, wherein said specific binding partner comprises a TACI/BCMA extracellular consensus sequence (SEQ ID NO:13) covalently attached to a vehicle.

2. The method of claim 1, wherein the vehicle is an Fc domain.

* * * * *